(12) United States Patent
Arioli et al.

(10) Patent No.: US 6,495,740 B1
(45) Date of Patent: Dec. 17, 2002

(54) MANIPULATION OF CELLULOSE AND/OR β-1,4-GLUCAN

(75) Inventors: Antonio Arioli, Duffy (AU); Richard E. Williamson, Murrumbateman (AU); Andreas S. Betzner, Page (AU); Liangcai Peng, Turner (AU)

(73) Assignee: The Austrailian National University, Acton Australian Capital Territory (AU)

( * ) Notice: Subject to any disclaimer, the term of this patent is extended or adjusted under 35 U.S.C. 154(b) by 0 days.

(21) Appl. No.: 09/221,013

(22) Filed: Dec. 23, 1998

Related U.S. Application Data

(63) Continuation of application No. PCT/AU97/00402, filed on Jun. 24, 1997.

(30) Foreign Application Priority Data

Jun. 27, 1996 (AU) .............................................. 0699/96

(51) Int. Cl.$^7$ .......................... A01H 1/00; C07H 21/04; C07K 14/415; C12N 5/14; C12N 9/00
(52) U.S. Cl. ...................... 800/284; 536/23.1; 536/23.2; 536/23.6; 536/24.31; 536/23.32; 536/23.35; 435/6; 435/69.1; 435/468; 435/410; 435/419; 435/320.1; 800/278; 800/290; 800/295; 800/298; 800/306; 800/314; 800/320.2; 800/320.3; 800/320; 800/319
(58) Field of Search .............................. 536/23.1, 23.2, 536/23.6, 24.31, 24.32, 24.33; 435/6, 69.1, 468, 410, 419, 320.1; 800/278, 284, 290, 295, 298, 306, 314, 320.2, 320.3, 320, 319

(56) References Cited

U.S. PATENT DOCUMENTS

| | | | |
|---|---|---|---|
| 5,268,274 A | 12/1993 | Ben-Bassat et al. | 435/69.1 |
| 5,712,107 A | 1/1998 | Nichols | 435/15 |
| 5,723,764 A | 3/1998 | Nichols et al. | 800/205 |

FOREIGN PATENT DOCUMENTS

| | | | |
|---|---|---|---|
| EP | 0 562 836 A1 | 3/1993 | ............ C12N/15/54 |
| EP | 0 875 575 A2 | 11/1998 | ............ C12N/15/54 |
| WO | 90/12098 | 10/1990 | ............ C12N/15/54 |
| WO | 91/13988 | 9/1991 | ............ C12N/15/54 |
| WO | 92/18631 | 10/1992 | ............ C12N/15/54 |
| WO | 97/33974 | 9/1997 | |
| WO | 98/18949 | 5/1998 | ............ C12N/15/82 |
| WO | 98/35051 | 8/1998 | ............ C12N/15/82 |
| WO | 98/44780 | 10/1998 | ............ A01H/5/00 |

OTHER PUBLICATIONS

Okazaki et al. Molecular and Cellular Biology. 1995. vol. 15 (8): 4545–4552. Accession No.: D38414 is disclosed).*
Brown et al. Trends in Plant Sciences. May 1996 vol. 1, No. 5, pp. 149–156).*
Kossmann et al. Progress in Biotechnology. 10–Proceeding of International conference. 1995. pp. 271–278.*
De Carvalho et al. The EMBO J. 1992. vol. 11: pp. 2595–2602.*
Kellett et al. Biochem J. 1990. vol. 272: 369–376.*
Simmons et al. Plant Molecular Biology. 1992. Jan. issue. vol. 18:1, pp. 33–45.*
Amor Y. et al. (1991) "Evidence for a cyclic diguanylic acid–dependent cellulose synthase in plants"; *The Plant Cell* 3:989–995.
AC AA042132, Sep. 5, 1996, Newman T. et al. "Genes galore: a summary of methods for accessing results from large–scale partial sequencing of anonymous *Arabidopsis* cDNA clones"; Database EM EST Online! EBI Hinxton, UK. Abstract.
Amor et al. (1995) "A Membrane–Associated Form of Sucrose Synthase and Its Potential Role In Synthesis of Cellulose and Callose in Plants" *Proc. Natl. Acad. Sci. USA* 92:9353–9357.
Arioli et al. (1998) ". . . Response: How Many Cellulose Synthase–Like Gene Products Actually Make Cellulose?" *Elsevier Science Ltd*. 3:165–166.
Arioli et al. (1998) "Molecular Analysis of Cellulose Biosynthesis in *Arabidopsis*" *Science* 279:717–720.
Carpita and Vergara (1998) "A Recipe for Cellulose" *Science* 279:672–673.
Chang et al. (1988) "Restriction Fragment Length Polymorphism Linkage Map For *Arabidopsis thaliana*" *Proc. Natl. Acad. Sci. USA* 85:6856–6860.
Chapple and Carpita (1998) "Plant Cell Walls As Targets For Biotechnology" *Current Opinion in Plant Biology* 1:179–185.
Cutler and Somerville (1997) "Cullose Synthesis: Cloning in silico" *Current Biology* 7:R108–R111.
Delmer, Deborah P. (1998) "A Hot Mutant For Cellulose Synthesis" *Elsevier Science Ltd*. 3:164–165.
Delmer et al. (1995) "The Potential Role of A Membrane–Associated Form of Sucrose Synthase in Synthesis of Cellulose" Abstract. *Plant Physiol*. 108(2 Suppl.) p. 8.

(List continued on next page.)

Primary Examiner—Phuong T. Bui
(74) Attorney, Agent, or Firm—Greenlee, Winner and Sullivan, P.C.

(57) ABSTRACT

The invention relates generally to isolated genes which encode polypeptides involved in cellulose biosynthesis in plants and transgenic plants expressing same in sense or antisense orientation, or as ribozymes, co-suppression or gene-targeting molecules. More particularly, the present invention is directed to a nucleic acid molecule isolated from *Arabidopsis thaliana*, *Oryza sativa*, wheat, barley, maize, Brassica ssp., *Gossypium hirsutum* ssp. and Eucalyptus ssp. which encode an enzyme which is important in cellulose biosynthesis, in particular the cellulose synthase enzyme and homologues, analogues and derivatives thereof and uses of same in the production of transgenic plants expressing altered cellulose biosynthetic properties.

10 Claims, 21 Drawing Sheets

OTHER PUBLICATIONS

Delmer et al. (1991) "Identification and Characterization of Genes and Gene Products Involved in β–Glucan Synthesis" Abstract. *J. Cell Biochem*. Suppl. O (15 Part A) p. 13.

Haigler and Blanton (1996) "New Hope For Old Dreams: Evidence That Plant Cellulose Synthase Genes Have Finally Been Identified" *Proc. Natl. Acad. Sci. USA* 93:12082–12085.

Hayashi and MacLachlan (1984) "Pea Xyloglucan and Cellulose" *Plant Physiol*. 75:596–604.

Herth, W. (1985) "Plasma–Membrane Rosettes Involved In Localized Wall Thickening During Xylem Vessel Formation of *Lepidium sativum* L." *Planta* 164:12–21.

Kohel et al. (1993) "Incorporation of [$^{14}$C]Glucose into Crystalline Cellulose in Aberrant Fibers of a Cotton Mutant" *Crop Science* 33:1036–1040.

Konieczny and Ausubel (1993) "A Procedure for Mapping *Arabidopsis* Mutations Using Co–Dominant Ecotype–Specific PCR–Based Markers" *The Plant Journal* 4:403–410.

Levy et al. (1991) "Simulations of the Static and Dynamic Molecular Conformations of Xyloglucan. The Role of the Fucosylated Sidechain in Surface–Specific Sidechain Folding" *The Plant Journal* 1:195–215.

Li and Brown (1993) "β–Glucan Synthesis In the Cotton Fiber, II. Regulation and Kinetic Properties of β–Glucan Synthases" *Plant Physiol*. 101:1143–1148.

Li et al. (1993) "β–Glucan Synthesis In the Cotton Fiber, III. Identification of UDP–Glucose–Binding Subunits of β–Glucan Synthases By Photoaffinity Labeling With [β–$^{32}$P] 5'N$_3$–UDP–Glucose" *Plant Physiol*. 101:1149–1156.

Matthysse et al. (1995) "Genes Required for Cellulose Synthesis In *Agrobacterium tumefaciens*" *Journal of Bacteriology* 177:1069–1075.

Mayer et al. (1991) "Polypeptide Composition of Bacterial Cyclic Diguanylic Acid–Dependent Cellulose Synthase and the Occurrence of Immunologically Crossreacting Proteins in Higher Plants" *Proc. Natl. Acad. Sci. USA* 88:5472–5476.

Pear et al. (1996) "Higher Plants Contain Homologs of the Bacterial *celA* Genes Encoding the Catalytic Subunit of Cellulose Synthase" *Proc. Natl. Acad. Sci. USA* 93:12637–12642.

Saxena and Brown (1997) "Identification of Cellulose Synthase(s) In Higher Plants: Sequence Analysis of Processive β–Glycosyltransferases With the Common Motif" Abstract only. *Cellulose* 4:33–49.

Saxena et al. (1995) "Multidomain Architecture of β–Glycosyl Transferases: Implications for Mechanism of Action" *Journal of Bacteriology* 177:1419–1424.

Saxena et al. (1990) "Cloning and Sequencing of the Cellulose Synthase Catalytic Subunit Gene of *Acetobacter xylinum*" *Plant Molecular Biology* 15:673–683.

Wang and Loopstra (1998) Cloning and Characterization of a Cellulose Synthase cDNA (Accession No. *AF081534*) From Xylem of Hybrid Poplar (*Populus tremula X Populus alba*)(PGR98–179) *Plant Physiol*. 118:1101.

Wong et al. (1990) "Genetic Organization of the Cellulose Synthase Operon in *Acetobacter xylinum*" *Proc. Natl. Acad. Sci USA* 87:8130–8134.

Wu, C. (1996) "Cottoning Onto How Plants Make Cellulose" *Science News* 150:279.

Wu et al. (1998) AraxCelA, A New Member of Cellulose Synthase Gene Family From *Arabidopsis thaliana* (Accession No. AF062485) (PGR98–114) *Plant Physiol* 117:1125.

* cited by examiner

```
                      10          20          30          40          50          60
RSW1     MEASAGLVAGSYRRNELVRIRHESDGG..TKPLKNMNGQICQICGDDVGLAETGDVFVAC
Ath-A    MNTGGRLIAGSHNRNEFVLINADESAR..IRSVQELSGQTCQICGDEIELTVSSELFVAC
S0542    MAANAGMVAGSRNRNEFVMIRPDGDAPPAKPGKSVNGQVCQICGDTVGVSATGDVFVAC
Ath-B                       MESEGETAGKPMKNIVPQTCQICSDNVGKTVDGDRFVAC
CelA1                                 MMESGVPVCHTCGEHVGLNVNGEPFVAC
CelA2
D48636

70          80          90         100         110         120
RSW1     NECAFPVCRPCYEYERKDGTQCCPQCKTRFRRHRGSPRVEGDEDEDDVDDIENEFNYAQG
Ath-A    NECAFPVCRPCYEYERRREGNQACPQCKTRYKRIKGSPRVDGDDEEEDIDDLEYEFDHGM
S0542    NECAFPVCRPCYEYERKEGNQCCPQCKTRYKRHKGCPRVQGDEEEEDVDDLDNEFHYKHG
Ath-B    DICSFPVCRPCYEYERKDGNQSCPQCKTRYKRLKGSPAIPGDKDEDGLADEGTVEFNYPQ
CelA1    HECNFPICKSCFEYDLKEGRKACLRCGSPYDENLLDDVEKATGDQSTMAAHLNKSQDVGI
CelA2
D48636
```

Figure 9A

```
              130       140       150       160       170       180
RSW1                    RHQRHGEEFSSSSRHESQPIPLLTHGHTVSGEIRTPDTQSVRTT
Ath-A   ANKA..........
S0542   DPEHAEAALSSRLNTGRGGLDSAPPGSQIPLLTYCDEDADMYSDRHALIVPPSTGYGNR
Ath-B   NGKGPEWQI......QRQGEDVDLSSSRHEQHRIPRLTSGQQISGEIPDASPDRHSIR
Cel-A1  K.EKISERMLGWHLTRGKGEEMGEPQYDKEVSHNHLPRLTSRQDTSGEFSAASPERLSVS
Cel-A2
D48636

190       200       210       220       230       240
RSW1    SGPLGPSDRNAISSPYIDPRQPVPVRIVDPSKDLNSYGLGNVDWKERVEGWKLKQEKNML
Ath-A   VY............PAPFTDSSAPPQARSMVPQKDIAEYGYGSVAWKDRMEVWKRRQGEKLQ
S0542   SG............TSSYVDPSVPVPVRIVDPSKDLNSYGINSVDWQERVASWRNKQDKNMM
Ath-B   ST............IAGGKRLPYSSDVNQSPNRRIVDPVGLGNVAWKERVDGWKMKQEKNTG
Cel-A1              ..HARHISSVSTLDSEMAEDNGNSIWKNRVESWKEKKNKKKK
Cel-A2
D48636                                STTRPGNVAWKERVDGWKLKQDKGAI
```

Figure 9B

```
              250         260         270         280         290         300
RSW1     QMT.......GKYHEGKGGEIEGTGSNGEELQMADDTRLPMSRVVPIPSSRLTPYRVVIIL
Ath-A    VIK.......HEGGNNGRGSNDDDELDDPDMPMMDEGRQPLSRKLPIRSSRINPYRMLILC
S0542    QVA.......NKYPEARGGDMEGTGSNGEDIQMVDDARLPLSRIVPIPSNQLNLYRIVIIL
Ath-B    PV....STQAASERGGVDIDASTDILADEALLNDEARQLLSRKVSIPSSRINPYRMVIML
Cel-A1   PAT.......TKVEREAEIPPEQQMEDKPAPDASQPLSTIIPIPKSRLAPYRTVIIM
Cel-A2
D48636   PMTNGTSIAPSEGRGVGDIDASTDYNMEDALLNDETRQPLSRKVPLPSSRINPYRMVIVL 310         320         330         340         350         360
RSW1     RLIILCFFLQYRTTHPVKNAYPLWLTSVICEIWFAFSWLLDQFPKWYPINRETYLDRLAI
Ath-A    RLAILGLFFHYRILHPVNDAYGLWLTSVICEIWFAVSWILDQFPKWYPIERETYLDRLSL
S0542    RLIILMFFQYRVTHPVRDAYGLWLVSVICEIWLPLSWLLDQFPKWYPINRETYLDRLAL
Ath-B    RLVILCLFLHYRITNPVPNAFALWLVSVICEIWFALSWILDQFPKWFPVNRETYLDRLAL
Cel-A1   RLIILGLFFHYRVTNPVDSAFGLWLTSVICEIWFAFSWVLDQFPKWYPVNRETYIDRLSA
Cel-A2
D48636   RLVVLSIFLHYRITNPVRNAYPLWLLSVICEIWFALSWILDQFPKWFPINRETYLDRLAL
```

Figure 9C

```
              370         380         390         400         410         420
RSW1    RYDRDGEPSQLVPVDVFVSTVDPLKEPPLVTANTVLSILSVDYPVDKVACYVSDDGSAML
Ath-A   RYEKEGKPSGLAPVDVFVSTVDPLKEPPLITANTVLSILAVDYPVDKVACYVSDDGAAML
S0542   RYDREGEPSQLAPIDVFVSTVDPLKEPPLITANTVLSILAVDYPVDKVSCYVSDDGSAML
Ath-B                RLVILCLFLHYRITNPVPNAFALWLVSVICEIWFALSWILDQFPKWFPVNRETYLDRLAL
Cel-A1  RYEREGEPDELAAVDFFVSTVDPLKEPPLITANTVLSILALDYPVDKVSCYISDDGAAML
Cel-A2
D48636  RYDREGEPSQLAAVDIFVSTVDPMKEPPLVTANTVLSILAVDYPVDKVSCYVSDDGAAML 430         440         450         460         470         480
RSW1    TFESLSETAEFAKKWVPFCKKFNIEPRAPEFYFAQKIDYLKDKIQPSFVKERRAMKREYE
Ath-A   TFEALSDTAEFARKWVPFCKKFNIEPRAPEWYFSQKMDYLKNKVHPAFVRERRAMKRDYE
S0542   TFEALSETAEFARKWVPFCKKHNIEPRAPEFYFAQKIDYLKDKIQPSFVKERRAMKREYE
Ath-B   SFESLAETSEFARKWVPFCKKYSIEPRAPEWYFAAKIDYLKDKVQTSFVKDRRAMKREYE
Cel-A1  TFESLVETADFARKWVPFCKKFSIEPRAPEFYFSQKIDYLKDKVQPSFVKERRAMKRDYE
Cel-A2           RRWVPFCKKHNVEPRAPEFYFNEKIDYLKDKVHPSFVKERRAMKREYE
D48636  TFDALAETSEFARKWVPFVKKYNIEPRAPEWYFSQKIDYLKDKVHPSFVKDRRAMKREYE
```

Figure 9D

```
              490        500        510        520        530        540
RSW1     EFKVRINALVAKAQKIPEEGWTMQDGTPWPGNNTRDHPGMIQVFLGHSGGLDTDGNELPR
Ath-A    EFKVKINALVATAQKVPEEGWTMQDGTPWPGNNVRDHPGMIQVFLGHSGVRDTDGNELPR
S0542    EFKVRINALVAKAQKVPEEGWTMADGTAWPGNNPRDHPGMIQVFLGHSGGLDTDGNELPR
Ath-B    EFKIRINALVSKALKCPEEGWVMQDGTPWPGNNTGDHPGMIQVFLGQNGGLDAEGNELPR
Cel-A1   EYKIRINALVAKAQKTPDEGWTMQDGTSWPGNNPRDHPGMIQVFLGYSGARDIEGNELPR
Cel-A2   EFKVRINALVAKAQKKPEEGWVMQDGTPWPGNNTRDHPGMIQVYLGSAGALDVDGKELPR
D48636   EFKVRINGLVAKAQKVPEEGWIMQDGTPWPGNNTRDHPGMIQVFLGHSGGLDTEGNELPR 550        560        570        580        590        600
RSW1     LIYVSREKRPGFQHHKKAGAMNALIRVSAVLTNGAYLLNVDCDHYFNNSKAIKEAMCFLM
Ath-A    LVYVSREKRPGFDHHKKAGAMNSLIRVSAVLSNAPYLLNVDCDHYINNSKAIRESMCFMM
S0542    LVYVSREKRPGFQHHKKAGAMNALIRVSAV
Ath-B    LVYVSREKRPGFQHHKKAGAMNALVRVSAVLTNGPFILNLDCDHYINNSKALREAMCFLM
Cel-A1   LVYVSREKRPGYQHHKKAGAENALVRVSAVLTNAPFILNLDCDHYVNNSKAVREAMCFLM
Cel-A2   LVYVSREKRPGYQHHKKAGAENALVRVSAVLTNAPFILNLDCDHYINNSKAMREAMCFLM
D48636   LVYVSREKRPGFQHHKKAGAMNALVRVSAVLTNGQYMLNLDCDHYINNSKALREAMCFLM
```

Figure 9E

```
               610        620        630        640        650        660
RSW1     DPAIGKKCCYVQFPQRFDGIDLHDRYANRNIVFFDINMKGLDGIQGPVYVGTGCCFNRQA
Ath-A    DPQSGKKVCYVQFPQRFDGIDRHDRYSNRNVFFDINMKGLDGIQGPIYVGTGCVFRKQA
S0542
Ath-B    DPNLGKQVCYVQFPQRFDGIKNDRYANRNTVFFDINLRGLDGIQGPVYVGTGCVFNRQA
Cel-A1   DPQVGRDVCYVQFPQRFDGIDRSDRYANRNTVFFDVNMKGLDGIQGPVYVGTGCVFNRQA
Cel-A2   DPQFGKKLCYVQFPQRFDGIDRHDRYANRNVFFDINMLGLDGLQGPVYVGTGCVFNRQA
D48636   DPNLGRSVCYVQFPQRFDGIDRNDRYANRNTVFFDINLRGLDGIQGPVYVGTGCVFNRTA 670        680        690        700        710        720
RSW1     LYGYDPVLTEEDLEPNIIVKSCCGSRKKGKSSKKYNYE......................KRR
Ath-A    LYGFDAPKKKKPPGKTCNCWPKWCCLCCGLRKKSKTKA......................KDKKT
S0542
Ath-B    LYGYEPPIKVKHKKPSLLSKLCGGSRKKNSKAKKESDK..........................KKSGR
Cel-A1   LYGYGPPSMPSFPKSSS.....SSCSCCCPGKKEPKDPS......................ELYRDA
Cel-A2   LYGYDPPVSEKRPKMTCDCWPSWCCCCCGSRKKSKKKGEKKGLLGGLLYGKKKKMMGKN
D48636   LYGYEPPIKQKKKGSFLSSLCGGRKKASKSKKKSSDK..........................KKSNK

Figure 9F
```

```
              730       740       750       760       770       780
RSW1     GINRSDSNAPLFNMEDIDEGFEGYDDERSILMSQRSVEKRFGQSPVFIAATFMEQGGIPP
Ath-A    NTKETSKQIHALENVDEGVIVPVSNVEKRSEATQLKLEKKFGQSPVFVASAVLQNGGVPR
S0542
Ath-B    HTDS.TVPVFNLDDIEEGVEGAGFDDEKALLMSQMSLEKRFGQSAVFVASTLMENGGVPP
Cel-A1   KREELDAAIFNLREIDN......YDEYERSMLISQTSFEKTFGLSSVFIESTLMENGGVAE
Cel-A2   YVKKGSAPVFDLEEIEEGLEG.YEELEKSTLMSQKNFEKRFGQSPVFIASTLMENGGLPE
D48636   HVDS.AVPVFNLEDIEEGVEGAGFDDEKSLLMSQMSLEKRFGQSAAFVASTLMEYGGVPQ 790       800       810       820       830       840
RSW1     TTNPATLLKEAIHVISCGYEDKTEWGKEIGWIYGSVTEDILTGFKMHARGWISIYCNPPR
Ath-A    NASPACLLREAIQVISCGYEDKTEWGKEIGWIYGSVTEDILTGFKMHCHGWRSVYCMPKR
S0542
Ath-B    SATPENFLKEAIHVISCGYEDKSDWGMEIGWIYGSVTEDILTGFKMHARGWRSIYCMPKL
Cel-A1   SANPSTLIKEAIHVISCGYEEKTAWGKEIGWIYGSVTEDILTGFKMHCRGWRSIYCMPLR
Cel-A2   GTNSTSLIKEAIHVISCGYEEKTEWGKEIGWIYGSVTEDILTGFKMHCRGWKSVYCVPKR
D48636   SATPESLLKEAIHVISCGYEDKTEWGTEIGWIYGSVTEDILTGFKMHARGWRSIYCMPKR
```

Figure 9G

```
                       850               860               870               880               890        900
RSW1      PAFKGSAPINLSDRLNQVLRWALGSIEILLSRHCPIWYGYHG.RLRLLERIAYINTIVYP
Ath-A     AAFKGSAPINLSDRLHQVLRWALGSVEIFLSRHCPIWYGYGG.GLKWLERFSYINSVVYP
S0542
Ath-B     PAFKGSAPINLSDRLNQVLRWALGSVEILFSRHCPIWYGYNG.RLKFLERFAYVNTTIYP
Cel-A1    PAFKGSAPINLSDRLHQVLRWALGSVEIFLSRHCPLWYGFGGGRLKWLQRLAYINTIVYP
Cel-A2    PAFKGSAPINLSDRLHQVLRWALGSVEIFLSRHCPLWYGYGG.KLKWLERLAYINTIVYP
D48636    PAFKGSAPINLSDRLNQVLRWALGSVEILFSRHCPIWYGYGG.RLKFLERFAYINTTIYP 910               920               930               940               950        960
RSW1      ITSIPLIAYCILPAFCLITDRFIIPEISNYASIWFILLFISIAVTGILELRWSGVSIEDW
Ath-A     WTSLPLIVYCSLPAVCLLTGKFIVPEISNYAGILFMLMFISIAVTGILEMQWGGVGIDDW
S0542
Ath-B     ITSIPLLMYCTLLAVCLFTNQFIIPQISNIASIWFLSLFLSIFATGILEMRWSGVGIDEW
Cel-A1    FTSLPLIAYCSLPAICLLTGKFIIPTLSNLASVLFLGLFLSIIVTAVLELRWSGVSIEDL
Cel-A2    FTSIPLLAYCTIPAVCLLTGKFIIPTLSNLTSVWFLALFLSIIATGVLELRWSGVSIQDW
D48636    LTSIPLLIYCVLPAICLLTGKFIIPEISNFASIWFISLFISIFATGILEMRWSGVGIDEW
```

Figure 9H

```
                970       980       990       1000      1010      1020
RSW1     WRNEQFWVIGGTSAHLFAVFQGLLKVLAGIDTNFTVTSKATDEDGDFAELYIFKWTALLI
Ath-A    WRNEQFWVIGGASSHLFALFQGLLKVLAGVNTNFTVTSKAAD.DGAFSELYIFKWTTLLI
S0542
Ath-B    WRNEQFWVIGGVSAHLFAVFQGILKVLAGIDTNFTVTSKASDEDGDFAELYLFKWTTLLI
Cel-A1   WRNEQFWVIGGVSAHLFAVFQGFLKMLAGIDTNFTVTAKAAD.DADFGELYIVKWTTLLI
Cel-A2   WRNEQFWVIGGVSAHLFAVFQGLLKVLAGVDTNFTVTAKAAD.DTEFGELYLFKWTTLLI
D48636   WRNEQFWVIGGISAHLFAVFQGLLKVLAGIDTNFTVTSKASDEDGDFAELYMFKWTTLLI 1030      1040      1050      1060      1070      1080
RSW1     PPTTVLLVNLIGIVAGVSYAVNSGYQSWGPLFGKLFFALWVIAHLYPFLKGLLGRQNRTP
Ath-A    PPTTLLIINIIGVIVGVSDAISNGYDSWGPLFGRLFFALWVIVHLYPFLKGMLGKQDKMP
S0542
Ath-B    PPTTLLIVNLVGVVAGVSYAINSGYQSWGPLFGKLFFAFWVIVHLYPFLKGLMGRQNRTP
Cel-A1   PPTTLLIVNMVGVVAGFSDALNKGYEAWGPLFGKVFFSFWVILHLYPFLKGLMGRQNRTP
Cel-A2   PPTTLILNMVGVVAGVSDAINNGYGSWGPLFGKLFFAFWVILHLYPFLKGLMGRQNRTP
D48636   PPTTILIINLVGVVAGISYAINSGYQSWGPLFGKLFFAFWVIVHLYPFLKGLMGRQNRTP
```

Figure 9I

```
                 1090              1100              1110              1120
RSW1     TIVIVWSVLLASIFSLLWVRINPFVDANPNANNFNGKGGVF
Ath-A    TIIVVWSILLASILTLLWVRINPFVAK.GGPVLEICGLNCGN
S0542
Ath-B    TIVVVWSVLLASIFSLLWVRIDPFTSRVTGPDILECGINC
Cel-A1   TIVVLWSVLLASVFSLVWVRINPFVSTADSTTVSQSCISIDC
Cel-A2   TIVVLWSILLASIFSLVWVRIDPFLPKQTGPVLKQCGVEC
D48636   TIVVVWAILLASIFSLLWVRIDPFTTRVTGPDTQTCGINC
```

Figure 9J

```
                        SEQUENCE LISTING

<160> NUMBER OF SEQ ID NOS:   37

<210> SEQ ID NO 1
<211> LENGTH: 2248
<212> TYPE: DNA
<213> ORGANISM: Arabidopsis thaliana
<220> FEATURE:
<221> NAME/KEY: CDS
<222> LOCATION: (1)..(1887)

<400> SEQUENCE: 1 cga gct atg aag aga gag tat gaa gag ttt aaa gtg agg ata aat gct      48
Arg Ala Met Lys Arg Glu Tyr Glu Glu Phe Lys Val Arg Ile Asn Ala
 1               5                  10                  15
```

-continued

| | |
|---|---|
| ctt gtt gcc aaa gca cag aaa atc cct gga gaa ggc tgg aca atg cag<br>Leu Val Ala Lys Ala Gln Lys Ile Pro Gly Glu Gly Trp Thr Met Gln<br>                20                        25                        30 | 96 |
| gat ggt act ccc tgg cct ggt aac aac act aga gat cat cct gga atg<br>Asp Gly Thr Pro Trp Pro Gly Asn Asn Thr Arg Asp His Pro Gly Met<br>        35                        40                        45 | 144 |
| ata cag gtg ttc tta ggc cat agt ggg ggt ctg gat acc gat gga aat<br>Ile Gln Val Phe Leu Gly His Ser Gly Gly Leu Asp Thr Asp Gly Asn<br>50                        55                        60 | 192 |
| gag ctg cct aga ctc atc tat gtt tct cgt gaa aag cgg cct gga ttt<br>Glu Leu Pro Arg Leu Ile Tyr Val Ser Arg Glu Lys Arg Pro Gly Phe<br>65                        70                        75                        80 | 240 |
| caa cac cac aaa aag gct gga gct atg aat gca tcg atc cgt gta tct<br>Gln His His Lys Lys Ala Gly Ala Met Asn Ala Ser Ile Arg Val Ser<br>                        85                        90                        95 | 288 |
| gct gtt ctt acc aat gga gca tat ctt ttg aac gtg gat tgt gat cat<br>Ala Val Leu Thr Asn Gly Ala Tyr Leu Leu Asn Val Asp Cys Asp His<br>                100                      105                    110 | 336 |
| tac ttt aat aac agt aag gct att aaa gaa gct atg tgt ttc atg atg<br>Tyr Phe Asn Asn Ser Lys Ala Ile Lys Glu Ala Met Cys Phe Met Met<br>                115                      120                    125 | 384 |
| gac ccg gct att gga aag aag tgc tgc tat gtc cag ttc cct caa cgt<br>Asp Pro Ala Ile Gly Lys Lys Cys Cys Tyr Val Gln Phe Pro Gln Arg<br>130                        135                      140 | 432 |
| ttt gac ggt att gat ttg cac gat cga tat gcc aac agg aat ata gtc<br>Phe Asp Gly Ile Asp Leu His Asp Arg Tyr Ala Asn Arg Asn Ile Val<br>145                        150                      155                    160 | 480 |
| ttt ttc gat att aac atg aag ggg ttg gat ggt atc cac ggt cca gta<br>Phe Phe Asp Ile Asn Met Lys Gly Leu Asp Gly Ile His Gly Pro Val<br>                165                      170                    175 | 528 |
| tat gtg ggt act ggt tgt tgt ttt aat agg cag gct cta tat ggg tat<br>Tyr Val Gly Thr Gly Cys Cys Phe Asn Arg Gln Ala Leu Tyr Gly Tyr<br>                180                      185                    190 | 576 |
| gat cct gtt ttg acg gaa gaa gat tta gaa cca aat att att gtc aag<br>Asp Pro Val Leu Thr Glu Glu Asp Leu Glu Pro Asn Ile Ile Val Lys<br>                195                      200                    205 | 624 |
| agc tgt tgc ggg tca agg aag aaa ggt aaa agt agc aag aag tat aac<br>Ser Cys Cys Gly Ser Arg Lys Lys Gly Lys Ser Ser Lys Lys Tyr Asn<br>210                        215                      220 | 672 |
| tac gaa aag agg aga ggc atc aac aga agt gac tcc aat gct cca ctt<br>Tyr Glu Lys Arg Arg Gly Ile Asn Arg Ser Asp Ser Asn Ala Pro Leu<br>225                        230                      235                    240 | 720 |
| ttc aat atg gag gac atc gat gag ggt ttt gaa ggt tat gat gat gag<br>Phe Asn Met Glu Asp Ile Asp Glu Gly Phe Glu Gly Tyr Asp Asp Glu<br>                245                      250                    255 | 768 |
| agg tct att cta atg tcc cag agg agt gta gag aag cgt ttt ggt cag<br>Arg Ser Ile Leu Met Ser Gln Arg Ser Val Glu Lys Arg Phe Gly Gln<br>                260                      265                    270 | 816 |
| tcg ccg gta ttt att gcg gca acc ttc atg gaa caa ggc ggc att cca<br>Ser Pro Val Phe Ile Ala Ala Thr Phe Met Glu Gln Gly Gly Ile Pro<br>                275                      280                    285 | 864 |
| cca aca acc aat ccc gct act ctt ctg aag gag gct att cat gtt ata<br>Pro Thr Thr Asn Pro Ala Thr Leu Leu Lys Glu Ala Ile His Val Ile<br>290                        295                      300 | 912 |
| agc tgt ggt tac gaa gac aag act gaa tgg ggc aaa gag att ggt tgg<br>Ser Cys Gly Tyr Glu Asp Lys Thr Glu Trp Gly Lys Glu Ile Gly Trp<br>305                        310                      315                    320 | 960 |
| atc tat ggt tcc gtg acg gaa gat att ctt act ggg ttc aag atg cat<br>Ile Tyr Gly Ser Val Thr Glu Asp Ile Leu Thr Gly Phe Lys Met His | 1008 |

|   |   |
|---|---|
| gcc cgg ggt tgg ata tcg atc tac tgc aat cct cca cgc cct gcg ttc<br>Ala Arg Gly Trp Ile Ser Ile Tyr Cys Asn Pro Pro Arg Pro Ala Phe<br>         340                         345                        350 | 1056 |
| aag gga tct gca cca atc aat ctt tct gat cgt ttg aac caa gtt ctt<br>Lys Gly Ser Ala Pro Ile Asn Leu Ser Asp Arg Leu Asn Gln Val Leu<br>         355                         360                        365 | 1104 |
| cga tgg gct ttg gga tct atc gag att ctt ctt agc aga cat tgt cct<br>Arg Trp Ala Leu Gly Ser Ile Glu Ile Leu Leu Ser Arg His Cys Pro<br>370                        375                        380 | 1152 |
| atc tgg tat ggt tac cat gga agg ttg aga ctt ttg gag agg atc gct<br>Ile Trp Tyr Gly Tyr His Gly Arg Leu Arg Leu Leu Glu Arg Ile Ala<br>385                        390                        395                  400 | 1200 |
| tat atc aac acc atc gtc tat cct att aca tcc atc cct ctt att gcg<br>Tyr Ile Asn Thr Ile Val Tyr Pro Ile Thr Ser Ile Pro Leu Ile Ala<br>                  405                        410                        415 | 1248 |
| tat tgt att ctt ccc gct ttt tgt ctc atc acc gac aga ttc atc ata<br>Tyr Cys Ile Leu Pro Ala Phe Cys Leu Ile Thr Asp Arg Phe Ile Ile<br>         420                        425                        430 | 1296 |
| ccc gag ata agc aac tac gcg agt att tgg ttc att cta ctc ttc atc<br>Pro Glu Ile Ser Asn Tyr Ala Ser Ile Trp Phe Ile Leu Leu Phe Ile<br>         435                        440                        445 | 1344 |
| tca att gct gtg act gga atc ctg aaa ctg aaa tgg aac ggt gtg agc<br>Ser Ile Ala Val Thr Gly Ile Leu Lys Leu Lys Trp Asn Gly Val Ser<br>         450                        455                        460 | 1392 |
| att gag gat tgg tgg agg aac aac cag ttc tgg gtc att ggt ggc aca<br>Ile Glu Asp Trp Trp Arg Asn Asn Gln Phe Trp Val Ile Gly Gly Thr<br>465                        470                        475                  480 | 1440 |
| tcc acc cat ctt ttt gct gtc ttc caa ggt cta ctt aag gtt ctt gct<br>Ser Thr His Leu Phe Ala Val Phe Gln Gly Leu Leu Lys Val Leu Ala<br>                  485                        490                        495 | 1488 |
| ggt atc aac acc aac ttc acc gtt aca tct aaa gcc aca aac aaa aat<br>Gly Ile Asn Thr Asn Phe Thr Val Thr Ser Lys Ala Thr Asn Lys Asn<br>                  500                        505                        510 | 1536 |
| ggg gat ttt gca aaa ctc tac atc ttc aaa tgg aca gct ctt ctc att<br>Gly Asp Phe Ala Lys Leu Tyr Ile Phe Lys Trp Thr Ala Leu Leu Ile<br>         515                        520                        525 | 1584 |
| cca cca acc acc gtc cta ctt gtg aac ctc ata ggc att gtg gct ggt<br>Pro Pro Thr Thr Val Leu Leu Val Asn Leu Ile Gly Ile Val Ala Gly<br>         530                        535                        540 | 1632 |
| gtc tct tat gct gta aac agt ggc tac cag tcg tgg ggt ccg ctt ttc<br>Val Ser Tyr Ala Val Asn Ser Gly Tyr Gln Ser Trp Gly Pro Leu Phe<br>545                        550                        555                  560 | 1680 |
| ggg aag ctc ttc ttc gcc tta tgg gtt att gcc cat ctc tac cct ttc<br>Gly Lys Leu Phe Phe Ala Leu Trp Val Ile Ala His Leu Tyr Pro Phe<br>                  565                        570                        575 | 1728 |
| ttg aaa ggt ctg ttg gga aga caa aac cga aca cca acc atc gtc att<br>Leu Lys Gly Leu Leu Gly Arg Gln Asn Arg Thr Pro Thr Ile Val Ile<br>                  580                        585                        590 | 1776 |
| gtc tgg tct gtt ctt ctc gcc tcc atc ttc tcg ttg ctt tgg gtc agg<br>Val Trp Ser Val Leu Leu Ala Ser Ile Phe Ser Leu Leu Trp Val Arg<br>         595                        600                        605 | 1824 |
| atc aat ccc ttt gtg gac gcc aat ccc aat gcc aac aac ttc aat ggc<br>Ile Asn Pro Phe Val Asp Ala Asn Pro Asn Ala Asn Asn Phe Asn Gly<br>         610                        615                        620 | 1872 |
| aaa gga ggt gtc ttt tagaccctat ttatatactt gtgtgtgcat atatcaaaaa<br>Lys Gly Gly Val Phe<br>625 | 1927 |
| cgcgcaatgg gaattccaaa tcatctaaac ccatcaaacc ccagtgaacc gggcagttaa | 1987 |

```
ggtgattcca tgtccaagat tagctttctc cgagtagcca gagaaggtga aattgttcgt   2047
aacactattg taatgatttt ccagtgggga agaagatgtg gacccaaatg atacatagtc   2107
tacaaaaaga attagttata actttcttat atttatttta tttaaagctt gttagactca   2167
cacttatgta atgttggaac ttgttgtcct aaaaagggat tggagttttc tttttatcta   2227
agaatctgaa gtttatatgc t                                              2248
```

<210> SEQ ID NO 2
<211> LENGTH: 629
<212> TYPE: PRT
<213> ORGANISM: Arabidopsis thaliana

<400> SEQUENCE: 2

```
Arg Ala Met Lys Arg Glu Tyr Glu Glu Phe Lys Val Arg Ile Asn Ala
  1               5                  10                  15

Leu Val Ala Lys Ala Gln Lys Ile Pro Gly Gly Trp Thr Met Gln
             20                  25                  30

Asp Gly Thr Pro Trp Pro Gly Asn Asn Thr Arg Asp His Pro Gly Met
         35                  40                  45

Ile Gln Val Phe Leu Gly His Ser Gly Gly Leu Asp Thr Asp Gly Asn
     50                  55                  60

Glu Leu Pro Arg Leu Ile Tyr Val Ser Arg Glu Lys Arg Pro Gly Phe
 65                  70                  75                  80

Gln His His Lys Lys Ala Gly Ala Met Asn Ala Ser Ile Arg Val Ser
                 85                  90                  95

Ala Val Leu Thr Asn Gly Ala Tyr Leu Leu Asn Val Asp Cys Asp His
            100                 105                 110

Tyr Phe Asn Asn Ser Lys Ala Ile Lys Glu Ala Met Cys Phe Met Met
        115                 120                 125

Asp Pro Ala Ile Gly Lys Lys Cys Cys Tyr Val Gln Phe Pro Gln Arg
    130                 135                 140

Phe Asp Gly Ile Asp Leu His Asp Arg Tyr Ala Asn Arg Asn Ile Val
145                 150                 155                 160

Phe Phe Asp Ile Asn Met Lys Gly Leu Asp Gly Ile His Gly Pro Val
                165                 170                 175

Tyr Val Gly Thr Gly Cys Cys Phe Asn Arg Gln Ala Leu Tyr Gly Tyr
            180                 185                 190

Asp Pro Val Leu Thr Glu Glu Asp Leu Glu Pro Asn Ile Ile Val Lys
        195                 200                 205

Ser Cys Cys Gly Ser Arg Lys Lys Gly Lys Ser Ser Lys Lys Tyr Asn
    210                 215                 220

Tyr Glu Lys Arg Arg Gly Ile Asn Arg Ser Asp Ser Asn Ala Pro Leu
225                 230                 235                 240

Phe Asn Met Glu Asp Ile Asp Glu Gly Phe Gly Tyr Asp Asp Glu
                245                 250                 255

Arg Ser Ile Leu Met Ser Gln Ser Val Glu Lys Arg Phe Gly Gln
            260                 265                 270

Ser Pro Val Phe Ile Ala Ala Thr Phe Met Glu Gln Gly Gly Ile Pro
        275                 280                 285

Pro Thr Thr Asn Pro Ala Thr Leu Leu Lys Glu Ala Ile His Val Ile
    290                 295                 300

Ser Cys Gly Tyr Glu Asp Lys Thr Glu Trp Gly Lys Glu Ile Gly Trp
305                 310                 315                 320
```

```
Ile Tyr Gly Ser Val Thr Glu Asp Ile Leu Thr Gly Phe Lys Met His
                325                 330                 335

Ala Arg Gly Trp Ile Ser Ile Tyr Cys Asn Pro Arg Pro Ala Phe
            340                 345                 350

Lys Gly Ser Ala Pro Ile Asn Leu Ser Asp Arg Leu Asn Gln Val Leu
        355                 360                 365

Arg Trp Ala Leu Gly Ser Ile Glu Ile Leu Ser Arg His Cys Pro
370                 375                 380

Ile Trp Tyr Gly Tyr His Gly Arg Leu Arg Leu Glu Arg Ile Ala
385                 390                 395                 400

Tyr Ile Asn Thr Ile Val Tyr Pro Ile Thr Ser Ile Pro Leu Ile Ala
                405                 410                 415

Tyr Cys Ile Leu Pro Ala Phe Cys Leu Ile Thr Asp Arg Phe Ile Ile
                420                 425                 430

Pro Glu Ile Ser Asn Tyr Ala Ser Ile Trp Phe Ile Leu Leu Phe Ile
                435                 440                 445

Ser Ile Ala Val Thr Gly Ile Leu Lys Leu Lys Trp Asn Gly Val Ser
        450                 455                 460

Ile Glu Asp Trp Trp Arg Asn Asn Gln Phe Trp Val Ile Gly Gly Thr
465                 470                 475                 480

Ser Thr His Leu Phe Ala Val Phe Gln Gly Leu Leu Lys Val Leu Ala
                485                 490                 495

Gly Ile Asn Thr Asn Phe Thr Val Thr Ser Lys Ala Thr Asn Lys Asn
                500                 505                 510

Gly Asp Phe Ala Lys Leu Tyr Ile Phe Lys Trp Thr Ala Leu Leu Ile
        515                 520                 525

Pro Pro Thr Thr Val Leu Leu Val Asn Leu Ile Gly Ile Val Ala Gly
        530                 535                 540

Val Ser Tyr Ala Val Asn Ser Gly Tyr Gln Ser Trp Gly Pro Leu Phe
545                 550                 555                 560

Gly Lys Leu Phe Phe Ala Leu Trp Val Ile Ala His Leu Tyr Pro Phe
                565                 570                 575

Leu Lys Gly Leu Leu Gly Arg Gln Asn Arg Thr Pro Thr Ile Val Ile
            580                 585                 590

Val Trp Ser Val Leu Leu Ala Ser Ile Phe Ser Leu Leu Trp Val Arg
        595                 600                 605

Ile Asn Pro Phe Val Asp Ala Asn Pro Asn Ala Asn Asn Phe Asn Gly
610                 615                 620

Lys Gly Gly Val Phe
625

<210> SEQ ID NO 3
<211> LENGTH: 8411
<212> TYPE: DNA
<213> ORGANISM: Arabidopsis thaliana

<400> SEQUENCE: 3
ttagaagaag cctgagccgg agtcctattc aattatctag aagaagtctg agccggagtc      60
ccactcgatt gtctaggaga agcctaagcc ggagtcccat tcgatcacct aggaagagtg     120
tgagcaggag tccagtccga tcatctagga agagtgtgag cagaagtccg gttcgttcat     180
ccaggagacg tatcagcagg agtccagtcc gatcatctag gaagagtgtg agcaggagtc     240
ctattcgatt gtccagaaga agtatcagca ggagtcctat tcgattgtcc aggagaagta     300
tcagcaggag tcctgttaga ggaagaagaa gaattagcag aagtccagtt ccggcaagga     360
```

| | |
|---|---|
| gaaggagtgt gcggcctaga tctcctcctc ctgaccgcag aagaagtttg tcaagaagtg | 420 |
| cttctcctaa tgggcgcata aggagaggga gaggatttag ccaaagattc tcatacgccc | 480 |
| gtcgatacag aactagtcca tctcctgatc gatctcctta tcgctttagt gataggagtg | 540 |
| accgtgacag gtgaatagcc cacacataat ataactcccc ctttctgtta cacactctcg | 600 |
| tactgaaccg tctttttttat aacgtcttct ctgtagattt agaagtcgca gaaggttctc | 660 |
| gccaagtcgg ttcagaagcc cactaagagg aagaacacct ccaaggtact tatcctcttt | 720 |
| agtacattgt ttcagctgat tctttacatc taaaagtttc atgaatatgg aactaaaatt | 780 |
| ggtgatccaa aagaattatt cttgatttca caactcgaaa gtatgctcag gtatagaaga | 840 |
| agaagccgct cagtatcgcc tggtctctgt tatcgcaacc ggcggtacag ccgcagccct | 900 |
| atccgtagcc gatctccacc ttacagaaag agaaggtcac catccgctag ccacagcctg | 960 |
| agtccatcga ggtcaagatc aagatcaaag tcatattcaa aatctcccat gggacgggg | 1020 |
| aaagcaagat cagtgtcaag atcaccatcc aaggcaaggt ctccatcgaa gtcggattcg | 1080 |
| acatcctcgg ataatagccc aggtgggaaa agggattag tagcctatga ttaatgaata | 1140 |
| atgattaccc ttaagttaag tgtttgttct ttttactgag aagagatggt aaagagagta | 1200 |
| agtagtttac ttctgtaaaa cataagcatt gtcttttgcg tatgtttgtt tgattatgct | 1260 |
| ccaagattgt taaaaatttc tgttgatgtt tgccgacatt ttttctttgt tgccatttgc | 1320 |
| cgacaaatgt taacttccat tattcgttgc ggagttggtt ttggtccaat aattaaactt | 1380 |
| tcataaaatt aagcataact aaatgtgacg tttgtcacca aactttagaa caacgacatc | 1440 |
| gtaatttatt tatttggata atcaatataa tttacgattt cttcctacat atatatcata | 1500 |
| tcactatacc accgtcatta tcactatcac taaatataaa aatgttaaaa tgatttctta | 1560 |
| atggaatttt ttttgttaaa agtttattga cacaaaaaat gaattaaaac tcagaaatct | 1620 |
| gtatactgaa ttaaaacttg taaatataac aacaaaatgg gattaaaaaa agaagtggca | 1680 |
| tccatttaaa aattatttgc gaattcgccc gtaacttctt aagctaacaa ttagaaccta | 1740 |
| atcaacacta gttattttga gtccaccgac aggtgatagc aaataaaaaa gaacaggctg | 1800 |
| gtaccagagc caacaacaac gtggcttctt cttttttttt tttaatataa tcaaacaatc | 1860 |
| atactttgtc ctatctcttt cttgcaataa gattttgcca cgtcacatac taagaagctg | 1920 |
| gcgcgtctag tggggaagcc agaacggctc actttaaaaa gtagagagat gataacttga | 1980 |
| gccgaataga gccgagctga gctaaaacgg tgggagagga agaggctact actaccgtca | 2040 |
| ccatctccgg taaataatg tacttgtcat ttaaaaatta agaaaaaaca catcactctg | 2100 |
| cgataaaata ggcaaaagca gatttgaaga agaagcagct tgagatatca aatagagaga | 2160 |
| gagagtgaca gaggagtgtg tgaacatcct tttttagtag atttgggttt tcgagatgcc | 2220 |
| gtattgaatc ggctacgaat tcccaatttt tgaattttgt gaatctctct ctttctctgt | 2280 |
| gtgtcggtgg ctgcgatgga ggccagtgcc ggcttggttg ctggatccta ccggagaaac | 2340 |
| gagctcgttc ggatccgaca tgaatctgat ggcggggtct gttcatcttc ccttttttccc | 2400 |
| attttttttgt tattgttttt cgttcttaca atttttgatg tgtagatctc atctagattt | 2460 |
| ctctgtttct aaatctcgtc tcttttggat ccataattgg atcattgaaa ctcagatttc | 2520 |
| gcttcctttg actgtgtagt tagttagtgt cagttgatca agtaagtgtc tgaaaatgga | 2580 |
| aacttttctg ctccaattct tcaaattgtt gtgatctata tcaattaatg ccgcatctgt | 2640 |
| tttcttaaaa tctcttatgg aaagtgtcgg tggatttcag ttcgttaact ttttaagct | 2700 |

-continued

| | |
|---|---|
| aaaatctttg actcttaaag tttagcttta cttattgaga tttagctcaa ctagatctcg | 2760 |
| ttagttcccg ccatgggata cagactgtga ctcgccttaa ttcagatctg cattgattgt | 2820 |
| tttgatttag atccttgctc atctctttct gtagtttcta atactcaatg actaacaatg | 2880 |
| atgcaatgtt ggtcaaagtg cagaccaaac ctttgaagaa tatgaatggc cagatatgtc | 2940 |
| agatctgtgg tgatgatgtt ggactcgctg aaactggaga tgtctttgtc gcgtgtaatg | 3000 |
| aatgtgcctt ccctgtgtgt cggccttgct atgagtacga gaggaaagat ggaactcagt | 3060 |
| gttgccctca atgcaagact agattcagac gacacagggg tcagttgtct ttttcttttt | 3120 |
| gttggcaatt gctatatatg gattttctct ttttgtttct ttgctgttgt gttgaacaat | 3180 |
| tttttggaat tttccaggga gtcctcgtgt tgaaggagat gaagatgagg atgatgttga | 3240 |
| tgatatcgag aatgagttca attacgccca gggagctaac aaggcgagac accaacgcca | 3300 |
| tggcgaagag ttttcttctt cctctagaca tgaatctcaa ccaattcctc ttctcaccca | 3360 |
| tggccatacg gtagggacct acatttttccc tttagactct agagtgattt gtattactca | 3420 |
| ataaatccct agagtggtca tttattactt actattcacg ttaatgttat atgtgaacaa | 3480 |
| atcttaacag aattttttc tgatagtaca tggtcatcca aattaagaaa taataataga | 3540 |
| tgttgttagt tgtgtctgtt ttcaatagat tcatgacctt tttctataca caggtttctg | 3600 |
| gagagattcg cacgcctgat acacaatctg tgcgaactac atcaggtcct ttgggtcctt | 3660 |
| ctgacaggaa tgctatttca tctccatata ttgatccacg gcaacctggt attcatatgt | 3720 |
| ttttcccttg tgcacgtggt ctttgttaaa tgtgattcct attcatttt acaacatata | 3780 |
| tattttgtgt accgtaactg atagctcccg ctaaaaattg cagtccctgt aagaatcgtg | 3840 |
| gacccgtcaa aagacttgaa ctcttatggg cttggtaatg ttgactggaa agaaagagtt | 3900 |
| gaaggctgga agctgaagca ggagaaaaat atgttacaga tgactggtaa ataccatgaa | 3960 |
| gggaaaggag gagaaattga agggactggt tccaatggcg aagaactcca aatgtaagtg | 4020 |
| gaaatactag accaatatct ttattgtcca actcaaacag ctcttggccg tgatgctaat | 4080 |
| aaccactctt ggtttcttat tatgtattga tagacataat taagtatctg ctttgttaca | 4140 |
| tttgtttcct tccactcaat tatggttctc gtacttacag ggctgatgat acacgtcttc | 4200 |
| ctatgagtcg tgtggtgcct atcccatctt ctcgcctaac cccttatcgg ttgtgatta | 4260 |
| ttctccggct tatcatcttg tgtttcttct tgcaatatcg tacaactcac cctgtgaaaa | 4320 |
| atgcatatcc tttgtggttg acctcggtta tctgtgagat ctggtttgca ttttcttggc | 4380 |
| ttcttgatca gtttcccaaa tggtaccccca ttaacaggga gacttatctt gaccgtctcg | 4440 |
| ctataaggtt ggtctttaag tttatacatc ccctactctc atctctcttt tatgtattaa | 4500 |
| cttgatatct tctatcacag ttttcgatag ttgactttt ccccctgtaa atttaattta | 4560 |
| aatttagaca atggtgcatc tgaatttga ttatgatata tcttaagaag attatgattg | 4620 |
| taaatcttga aatttagtag aaaaccatct gcaatctact gaccatgtga agtttccgac | 4680 |
| tagactatga tagaagcatg ccaagtggag tgtttattaa gatagagctt agctattata | 4740 |
| ctgattttat atgtgttttg attttttggt ttcttattgt agatatgatc gagacggtga | 4800 |
| accatcacag ctcgttcctg ttgatgtgtt tgttagtaca gtggacccat tgaaagagcc | 4860 |
| tccccttgtt acagcaaaca cagttctctc gattcttct gtggactacc cggtagataa | 4920 |
| agtagcctgt tatgtttcag atgatggttc agctatgctt acctttgaat cccttctga | 4980 |
| aaccgctgag tttgcaaaga aatgggtacc attttgcaag aaattcaaca ttgaacctag | 5040 |
| ggcccctgaa ttctattttg cccagaagat agattacttg aaggacaaga tccaaccgtc | 5100 |

-continued

```
ttttgttaaa gagcgacgag ctatgaaggt catttgaaaa gtccacctgc ttctcatcca    5160
tacggcaaag agattgactg acttttttctt tggtttgtat tgacagagag agtatgaaga    5220
gtttaaagtg aggataaatg ctcttgttgc caaagcacag aaaatccctg aagaaggctg    5280
gacaatgcag gatggtactc cctggcctgg taacaacact agagatcatc ctggaatgat    5340
acaggtacag tgtggcaatc ccttgattgt gacagagagg ataacgtaaa ggaaacatgt    5400
ttacatcgtt ttgttttcaat ttcaggtgtt cttaggccat agtggggggtc tggataccga    5460 tggaaatgag ctgcctagac tcatctatgt ttctcgtgaa aagcggcctg gatttcaaca    5520
ccacaaaaag gctggagcta tgaatgcatt ggtttgttaa ctttcagaat cctattgtgt    5580
cctctatttt attctcttgt tcactgccta agaaacgttc ttcttgtgta gccgttgctt    5640
cacattcttt tttttctagg ctatgtgttc tctcctaatt tagtatctct ttactttgac    5700
agatccgtgt atctgctgtt cttaccaatg gagcatatct tttgaacgtg gattgtgatc    5760
attactttaa taacagtaag gctattaaag aagctatgtg tttcatgatg gacccggcta    5820
ttggaaagaa gtgctgctat gtccagttcc ctcaacgttt tgacggtatt gatttgcacg    5880
atcgatatgc caacaggaat atagtctttt tcgatgtgag tatcacttcc ccattgtctt    5940
ttgtttctct tttgttcata ttttggttgg atttactcgt ttctgctatg gcctgacttg    6000
gatatttgtt ctcttgggca gattaacatg aaggggttgg atggtatcca gggtccagta    6060
tatgtgggta ctgttgttg ttttaatagg caggctctat atgggtatga tcctgttttg    6120
acggaagaag atttagaacc aaatattatt gtcaagagct gttgcgggtc aaggaagaaa    6180
ggtaaaagta gcaagaagta taactacgaa aagaggagag gcatcaacag aagtgactcc    6240
aatgctccac ttttcaatat ggaggacatc gatgagggtt ttgaaggttt gattgagctg    6300
attgtgtaat aacatcactt cttttatgtaa tgatttatgt gatggtgaaa tcttacaatc    6360
cttgtttatg caggttatga tgatgagagg tctattctaa tgtcccagag gagtgtagag    6420
aagcgttttg gtcagtcgcc ggtatttatt gcggcaacct tcatggaaca aggcggcatt    6480
ccaccaacaa ccaatcccgc tactcttctg aaggaggcta ttcatgttat aagctgtggt    6540
tacgaagaca agactgaatg gggcaaagag gtcagttttc aaatgcagct acagaatctt    6600
cttatgttct cttttcttacc tgtttgatga catcttattt ggcacttttg ttagattggt    6660
tggatctatg gttccgtgac ggaagatatt cttactgggt tcaagatgca tgcccgggt    6720 tggatatcga tctactgcaa tcctccacgc cctgcgttca agggatctgc accaatcaat    6780
ctttctgatc gtttgaacca agttcttcga tgggctttgg gatctatcga gattcttctt    6840
agcagacatt gtcctatctg gtatggttac catggaaggt tgagactttt ggagaggatc    6900
gcttatatca acaccatcgt ctatcctatt acatccatcc ctcttattgc gtattgtatt    6960
cttcccgctt tttgtctcat caccgacaga ttcatctac ccgaggtttg taaaactgac    7020
cacactgcta tttactattt gaatcccatt ttgtgaatgc atttttttgt catcatcatt    7080
gttgcagata agcaactacg cgagtatttg gttcattcta ctcttcatct caattgctgt    7140
gactggaatc ctggagctga gatggagcgg tgtgagcatt gaggattggt ggaggaacga    7200
gcagttctgg gtcattggtg gcacatccgc ccatctttt gctgtcttcc aagtctact    7260 taaggttctt gctggtatcg acaccaactt caccgttaca tctaaagcca cagacgaaga    7320
tggggatttt gcagaactct acatcttcaa atggacagct cttctcattc caccaaccac    7380
cgtcctactt gtgaacctca taggcattgt ggctggtgtc tcttatgctg taaacagtgg    7440
```

-continued

```
ctaccagtcg tggggtccgc ttttcgggaa gctcttcttc gccttatggg ttattgccca    7500
tctctaccct ttcttgaaag gtctgttggg aagacaaaac cgaacaccaa ccatcgtcat    7560
tgtctggtct gttcttctcg cctccatctt ctcgttgctt tgggtcagga tcaatccctt    7620
tgtggacgcc aatcccaatg ccaacaactt caatggcaaa ggaggtgtct tttagaccct    7680
atttatatac ttgtgtgtgc atatatcaaa acgcgcaat gggaattcca atcatctaa     7740 acccatcaaa ccccagtgaa ccgggcagtt aaggtgattc catgtccaag attagctttc    7800
tccgagtagc cagagaaggt gaaattgttc gtaacactat tgtaatgatt ttccagtggg    7860
gaagaagatg tggacccaaa tgatacatag tctacaaaaa gaatttgtta ttctttctta    7920
tatttatttt atttaaagct tgttagactc acacttatgt aatgttggaa cttgttgtcc    7980
taaaaaggga ttggagtttt cttttatct aagaatctga agtttatatg ctaagctttt     8040
cactttacta caaaagttt atggatatga tggtgtacgt caattgttgg tgcaagtgtt     8100
gatgtcttcg ggtgaactcg ccctcttgtt ttgtctcacc catcagtaca aatagaatga    8160
catttatttt tttgaacttt taacgaaatc tttgtcatta tgggacttga tcagtaaagt    8220
tacatatttg aagagatatt gtgtaaactc ttatttgaat cagaatcaga tcaatcaaaa    8280
attgaaaacg taaagttcaa acaaaaaggt agagtgaatc ttttaatccc ccctcaatac    8340
taatttgtga aatctcaagt ggtgtaaaat gaacccaatt agtatccaca atgtgtttct    8400
ctgatcaatc c                                                          8411

<210> SEQ ID NO 4
<211> LENGTH: 5009
<212> TYPE: DNA
<213> ORGANISM: Arabidopsis thaliana
<220> FEATURE:
<221> NAME/KEY: misc_feature
<222> LOCATION: (1)..(5009)
<223> OTHER INFORMATION: N is A, T, G or C.

<400> SEQUENCE: 4
aaggaataat aagataggg tttaatggga gacaatcaat cttcagggt tttctggaan        60 aacggcgggg taaaaaacaa gacatcaatc ggacccgatc acgaggaccc ggatccgnat     120
cgataaacag ngtagctttc aatacccccat tttcccagaa acacctctca aaaattttt    180 caagaactng tataaatatc tcagtttcgt tcacgcaggt cttnttatt ttggnaantc     240 tntnttcatn gttcaccaac tccctcttga aggtgggaca gagtccagct ccaccaccac    300
catagccatc gcgtcgtttt ctccgggacc cacttatttc gtgacgtttc tctctttgta    360
tatacataca attgtttttca gtctcaattt gctgtccaca ttttaacaca actctatctc    420
aggggtggtg tctgaatctc gtctctctca ttcctattta tcccaatcta atctatcaca    480 aaccttcca cattgctttt gtcagtctgt aaaattctct ttgaatcagt gaatcactca    540
cttaaatcca aaacagtttt ttttctttc tttctttatt tgcttgttgt ggaatcaata   600
gctgtctccg ggaaaattcg tttttttct ccttcgggat ctcttttttt ttttttttgg    660 ttttattaa taattatccc cgagccaaca tttattgtcg attcggttta tttcgtctcc    720
ttcgtcttcc actcttacta gtgcatgctc tgaatctgta tgtaatggga gttcaacagt    780
ctggatccat tatcctagcc gggtcgggtc aaggtctttg agtaagagag acaattcgtt    840
ttgattcggt gtagaagaca tcatgaatac tggtggtcgg ctcattgctg gctctcacaa    900
cagaaacgaa ttcgttctca ttaacgccga tgagagtgcc agagtaagaa taacttttgt    960
angaatttgt gacggaaaaa agtttaattt tttctctttc ttggggatct agattatgag   1020
```

```
aatctagatg gaatattttg atctgaaatt ggaagtttct agggagtaat gccgcaaccc    1080
acatgttctg ttttttcttt tttcttttct tcaagtagtg ttgcatgatt catacgtgtc    1140
ggcagagatg tcctgagaac cgaattcaat gttgtagcag tagcaataag ttcaaagaaa    1200
gtccattttt ttatattact aattctgttc ttggtttatt tgagctggtc tttattgcat    1260
ttcacctgga ttcagatact aataactgtc tcaattatgt aaaaatgaca actttatgaa    1320
attcagtttc acaattatgt aattcataat cgatgaatgt ttttcttgag tctttatcat    1380
ctttaggatt tgattaagat gcaatttgat gaaaatacta aaaagactca tgtgttctca    1440
tttctctatg tagatacgat cagtacaaga actgagtggg caaacatgtc aaatctgtgg    1500
agatgaaatc gaattaacgg ttagcagtga gctctttgtt gcttgcaacg aatgcgcatt    1560
cccggtttgt agaccatgct atgagtatga acgtagagaa ggaaatcaag cttgtcctca    1620
gtgcaaaact cgatacaaaa ggattaaagg tagtccacgg gttgatggag atgatgaaga    1680
agaagaagac attgatgatc ttgagtatga gtttgatcat gggatggacc ctgaacatgc    1740
cgctgaagcc gcactctctt cacgccttaa caccggtcgt ggtggattgg attcagctcc    1800
acctggctct cagattcctc ttttgactta ttgtgatgaa gtgaggaatc caaattgttt    1860
gttttctctg acaatgttgt tgcttagatg attcttttc ttattagtct atgtgttttc    1920
aggatgctga tatgtattct gatcgtcatg ctcttatcgt gcctccttca acgggatatg    1980
ggaatcgcgt ctatcctgca ccgtttacag attcttctgc acctcgtatg tgtttacttt    2040
tatgattcct acaattttc ttcttatatg atttggtcac cttctaatga gttatgaaat    2100
ggttttgttt gttgttttca gcacaggcga gatcaatggt tcctcagaaa gatattgcgg    2160
aatatggtta tggaagtgtt gcttggaagg accgtatgga agtttggaag agacgacaag    2220
gcgaaaagct tcaagtcatt aagcatgaag gaggaaacaa tggtcgaggt tccaatgatg    2280
acgacgaact agatgatcct gacatgccta tgtaagttgt taaaatctaa caaaagttca    2340
gatgaaatga tgctctgaaa ttttgtgttc aatggntttg ttttcttatt gttgtttaaa    2400 cattttcgt gctaattcag gatggatgaa ggaagacaac ctctctcaag aaagctacct    2460
attcgttcaa gcagaataaa tccttacagg atgttaattc tgtgtcgcct cgcgattctt    2520
ggtcttttct ttcattatag aattctccat ccagtcaatg atgcatatgg attatggtta    2580
acgtcagtta tatgcgagat atggtttgca gtgtcttgga ttcttgatca attccccaaa    2640
tggtatccta tagaacgtga acataccctc gatagactct ctctcaggta acataaaccc    2700
tgaaaagttc ttgtctgcaa atattcattt tttacattcc caaaaatttt tgaaactcta    2760
tttttcttac ataaggtacg agaaggaagg aaaaccgtca ggattagcac ctgttgatgt    2820
ttttgttagt acagtggatc cgttgaaaga gccacccttg attacagcaa acacagttct    2880
ttccattcta gcagttgatt atcctgtgga taaggttgcg tgttatgtat caaacaatgg    2940
tgcagctatg cttacatttg aagctctctc tgatacagct gagtttgcta gaaaatgggt    3000
tcctttttgt aagaagttta atatcgagcc acgagctcct gagtggtatt tttctcagaa    3060
gatggattac ctgaagaaca agttcatcc tgcttttgtc agggaacgtc gtgctatgaa    3120
ggttttcttt gctgcttttt ctctttctga gtatatccta tcataaaagt gttgtttcaa    3180
gaatctgatt tacgtttttt gcttgtttgt tgttgcaga gagattatga ggagtttaaa    3240
gtgaagataa atgcactggt tgctactgca cagaaagtgc ctgaggaagg ttggactatg    3300
caagatggaa ctccttggcc tggaaacaac gtccgtgacc atcctggaat gattcaggta    3360
```

-continued

```
atgatgagtt tgattgaata ggcaaaaaaa aagcggtttt tgtcctcttc actttgtttc      3420
cctggatctg ttaaattgga atgagcactc tacttctcaa tatatcttca gaccgaagcc      3480
tttttaagag attttgtaaa tgacaggtgt tcttgggtca tagtggagtt cgtgatacgg      3540
atggtaatga gttaccacgt ctagtgtatg tttctcgtga aagcggcct ggatttgatc       3600 accacaagaa agctggagct atgaattcct tggtaagtat aatgtgtttc tttatttatg      3660
aatctctctt ttcggagccc tgacttctca taaactaaaa ctcatcttac ttcttcttga      3720
agatccgagt ctctgctgtt ctatcaaacg ctccttacct tcttaatgtc gattgtgatc      3780
actacatcaa caacagcaaa gcaattagag aatctatgtg tttcatgatg acccgcaat      3840 cgggaaagaa agtttgttat gttcagtttc cgcagagatt tgatgggatt gatagacatg      3900
atagatactc aaaccgtaac gttgtgttct ttgatgtatg tgtccttatc tcttttgctt      3960
tgtttctgtt tatgttttag tgcttttcct cttttctcat ttgatattgt tttggtgtgg      4020
aaacagatta acatgaaagg tcttgatggg atacaaggac cgatatatgt cgggacaggt      4080
tgtgtgttta aaaacaggc tctttatggt tttgatgcac caagaagaa gaaaccacca       4140 ggcaaaacct gtaactgttg gcctaaatgg tgttgtttgt gttgtgggtt gagaaagaag      4200
agtaaaacga aagccaaaga taagaaaact aacactaaag agacttcaaa gcagattcat      4260
gcgctagaga atgtcgacga aggtgttatc gtcccaggta aaaaagaag gaaaaaaaa       4320 acatttctta tttggtttct gtcttgttga aagtctaagt agatccttt gattgttagt       4380 gtcaaatgtt gagaagagat ctgaagcaac acaattgaaa ttggagaaga agtttggaca      4440
atctccggtt ttcgttgcct ctgctgttct acagaacggt ggagttcccc gtaacgcaag      4500
ccccgcatgt ttgttaagag aagccattca agttattagc tgcgggtacg aagataaaac      4560
cgaatgggga aaagaggtag aaaacattac aaagttttc aacttctgaa actagaaaa        4620 gttcttgtga tctcattctt gctgataatc acacgcagat cgggtggatt tatggatcgg      4680
tgactgaaga tatcctgacg ggtttcaaga tgcattgcca tggatggaga tctgtgtact      4740
gtatgcctaa gcgtgcagct tttaaaggat ctgctcctat taacttgtca gatcgtcttc      4800
atcaagttct acgttgggct cttggctctg tagagatttt cttgagcaga cattgtccga      4860
tatggtatgg ttatggtggt ggtttaaaat ggttggagag attctcttac atcaactctg      4920
tcgtctatcc ttggacttca cttccattga tcgtctattg ttctctcccc gcggtttgtt      4980
tactcacagg aaaattcatc gtccctgag                                        5009
```

<210> SEQ ID NO 5
<211> LENGTH: 3603
<212> TYPE: DNA
<213> ORGANISM: Arabidopsis thaliana
<220> FEATURE:
<221> NAME/KEY: CDS
<222> LOCATION: (1)..(3243)

<400> SEQUENCE: 5

```
atg gag gcc agt gcc ggc ttg gtt gct gga tcc tac cgg aga aac gag        48
Met Glu Ala Ser Ala Gly Leu Val Ala Gly Ser Tyr Arg Arg Asn Glu
 1               5                  10                  15 ctc gtt cgg atc cga cat gaa tct gat ggc ggg acc aaa cct ttg aag        96
Leu Val Arg Ile Arg His Glu Ser Asp Gly Gly Thr Lys Pro Leu Lys
                 20                  25                  30 aat atg aat ggc cag ata tgt cag atc tgt ggt gat gat gtt gga ctc       144
Asn Met Asn Gly Gln Ile Cys Gln Ile Cys Gly Asp Asp Val Gly Leu
             35                  40                  45
```

```
gct gaa act gga gat gtc ttt gtc gcg tgt aat gaa tgt gcc ttc cct       192
Ala Glu Thr Gly Asp Val Phe Val Ala Cys Asn Glu Cys Ala Phe Pro
    50                  55                  60 gtg tgt cgg cct tgc tat gag tac gag agg aaa gat gga act cag tgt       240
Val Cys Arg Pro Cys Tyr Glu Tyr Glu Arg Lys Asp Gly Thr Gln Cys
 65                  70                  75                  80 tgc cct caa tgc aag act aga ttc aga cga cac agg ggg agt cct cgt       288
Cys Pro Gln Cys Lys Thr Arg Phe Arg Arg His Arg Gly Ser Pro Arg
                 85                  90                  95 gtt gaa gga gat gaa gat gag gat gat gtt gat gat atc gag aat gag       336
Val Glu Gly Asp Glu Asp Glu Asp Asp Val Asp Asp Ile Glu Asn Glu
                100                 105                 110 ttc aat tac gcc cag gga gct aac aag gcg aga cac caa cgc cat ggc       384
Phe Asn Tyr Ala Gln Gly Ala Asn Lys Ala Arg His Gln Arg His Gly
            115                 120                 125 gaa gag ttt tct tct tcc tct aga cat gaa tct caa cca att cct ctt       432
Glu Glu Phe Ser Ser Ser Ser Arg His Glu Ser Gln Pro Ile Pro Leu
130                 135                 140 ctc acc cat ggc cat acg gtt tct gga gag att cgc acg cct gat aca       480
Leu Thr His Gly His Thr Val Ser Gly Glu Ile Arg Thr Pro Asp Thr
145                 150                 155                 160 caa tct gtg cga act aca tca ggt cct ttg ggt cct tct gac agg aat       528
Gln Ser Val Arg Thr Thr Ser Gly Pro Leu Gly Pro Ser Asp Arg Asn
                165                 170                 175 gct att tca tct cca tat att gat cca cgg caa cct gtc cct gta aga       576
Ala Ile Ser Ser Pro Tyr Ile Asp Pro Arg Gln Pro Val Pro Val Arg
            180                 185                 190 atc gtg gac ccg tca aaa gac ttg aac tct tat ggg ctt ggt aat gtt       624
Ile Val Asp Pro Ser Lys Asp Leu Asn Ser Tyr Gly Leu Gly Asn Val
        195                 200                 205 gac tgg aaa gaa aga gtt gaa ggc tgg aag ctg aag cag gag aaa aat       672
Asp Trp Lys Glu Arg Val Glu Gly Trp Lys Leu Lys Gln Glu Lys Asn
    210                 215                 220 atg tta cag atg act ggt aaa tac cat gaa ggg aaa gga gga gaa att       720
Met Leu Gln Met Thr Gly Lys Tyr His Glu Gly Lys Gly Gly Glu Ile
225                 230                 235                 240 gaa ggg act ggt tcc aat ggc gaa gaa ctc caa atg gct gat gat aca       768
Glu Gly Thr Gly Ser Asn Gly Glu Glu Leu Gln Met Ala Asp Asp Thr
                245                 250                 255 cgt ctt cct atg agt cgt gtg gtg cct atc cca tct tct cgc cta acc       816
Arg Leu Pro Met Ser Arg Val Val Pro Ile Pro Ser Ser Arg Leu Thr
            260                 265                 270 cct tat cgg gtt gtg att att ctc cgg ctt atc atc ttg tgt ttc ttc       864
Pro Tyr Arg Val Val Ile Ile Leu Arg Leu Ile Ile Leu Cys Phe Phe
        275                 280                 285 ttg caa tat cgt aca act cac cct gtg aaa aat gca tat cct ttg tgg       912
Leu Gln Tyr Arg Thr Thr His Pro Val Lys Asn Ala Tyr Pro Leu Trp
    290                 295                 300 ttg acc tcg gtt atc tgt gag atc tgg ttt gca ttt tct tgg ctt ctt       960
Leu Thr Ser Val Ile Cys Glu Ile Trp Phe Ala Phe Ser Trp Leu Leu
305                 310                 315                 320 gat cag ttt ccc aaa tgg tac ccc att aac agg gag act tat ctt gac      1008
Asp Gln Phe Pro Lys Trp Tyr Pro Ile Asn Arg Glu Thr Tyr Leu Asp
                325                 330                 335 cgt ctc gct ata aga tat gat cga gac ggt gaa cca tca cag ctc gtt      1056
Arg Leu Ala Ile Arg Tyr Asp Arg Asp Gly Glu Pro Ser Gln Leu Val
            340                 345                 350 cct gtt gat gtg ttt gtt agt aca gtg gac cca ttg aaa gag cct ccc      1104
Pro Val Asp Val Phe Val Ser Thr Val Asp Pro Leu Lys Glu Pro Pro
        355                 360                 365
```

```
ctt gtt aca gca aac aca gtt ctc tcg att ctt tct gtg gac tac ccg    1152
Leu Val Thr Ala Asn Thr Val Leu Ser Ile Leu Ser Val Asp Tyr Pro
        370                 375                 380 gta gat aaa gta gcc tgt tat gtt tca gat gat ggt tca gct atg ctt    1200
Val Asp Lys Val Ala Cys Tyr Val Ser Asp Asp Gly Ser Ala Met Leu
385                 390                 395                 400 acc ttt gaa tcc ctt tct gaa acc gct gag ttt gca aag aaa tgg gta    1248
Thr Phe Glu Ser Leu Ser Glu Thr Ala Glu Phe Ala Lys Lys Trp Val
            405                 410                 415 cca ttt tgc aag aaa ttc aac att gaa cct agg gcc cct gaa ttc tat    1296
Pro Phe Cys Lys Lys Phe Asn Ile Glu Pro Arg Ala Pro Glu Phe Tyr
                420                 425                 430 ttt gcc cag aag ata gat tac ttg aag gac aag atc caa ccg tct ttt    1344
Phe Ala Gln Lys Ile Asp Tyr Leu Lys Asp Lys Ile Gln Pro Ser Phe
        435                 440                 445 gtt aaa gag cga cga gct atg aag aga gag tat gaa gag ttt aaa gtg    1392
Val Lys Glu Arg Arg Ala Met Lys Arg Glu Tyr Glu Glu Phe Lys Val
450                 455                 460 agg ata aat gct ctt gtt gcc aaa gca cag aaa atc cct gaa gaa ggc    1440
Arg Ile Asn Ala Leu Val Ala Lys Ala Gln Lys Ile Pro Glu Glu Gly
465                 470                 475                 480 tgg aca atg cag gat ggt act ccc tgg cct ggt aac aac act aga gat    1488
Trp Thr Met Gln Asp Gly Thr Pro Trp Pro Gly Asn Asn Thr Arg Asp
            485                 490                 495 cat cct gga atg ata cag gtg ttc tta ggc cat agt ggg ggt ctg gat    1536
His Pro Gly Met Ile Gln Val Phe Leu Gly His Ser Gly Gly Leu Asp
                500                 505                 510 acc gat gga aat gag ctg cct aga ctc atc tat gtt tct cgt gaa aag    1584
Thr Asp Gly Asn Glu Leu Pro Arg Leu Ile Tyr Val Ser Arg Glu Lys
        515                 520                 525 cgg cct gga ttt caa cac cac aaa aag gct gga gct atg aat gca ttg    1632
Arg Pro Gly Phe Gln His His Lys Lys Ala Gly Ala Met Asn Ala Leu
530                 535                 540 atc cgt gta tct gct gtt ctt acc aat gga gca tat ctt ttg aac gtg    1680
Ile Arg Val Ser Ala Val Leu Thr Asn Gly Ala Tyr Leu Leu Asn Val
545                 550                 555                 560 gat tgt gat cat tac ttt aat aac agt aag gct att aaa gaa gct atg    1728
Asp Cys Asp His Tyr Phe Asn Asn Ser Lys Ala Ile Lys Glu Ala Met
            565                 570                 575 tgt ttc atg atg gac ccg gct att gga aag aag tgc tgc tat gtc cag    1776
Cys Phe Met Met Asp Pro Ala Ile Gly Lys Lys Cys Cys Tyr Val Gln
                580                 585                 590 ttc cct caa cgt ttt gac ggt att gat ttg cac gat cga tat gcc aac    1824
Phe Pro Gln Arg Phe Asp Gly Ile Asp Leu His Asp Arg Tyr Ala Asn
        595                 600                 605 agg aat ata gtc ttt ttc gat att aac atg aag ggg ttg gat ggt atc    1872
Arg Asn Ile Val Phe Phe Asp Ile Asn Met Lys Gly Leu Asp Gly Ile
610                 615                 620 cag ggt cca gta tat gtg ggt act ggt tgt tgt ttt aat agg cag gct    1920
Gln Gly Pro Val Tyr Val Gly Thr Gly Cys Cys Phe Asn Arg Gln Ala
625                 630                 635                 640 cta tat ggg tat gat cct gtt ttg acg gaa gaa gat tta gaa cca aat    1968
Leu Tyr Gly Tyr Asp Pro Val Leu Thr Glu Glu Asp Leu Glu Pro Asn
            645                 650                 655 att att gtc aag agc tgt tgc ggg tca agg aag aaa ggt aaa agt agc    2016
Ile Ile Val Lys Ser Cys Cys Gly Ser Arg Lys Lys Gly Lys Ser Ser
                660                 665                 670 aag aag tat aac tac gaa aag agg aga ggc atc aac aga agt gac tcc    2064
Lys Lys Tyr Asn Tyr Glu Lys Arg Arg Gly Ile Asn Arg Ser Asp Ser
```

-continued

| | | 675 | | | | 680 | | | | 685 | | | | | |
|---|---|---|---|---|---|---|---|---|---|---|---|---|---|---|---|
| aat | gct | cca | ctt | ttc | aat | atg | gag | gac | atc | gat | gag | ggt | ttt | gaa | ggt | 2112 |
| Asn | Ala | Pro | Leu | Phe | Asn | Met | Glu | Asp | Ile | Asp | Glu | Gly | Phe | Glu | Gly | |
| | | 690 | | | | 695 | | | | 700 | | | | | |
| tat | gat | gat | gag | agg | tct | att | cta | atg | tcc | cag | agg | agt | gta | gag | aag | 2160 |
| Tyr | Asp | Asp | Glu | Arg | Ser | Ile | Leu | Met | Ser | Gln | Arg | Ser | Val | Glu | Lys | |
| 705 | | | | | 710 | | | | | 715 | | | | | 720 | |
| cgt | ttt | ggt | cag | tcg | ccg | gta | ttt | att | gcg | gca | acc | ttc | atg | gaa | caa | 2208 |
| Arg | Phe | Gly | Gln | Ser | Pro | Val | Phe | Ile | Ala | Ala | Thr | Phe | Met | Glu | Gln | |
| | | | | 725 | | | | | 730 | | | | | 735 | | |
| ggc | ggc | att | cca | cca | aca | acc | aat | ccc | gct | act | ctt | ctg | aag | gag | gct | 2256 |
| Gly | Gly | Ile | Pro | Pro | Thr | Thr | Asn | Pro | Ala | Thr | Leu | Leu | Lys | Glu | Ala | |
| | | | 740 | | | | | 745 | | | | | 750 | | | |
| att | cat | gtt | ata | agc | tgt | ggt | tac | gaa | gac | aag | act | gaa | tgg | ggc | aaa | 2304 |
| Ile | His | Val | Ile | Ser | Cys | Gly | Tyr | Glu | Asp | Lys | Thr | Glu | Trp | Gly | Lys | |
| | | | 755 | | | | | 760 | | | | | 765 | | | |
| gag | att | ggt | tgg | atc | tat | ggt | tcc | gtg | acg | gaa | gat | att | ctt | act | ggg | 2352 |
| Glu | Ile | Gly | Trp | Ile | Tyr | Gly | Ser | Val | Thr | Glu | Asp | Ile | Leu | Thr | Gly | |
| | | 770 | | | | | 775 | | | | | 780 | | | | |
| ttc | aag | atg | cat | gcc | cgg | ggt | tgg | ata | tcg | atc | tac | tgc | aat | cct | cca | 2400 |
| Phe | Lys | Met | His | Ala | Arg | Gly | Trp | Ile | Ser | Ile | Tyr | Cys | Asn | Pro | Pro | |
| 785 | | | | | 790 | | | | | 795 | | | | | 800 | |
| cgc | cct | gcg | ttc | aag | gga | tct | gca | cca | atc | aat | ctt | tct | gat | cgt | ttg | 2448 |
| Arg | Pro | Ala | Phe | Lys | Gly | Ser | Ala | Pro | Ile | Asn | Leu | Ser | Asp | Arg | Leu | |
| | | | | 805 | | | | | 810 | | | | | 815 | | |
| aac | caa | gtt | ctt | cga | tgg | gct | ttg | gga | tct | atc | gag | att | ctt | ctt | agc | 2496 |
| Asn | Gln | Val | Leu | Arg | Trp | Ala | Leu | Gly | Ser | Ile | Glu | Ile | Leu | Leu | Ser | |
| | | | 820 | | | | | 825 | | | | | 830 | | | |
| aga | cat | tgt | cct | atc | tgg | tat | ggt | tac | cat | gga | agg | ttg | aga | ctt | ttg | 2544 |
| Arg | His | Cys | Pro | Ile | Trp | Tyr | Gly | Tyr | His | Gly | Arg | Leu | Arg | Leu | Leu | |
| | | 835 | | | | | 840 | | | | | 845 | | | | |
| gag | agg | atc | gct | tat | atc | aac | acc | atc | gtc | tat | cct | att | aca | tcc | atc | 2592 |
| Glu | Arg | Ile | Ala | Tyr | Ile | Asn | Thr | Ile | Val | Tyr | Pro | Ile | Thr | Ser | Ile | |
| 850 | | | | | 855 | | | | | 860 | | | | | | |
| cct | ctt | att | gcg | tat | tgt | att | ctt | ccc | gct | ttt | tgt | ctc | atc | acc | gac | 2640 |
| Pro | Leu | Ile | Ala | Tyr | Cys | Ile | Leu | Pro | Ala | Phe | Cys | Leu | Ile | Thr | Asp | |
| 865 | | | | | 870 | | | | | 875 | | | | | 880 | |
| aga | ttc | atc | ata | ccc | gag | ata | agc | aac | tac | gcg | agt | att | tgg | ttc | att | 2688 |
| Arg | Phe | Ile | Ile | Pro | Glu | Ile | Ser | Asn | Tyr | Ala | Ser | Ile | Trp | Phe | Ile | |
| | | | | 885 | | | | | 890 | | | | | 895 | | |
| cta | ctc | ttc | atc | tca | att | gct | gtg | act | gga | atc | ctg | gag | ctg | aga | tgg | 2736 |
| Leu | Leu | Phe | Ile | Ser | Ile | Ala | Val | Thr | Gly | Ile | Leu | Glu | Leu | Arg | Trp | |
| | | | 900 | | | | | 905 | | | | | 910 | | | |
| agc | ggt | gtg | agc | att | gag | gat | tgg | tgg | agg | aac | gag | cag | ttc | tgg | gtc | 2784 |
| Ser | Gly | Val | Ser | Ile | Glu | Asp | Trp | Trp | Arg | Asn | Glu | Gln | Phe | Trp | Val | |
| | | 915 | | | | | 920 | | | | | 925 | | | | |
| att | ggt | ggc | aca | tcc | gcc | cat | ctt | ttt | gct | gtc | ttc | caa | ggt | cta | ctt | 2832 |
| Ile | Gly | Gly | Thr | Ser | Ala | His | Leu | Phe | Ala | Val | Phe | Gln | Gly | Leu | Leu | |
| | | 930 | | | | | 935 | | | | | 940 | | | | |
| aag | gtt | ctt | gct | ggt | atc | gac | acc | aac | ttc | acc | gtt | aca | tct | aaa | gcc | 2880 |
| Lys | Val | Leu | Ala | Gly | Ile | Asp | Thr | Asn | Phe | Thr | Val | Thr | Ser | Lys | Ala | |
| 945 | | | | | 950 | | | | | 955 | | | | | 960 | |
| aca | gac | gaa | gat | ggg | gat | ttt | gca | gaa | ctc | tac | atc | ttc | aaa | tgg | aca | 2928 |
| Thr | Asp | Glu | Asp | Gly | Asp | Phe | Ala | Glu | Leu | Tyr | Ile | Phe | Lys | Trp | Thr | |
| | | | | 965 | | | | | 970 | | | | | 975 | | |
| gct | ctt | ctc | att | cca | cca | acc | acc | gtc | cta | ctt | gtg | aac | ctc | ata | ggc | 2976 |
| Ala | Leu | Leu | Ile | Pro | Pro | Thr | Thr | Val | Leu | Leu | Val | Asn | Leu | Ile | Gly | |
| | | | 980 | | | | | 985 | | | | | 990 | | | |
| att | gtg | gct | ggt | gtc | tct | tat | gct | gta | aac | agt | ggc | tac | cag | tcg | tgg | 3024 |

-continued

```
Ile Val Ala Gly Val Ser Tyr Ala Val Asn Ser Gly Tyr Gln Ser Trp
    995                 1000                1005 ggt ccg ctt ttc ggg aag ctc ttc ttc gcc tta tgg gtt att gcc cat    3072
Gly Pro Leu Phe Gly Lys Leu Phe Phe Ala Leu Trp Val Ile Ala His
    1010                1015                1020 ctc tac cct ttc ttg aaa ggt ctg ttg gga aga caa aac cga aca cca    3120
Leu Tyr Pro Phe Leu Lys Gly Leu Leu Gly Arg Gln Asn Arg Thr Pro
1025                1030                1035                1040 acc atc gtc att gtc tgg tct gtt ctt ctc gcc tcc atc ttc tcg ttg    3168
Thr Ile Val Ile Val Trp Ser Val Leu Leu Ala Ser Ile Phe Ser Leu
                1045                1050                1055 ctt tgg gtc agg atc aat ccc ttt gtg gac gcc aat ccc aat gcc aac    3216
Leu Trp Val Arg Ile Asn Pro Phe Val Asp Ala Asn Pro Asn Ala Asn
            1060                1065                1070 aac ttc aat ggc aaa gga ggt gtc ttt tagaccctat ttatatactt          3263
Asn Phe Asn Gly Lys Gly Gly Val Phe
        1075                1080 gtgtgtgcat atatcaaaaa cgcgcaatgg gaattccaaa tcatctaaac ccatcaaacc  3323
ccagtgaacc gggcagttaa ggtgattcca tgtccaagat tagctttctc cgagtagcca  3383
gagaaggtga aattgttcgt aacactattg taatgatttt ccagtgggga agaagatgtg  3443
gacccaaatg atacatagtc tacaaaaaga atttgttatt ctttcttata tttatttat  3503 ttaaagcttg ttagactcac acttatgtaa tgttggaact tgttgtccta aaaagggatt  3563
ggagttttct ttttatctaa gaatctgaag tttatatgct                        3603

<210> SEQ ID NO 6
<211> LENGTH: 1081
<212> TYPE: PRT
<213> ORGANISM: Arabidopsis thaliana

<400> SEQUENCE: 6

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

Val Glu Gly Asp Glu Asp Glu Asp Val Asp Asp Ile Glu Asn Glu
            100                 105                 110

Phe Asn Tyr Ala Gln Gly Ala Asn Lys Ala Arg His Gln Arg His Gly
        115                 120                 125

Glu Glu Phe Ser Ser Ser Arg His Glu Ser Gln Pro Ile Pro Leu
    130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
            180                 185                 190
```

-continued

```
Ile Val Asp Pro Ser Lys Asp Leu Asn Ser Tyr Gly Leu Gly Asn Val
    195                 200                 205
Asp Trp Lys Glu Arg Val Glu Gly Trp Lys Leu Lys Gln Glu Lys Asn
    210                 215                 220
Met Leu Gln Met Thr Gly Lys Tyr His Glu Gly Lys Gly Gly Glu Ile
225                 230                 235                 240
Glu Gly Thr Gly Ser Asn Gly Glu Glu Leu Gln Met Ala Asp Asp Thr
                245                 250                 255
Arg Leu Pro Met Ser Arg Val Val Pro Ile Pro Ser Ser Arg Leu Thr
                260                 265                 270
Pro Tyr Arg Val Val Ile Ile Leu Arg Leu Ile Ile Leu Cys Phe Phe
                275                 280                 285
Leu Gln Tyr Arg Thr Thr His Pro Val Lys Asn Ala Tyr Pro Leu Trp
    290                 295                 300
Leu Thr Ser Val Ile Cys Glu Ile Trp Phe Ala Phe Ser Trp Leu Leu
305                 310                 315                 320
Asp Gln Phe Pro Lys Trp Tyr Pro Ile Asn Arg Glu Thr Tyr Leu Asp
                325                 330                 335
Arg Leu Ala Ile Arg Tyr Asp Arg Asp Gly Glu Pro Ser Gln Leu Val
                340                 345                 350
Pro Val Asp Val Phe Val Ser Thr Val Asp Pro Leu Lys Glu Pro Pro
                355                 360                 365
Leu Val Thr Ala Asn Thr Val Leu Ser Ile Leu Ser Val Asp Tyr Pro
    370                 375                 380
Val Asp Lys Val Ala Cys Tyr Val Ser Asp Asp Gly Ser Ala Met Leu
385                 390                 395                 400
Thr Phe Glu Ser Leu Ser Glu Thr Ala Glu Phe Ala Lys Lys Trp Val
                405                 410                 415
Pro Phe Cys Lys Lys Phe Asn Ile Glu Pro Arg Ala Pro Glu Phe Tyr
                420                 425                 430
Phe Ala Gln Lys Ile Asp Tyr Leu Lys Asp Lys Ile Gln Pro Ser Phe
                435                 440                 445
Val Lys Glu Arg Arg Ala Met Lys Arg Glu Tyr Glu Glu Phe Lys Val
    450                 455                 460
Arg Ile Asn Ala Leu Val Ala Lys Ala Gln Lys Ile Pro Glu Glu Gly
465                 470                 475                 480
Trp Thr Met Gln Asp Gly Thr Pro Trp Pro Gly Asn Asn Thr Arg Asp
                485                 490                 495
His Pro Gly Met Ile Gln Val Phe Leu Gly His Ser Gly Gly Leu Asp
                500                 505                 510
Thr Asp Gly Asn Glu Leu Pro Arg Leu Ile Tyr Val Ser Arg Glu Lys
                515                 520                 525
Arg Pro Gly Phe Gln His His Lys Lys Ala Gly Ala Met Asn Ala Leu
    530                 535                 540
Ile Arg Val Ser Ala Val Leu Thr Asn Gly Ala Tyr Leu Leu Asn Val
545                 550                 555                 560
Asp Cys Asp His Tyr Phe Asn Asn Ser Lys Ala Ile Lys Glu Ala Met
                565                 570                 575
Cys Phe Met Met Asp Pro Ala Ile Gly Lys Lys Cys Cys Tyr Val Gln
                580                 585                 590
Phe Pro Gln Arg Phe Asp Gly Ile Asp Leu His Asp Arg Tyr Ala Asn
                595                 600                 605
Arg Asn Ile Val Phe Phe Asp Ile Asn Met Lys Gly Leu Asp Gly Ile
```

-continued

```
            610                 615                 620
Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
                660                 665                 670

Lys Lys Tyr Asn Tyr Glu Lys Arg Arg Gly Ile Asn Arg Ser Asp Ser
                675                 680                 685

Asn Ala Pro Leu Phe Asn Met Glu Asp Ile Asp Glu Gly Phe Glu Gly
                690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735

Gly Gly Ile Pro Pro Thr Thr Asn Pro Ala Thr Leu Leu Lys Glu Ala
                740                 745                 750

Ile His Val Ile Ser Cys Gly Tyr Glu Asp Lys Thr Glu Trp Gly Lys
                755                 760                 765

Glu Ile Gly Trp Ile Tyr Gly Ser Val Thr Glu Asp Ile Leu Thr Gly
770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
                820                 825                 830

Arg His Cys Pro Ile Trp Tyr Gly Tyr His Gly Arg Leu Arg Leu Leu
                835                 840                 845

Glu Arg Ile Ala Tyr Ile Asn Thr Ile Val Tyr Pro Ile Thr Ser Ile
850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
                885                 890                 895

Leu Leu Phe Ile Ser Ile Ala Val Thr Gly Ile Leu Glu Leu Arg Trp
                900                 905                 910

Ser Gly Val Ser Ile Glu Asp Trp Trp Arg Asn Glu Gln Phe Trp Val
                915                 920                 925

Ile Gly Gly Thr Ser Ala His Leu Phe Ala Val Phe Gln Gly Leu Leu
                930                 935                 940

Lys Val Leu Ala Gly Ile Asp Thr Asn Phe Thr Val Thr Ser Lys Ala
945                 950                 955                 960

Thr Asp Glu Asp Gly Asp Phe Ala Glu Leu Tyr Ile Phe Lys Trp Thr
                965                 970                 975

Ala Leu Leu Ile Pro Pro Thr Thr Val Leu Leu Val Asn Leu Ile Gly
                980                 985                 990

Ile Val Ala Gly Val Ser Tyr Ala Val Asn Ser Gly Tyr Gln Ser Trp
                995                 1000                1005

Gly Pro Leu Phe Gly Lys Leu Phe Phe Ala Leu Trp Val Ile Ala His
                1010                1015                1020

Leu Tyr Pro Phe Leu Lys Gly Leu Leu Gly Arg Gln Asn Arg Thr Pro
1025                1030                1035                1040
```

```
Thr Ile Val Ile Val Trp Ser Val Leu Leu Ala Ser Ile Phe Ser Leu
            1045                1050                1055

Leu Trp Val Arg Ile Asn Pro Phe Val Asp Ala Asn Pro Asn Ala Asn
            1060                1065                1070

Asn Phe Asn Gly Lys Gly Gly Val Phe
            1075                1080

<210> SEQ ID NO 7
<211> LENGTH: 3828
<212> TYPE: DNA
<213> ORGANISM: Arabidopsis thaliana
<220> FEATURE:
<221> NAME/KEY: CDS
<222> LOCATION: (239)..(3490)

<400> SEQUENCE: 7
gtcgacacta agtggatcca aagaattcgc ggccgcgtcg atacggctgc gagaagacga      60 cagaaggga ttgtcgattc ggtttatttc gtctccttcg tcttccactc ttactagtgc     120
atgctctgaa tctgtatgta atgggagttc aacagtctgg atccattatc ctagccgggt     180
cgggtcaagg tctttgaata agagagacaa ttcgttttga ttcggtgtag aagacatc      238 atg aat act ggt ggt cgg ctc att gct ggc tct cac aac aga aac gaa      286
Met Asn Thr Gly Gly Arg Leu Ile Ala Gly Ser His Asn Arg Asn Glu
  1               5                  10                  15 ttc gtt ctc att aac gcc gat gag agt gcc aga ata cga tca gta caa      334
Phe Val Leu Ile Asn Ala Asp Glu Ser Ala Arg Ile Arg Ser Val Gln
             20                  25                  30 gaa ctg agt ggg caa aca tgt caa atc tgt gga gat gaa atc gaa tta      382
Glu Leu Ser Gly Gln Thr Cys Gln Ile Cys Gly Asp Glu Ile Glu Leu
         35                  40                  45 acg gtt agc agt gag ctc ttt gtt gct tgc aac gaa tgc gca ttc ccg      430
Thr Val Ser Ser Glu Leu Phe Val Ala Cys Asn Glu Cys Ala Phe Pro
     50                  55                  60 gtt tgt aga cca tgc tat gag tat gaa cgt aga gaa gga aat caa gct      478
Val Cys Arg Pro Cys Tyr Glu Tyr Glu Arg Arg Glu Gly Asn Gln Ala
 65                  70                  75                  80 tgt cct cag tgc aaa act cga tac aaa agg att aaa ggt agt cca cgg      526
Cys Pro Gln Cys Lys Thr Arg Tyr Lys Arg Ile Lys Gly Ser Pro Arg
                 85                  90                  95 gtt gat gga gat gat gaa gaa gaa gac att gat gat ctt gag tat          574
Val Asp Gly Asp Asp Glu Glu Glu Asp Ile Asp Asp Leu Glu Tyr
                100                 105                 110 gag ttt gat cat ggg atg gac cct gaa cat gcc gct gaa gcc gca ctc      622
Glu Phe Asp His Gly Met Asp Pro Glu His Ala Ala Glu Ala Ala Leu
            115                 120                 125 tct tca cgc ctt aac acc ggt cgt ggt gga ttg gat tca gct cca cct      670
Ser Ser Arg Leu Asn Thr Gly Arg Gly Gly Leu Asp Ser Ala Pro Pro
        130                 135                 140 ggc tct cag att cct ctt ttg act tat tgt gat gaa gat gct gat atg      718
Gly Ser Gln Ile Pro Leu Leu Thr Tyr Cys Asp Glu Asp Ala Asp Met
145                 150                 155                 160 tat tct gat cgt cat gct ctt atc gtg cct cct tca acg gga tat ggg      766
Tyr Ser Asp Arg His Ala Leu Ile Val Pro Pro Ser Thr Gly Tyr Gly
                165                 170                 175 aat cgc gtc tat cct gca ccg ttt aca gat tct tct gca cct cca cag      814
Asn Arg Val Tyr Pro Ala Pro Phe Thr Asp Ser Ser Ala Pro Pro Gln
            180                 185                 190 gcg aga tca atg gtt cct cag aaa gat att gcg gaa tat ggt tat gga      862
Ala Arg Ser Met Val Pro Gln Lys Asp Ile Ala Glu Tyr Gly Tyr Gly
```

-continued

| | | | | | | | | | | | | | | | |
|---|---|---|---|---|---|---|---|---|---|---|---|---|---|---|---|
| | | | 195 | | | | 200 | | | | 205 | | | | |
| agt | gtt | gct | tgg | aag | gac | cgt | atg | gaa | gtt | tgg | aag | aga | cga | caa | ggc | 910 |
| Ser | Val | Ala | Trp | Lys | Asp | Arg | Met | Glu | Val | Trp | Lys | Arg | Arg | Gln | Gly | |
| 210 | | | | 215 | | | | 220 | | | | | | | | |

| gaa | aag | ctt | caa | gtc | att | aag | cat | gaa | gga | gga | aac | aat | ggt | cga | ggt | 958 |
|---|---|---|---|---|---|---|---|---|---|---|---|---|---|---|---|---|
| Glu | Lys | Leu | Gln | Val | Ile | Lys | His | Glu | Gly | Gly | Asn | Asn | Gly | Arg | Gly | |
| 225 | | | | 230 | | | | 235 | | | | 240 | | | | |

| tcc | aat | gat | gac | gac | gaa | cta | gat | gat | cct | gac | atg | cct | atg | atg | gat | 1006 |
|---|---|---|---|---|---|---|---|---|---|---|---|---|---|---|---|---|
| Ser | Asn | Asp | Asp | Asp | Glu | Leu | Asp | Asp | Pro | Asp | Met | Pro | Met | Met | Asp | |
| | | | 245 | | | | | 250 | | | | 255 | | | | |

| gaa | gga | aga | caa | cct | ctc | tca | aga | aag | cta | cct | att | cgt | tca | agc | aga | 1054 |
|---|---|---|---|---|---|---|---|---|---|---|---|---|---|---|---|---|
| Glu | Gly | Arg | Gln | Pro | Leu | Ser | Arg | Lys | Leu | Pro | Ile | Arg | Ser | Ser | Arg | |
| | | | 260 | | | | | 265 | | | | 270 | | | | |

| ata | aat | cct | tac | agg | atg | tta | att | ctg | tgt | cgc | ctc | gcg | att | ctt | ggt | 1102 |
|---|---|---|---|---|---|---|---|---|---|---|---|---|---|---|---|---|
| Ile | Asn | Pro | Tyr | Arg | Met | Leu | Ile | Leu | Cys | Arg | Leu | Ala | Ile | Leu | Gly | |
| | | 275 | | | | | 280 | | | | | 285 | | | | |

| ctt | ttc | ttt | cat | tat | aga | att | ctc | cat | cca | gtc | aat | gat | gca | tat | gga | 1150 |
|---|---|---|---|---|---|---|---|---|---|---|---|---|---|---|---|---|
| Leu | Phe | Phe | His | Tyr | Arg | Ile | Leu | His | Pro | Val | Asn | Asp | Ala | Tyr | Gly | |
| | | 290 | | | | | 295 | | | | | 300 | | | | |

| tta | tgg | tta | acg | tca | gtt | ata | tgc | gaa | ata | tgg | ttt | gca | gtg | tct | tgg | 1198 |
|---|---|---|---|---|---|---|---|---|---|---|---|---|---|---|---|---|
| Leu | Trp | Leu | Thr | Ser | Val | Ile | Cys | Glu | Ile | Trp | Phe | Ala | Val | Ser | Trp | |
| 305 | | | | 310 | | | | 315 | | | | 320 | | | | |

| att | ctt | gat | caa | ttc | ccc | aaa | tgg | tat | cct | ata | gaa | cgt | gaa | aca | tac | 1246 |
|---|---|---|---|---|---|---|---|---|---|---|---|---|---|---|---|---|
| Ile | Leu | Asp | Gln | Phe | Pro | Lys | Trp | Tyr | Pro | Ile | Glu | Arg | Glu | Thr | Tyr | |
| | | | 325 | | | | | 330 | | | | 335 | | | | |

| ctc | gat | aga | ctc | tct | ctc | agg | tac | gag | aag | gaa | gga | aaa | ccg | tca | gga | 1294 |
|---|---|---|---|---|---|---|---|---|---|---|---|---|---|---|---|---|
| Leu | Asp | Arg | Leu | Ser | Leu | Arg | Tyr | Glu | Lys | Glu | Gly | Lys | Pro | Ser | Gly | |
| | | | 340 | | | | | 345 | | | | 350 | | | | |

| tta | gca | cct | gtt | gat | gtt | ttt | gtt | agt | aca | gtg | gat | ccg | ttg | aaa | gag | 1342 |
|---|---|---|---|---|---|---|---|---|---|---|---|---|---|---|---|---|
| Leu | Ala | Pro | Val | Asp | Val | Phe | Val | Ser | Thr | Val | Asp | Pro | Leu | Lys | Glu | |
| | | | 355 | | | | | 360 | | | | 365 | | | | |

| ccc | ccc | ttg | att | aca | gca | aac | aca | gtt | ctt | tcc | att | cta | gca | gtt | gat | 1390 |
|---|---|---|---|---|---|---|---|---|---|---|---|---|---|---|---|---|
| Pro | Pro | Leu | Ile | Thr | Ala | Asn | Thr | Val | Leu | Ser | Ile | Leu | Ala | Val | Asp | |
| | 370 | | | | | 375 | | | | | 380 | | | | | |

| tat | cct | gtg | gat | aag | gtt | gcg | tgt | tat | gta | tca | aac | aat | ggt | gca | gct | 1438 |
|---|---|---|---|---|---|---|---|---|---|---|---|---|---|---|---|---|
| Tyr | Pro | Val | Asp | Lys | Val | Ala | Cys | Tyr | Val | Ser | Asn | Asn | Gly | Ala | Ala | |
| 385 | | | | 390 | | | | 395 | | | | 400 | | | | |

| atg | ctt | aca | ttt | gaa | gct | ctc | tct | gat | aca | gct | gat | ttt | gct | aca | aaa | 1486 |
|---|---|---|---|---|---|---|---|---|---|---|---|---|---|---|---|---|
| Met | Leu | Thr | Phe | Glu | Ala | Leu | Ser | Asp | Thr | Ala | Asp | Phe | Ala | Thr | Lys | |
| | | | 405 | | | | | 410 | | | | 415 | | | | |

| tgg | gtt | cct | ttt | tgt | aag | aag | ttt | aat | atc | gag | cca | cga | gct | cct | gag | 1534 |
|---|---|---|---|---|---|---|---|---|---|---|---|---|---|---|---|---|
| Trp | Val | Pro | Phe | Cys | Lys | Lys | Phe | Asn | Ile | Glu | Pro | Arg | Ala | Pro | Glu | |
| | | | 420 | | | | | 425 | | | | 430 | | | | |

| tgg | tat | ttt | tct | cag | aag | atg | gat | tac | ctg | aag | aac | aaa | gtt | cat | cct | 1582 |
|---|---|---|---|---|---|---|---|---|---|---|---|---|---|---|---|---|
| Trp | Tyr | Phe | Ser | Gln | Lys | Met | Asp | Tyr | Leu | Lys | Asn | Lys | Val | His | Pro | |
| | | | 435 | | | | | 440 | | | | 445 | | | | |

| gct | ttt | gtc | agg | gaa | cgt | cgt | gct | atg | aag | aga | gat | tat | gaa | gag | ttt | 1630 |
|---|---|---|---|---|---|---|---|---|---|---|---|---|---|---|---|---|
| Ala | Phe | Val | Arg | Glu | Arg | Arg | Ala | Met | Lys | Arg | Asp | Tyr | Glu | Glu | Phe | |
| | | 450 | | | | | 455 | | | | | 460 | | | | |

| aaa | gtg | aag | ata | aat | gca | ctg | gtt | gct | act | gca | cag | aaa | gtg | cct | gag | 1678 |
|---|---|---|---|---|---|---|---|---|---|---|---|---|---|---|---|---|
| Lys | Val | Lys | Ile | Asn | Ala | Leu | Val | Ala | Thr | Ala | Gln | Lys | Val | Pro | Glu | |
| 465 | | | | 470 | | | | 475 | | | | 480 | | | | |

| gaa | cgt | tgg | act | atg | caa | gat | gga | act | cct | tgg | cct | gga | aac | aac | gtc | 1726 |
|---|---|---|---|---|---|---|---|---|---|---|---|---|---|---|---|---|
| Glu | Arg | Trp | Thr | Met | Gln | Asp | Gly | Thr | Pro | Trp | Pro | Gly | Asn | Asn | Val | |
| | | | 485 | | | | | 490 | | | | 495 | | | | |

| cgt | gac | cat | cct | gga | atg | att | cag | gtg | ttc | ttg | ggt | cat | agt | gga | gtt | 1774 |
|---|---|---|---|---|---|---|---|---|---|---|---|---|---|---|---|---|
| Arg | Asp | His | Pro | Gly | Met | Ile | Gln | Val | Phe | Leu | Gly | His | Ser | Gly | Val | |
| | | 500 | | | | | 505 | | | | | 510 | | | | | |

| cgt | gat | acg | gat | ggt | aat | gag | tta | cca | cgt | cta | gtg | tat | gtt | tct | cgt | 1822 |

```
                                                             -continued

Arg Asp Thr Asp Gly Asn Glu Leu Pro Arg Leu Val Tyr Val Ser Arg
        515                 520                 525 gag aag cgg cct gga ttt gat cac cac aag aaa gct gga gct atg aat    1870
Glu Lys Arg Pro Gly Phe Asp His His Lys Lys Ala Gly Ala Met Asn
    530                 535                 540 tcc ttg atc cga gtc tct gct gtt cta tca aac gct cct tac ctt ctt    1918
Ser Leu Ile Arg Val Ser Ala Val Leu Ser Asn Ala Pro Tyr Leu Leu
545                 550                 555                 560 aat gtc gat tgt gat cac tac atc aac aac agc aaa gca att aga gaa    1966
Asn Val Asp Cys Asp His Tyr Ile Asn Asn Ser Lys Ala Ile Arg Glu
                565                 570                 575 tct atg tgt ttc atg atg gac ccg caa tcg gga aag aaa gtt tgt tat    2014
Ser Met Cys Phe Met Met Asp Pro Gln Ser Gly Lys Lys Val Cys Tyr
            580                 585                 590 gtt cag ttt ccg cag aga ttt gat ggg att gat aga cat gat aga tac    2062
Val Gln Phe Pro Gln Arg Phe Asp Gly Ile Asp Arg His Asp Arg Tyr
        595                 600                 605 tca aac cgt aac gtt gtg ttc ttt gat att aac atg aaa ggt ctt gat    2110
Ser Asn Arg Asn Val Val Phe Phe Asp Ile Asn Met Lys Gly Leu Asp
    610                 615                 620 ggg ata caa gga ccg ata tat gtc ggg aca ggt tgt gtg ttt aga aaa    2158
Gly Ile Gln Gly Pro Ile Tyr Val Gly Thr Gly Cys Val Phe Arg Lys
625                 630                 635                 640 cag gct ctt tat ggt ttt gat gca cca aag aag aag aaa cca cca ggc    2206
Gln Ala Leu Tyr Gly Phe Asp Ala Pro Lys Lys Lys Lys Pro Pro Gly
                645                 650                 655 aaa acc tgt aac tgt tgg cct aaa tgg tgt tgt ttg tgt tgt ggg ttg    2254
Lys Thr Cys Asn Cys Trp Pro Lys Trp Cys Cys Leu Cys Cys Gly Leu
            660                 665                 670 aga aag aag agt aaa acg aaa gcc aca gat aag aaa act aac act aaa    2302
Arg Lys Lys Ser Lys Thr Lys Ala Thr Asp Lys Lys Thr Asn Thr Lys
        675                 680                 685 gag act tca aag cag att cat gcg cta gag aat gtc gac gaa ggt gtt    2350
Glu Thr Ser Lys Gln Ile His Ala Leu Glu Asn Val Asp Glu Gly Val
    690                 695                 700 atc gtc cca gtg tca aat gtt gag aag aga tct gaa gca aca caa ttg    2398
Ile Val Pro Val Ser Asn Val Glu Lys Arg Ser Glu Ala Thr Gln Leu
705                 710                 715                 720 aaa ttg gag aag aag ttt gga caa tct ccg gtt ttc gtt gcc tct gct    2446
Lys Leu Glu Lys Lys Phe Gly Gln Ser Pro Val Phe Val Ala Ser Ala
                725                 730                 735 gtt cta cag aac ggt gga gtt ccc cgt aac gca agc ccc gca tgt ttg    2494
Val Leu Gln Asn Gly Gly Val Pro Arg Asn Ala Ser Pro Ala Cys Leu
            740                 745                 750 tta aga gaa gcc att caa gtt att agc tgc ggg tac caa gat aaa acc    2542
Leu Arg Glu Ala Ile Gln Val Ile Ser Cys Gly Tyr Gln Asp Lys Thr
        755                 760                 765 gaa tgg gga aaa gag atc ggg tgg att tat gga tcg gtg act gaa gat    2590
Glu Trp Gly Lys Glu Ile Gly Trp Ile Tyr Gly Ser Val Thr Glu Asp
    770                 775                 780 atc ctg acg ggt ttc aag atg cat tgc cat gga tgg aga tct gtg tac    2638
Ile Leu Thr Gly Phe Lys Met His Cys His Gly Trp Arg Ser Val Tyr
785                 790                 795                 800 tgt atg cct aag cgt gca gct ttt aaa gga tct gct cct att aac ttg    2686
Cys Met Pro Lys Arg Ala Ala Phe Lys Gly Ser Ala Pro Ile Asn Leu
                805                 810                 815 tca gat cgt ctt cat caa gtt cta cgt tgg gct ctt ggc tct gta gag    2734
Ser Asp Arg Leu His Gln Val Leu Arg Trp Ala Leu Gly Ser Val Glu
            820                 825                 830
```

```
att ttc ttg agc aga cat tgt ccg ata tgg tat ggt tat ggt ggt ggt    2782
Ile Phe Leu Ser Arg His Cys Pro Ile Trp Tyr Gly Tyr Gly Gly Gly
        835                 840                 845 tta aaa tgg ttg gag aga ttc tct tac atc aac tct gtc gtc tat cct    2830
Leu Lys Trp Leu Glu Arg Phe Ser Tyr Ile Asn Ser Val Val Tyr Pro
    850                 855                 860 tgg act tca ctt cca ttg atc gtc tat tgt tct ctc ccc gcg gtt tgt    2878
Trp Thr Ser Leu Pro Leu Ile Val Tyr Cys Ser Leu Pro Ala Val Cys
865                 870                 875                 880 tta ctc aca gga aaa ttc atc gtc cct gag ata agc aac tac gca ggt    2926
Leu Leu Thr Gly Lys Phe Ile Val Pro Glu Ile Ser Asn Tyr Ala Gly
                885                 890                 895 ata ctc ttc atg ctc atg ttc ata tcc ata gca gta act gga atc ctc    2974
Ile Leu Phe Met Leu Met Phe Ile Ser Ile Ala Val Thr Gly Ile Leu
            900                 905                 910 gaa atg caa tgg gga ggt gtc gga atc gat gat tgg tgg aga aac gag    3022
Glu Met Gln Trp Gly Gly Val Gly Ile Asp Asp Trp Trp Arg Asn Glu
        915                 920                 925 cag ttt tgg gta atc gga ggg gcc tcc tcg cat cta ttt gct ctg ttt    3070
Gln Phe Trp Val Ile Gly Gly Ala Ser Ser His Leu Phe Ala Leu Phe
    930                 935                 940 caa ggt ttg ctc aaa gtt cta gcc gga gtt aac acg aat ttc aca gtc    3118
Gln Gly Leu Leu Lys Val Leu Ala Gly Val Asn Thr Asn Phe Thr Val
945                 950                 955                 960 act tca aaa gca gca gac gat gga gct ttc tct gag ctt tac atc ttc    3166
Thr Ser Lys Ala Ala Asp Asp Gly Ala Phe Ser Glu Leu Tyr Ile Phe
                965                 970                 975 aag tgg aca act ttg ttg att cct ccg aca aca ctt ctg atc att aac    3214
Lys Trp Thr Thr Leu Leu Ile Pro Pro Thr Thr Leu Leu Ile Ile Asn
            980                 985                 990 atc att gga gtt att gtc ggc gtt tct gat gcc att agc aat ggc tat    3262
Ile Ile Gly Val Ile Val Gly Val Ser Asp Ala Ile Ser Asn Gly Tyr
        995                 1000                1005 gac tca tgg gga cct ctc ttt ggg aga ctt ttc ttc gct ctt tgg gtc    3310
Asp Ser Trp Gly Pro Leu Phe Gly Arg Leu Phe Phe Ala Leu Trp Val
    1010                1015                1020 att gtt cat tta tac cca ttc ctc aag gga atg ctt ggg aag caa gac    3358
Ile Val His Leu Tyr Pro Phe Leu Lys Gly Met Leu Gly Lys Gln Asp
1025                1030                1035                1040 aaa atg cct acg att att gtg gtc tgg tct att ctt cta gct tcg atc    3406
Lys Met Pro Thr Ile Ile Val Val Trp Ser Ile Leu Leu Ala Ser Ile
                1045                1050                1055 ttg aca ctc ttg tgg gtc aga att aac ccg ttt gtg gct aaa ggg gga    3454
Leu Thr Leu Leu Trp Val Arg Ile Asn Pro Phe Val Ala Lys Gly Gly
            1060                1065                1070 cca gtg ttg gag atc tgt ggt ctg aat tgt gga aac taagatcctc         3500
Pro Val Leu Glu Ile Cys Gly Leu Asn Cys Gly Asn
        1075                1080 agtgaaagaa gagcaaagga gtttgtgttg gagctttgga agcaaatgtg ttgatgatga   3560
tgcaagtgtg tttgtagaca aagatgtgca gtttttactt tttacgactt gttaaacctt   3620
ttttgttacc cctaaattaa ttcttttgtt atcatggtta tactaataga attgtttgtt   3680 tttcttttt acatgtactt ttagttattc cgtagttatt gtataatact gataacgatc   3740
atatatacac actttgttaa caaaaaaaaa aaaaaaaaaa aaaaaaaaa aaagcggccg   3800 ctcgaattgt cgacgcggcc gcgaattc                                      3828
```

<210> SEQ ID NO 8
<211> LENGTH: 1084

```
<212> TYPE: PRT
<213> ORGANISM: Arabidopsis thaliana

<400> SEQUENCE: 8

Met Asn Thr Gly Gly Arg Leu Ile Ala Gly Ser His Asn Arg Asn Glu
 1               5                  10                  15

Phe Val Leu Ile Asn Ala Asp Glu Ser Ala Arg Ile Arg Ser Val Gln
             20                  25                  30

Glu Leu Ser Gly Gln Thr Cys Gln Ile Cys Gly Asp Glu Ile Glu Leu
         35                  40                  45

Thr Val Ser Ser Glu Leu Phe Val Ala Cys Asn Glu Cys Ala Phe Pro
     50                  55                  60

Val Cys Arg Pro Cys Tyr Glu Tyr Glu Arg Arg Glu Gly Asn Gln Ala
 65                  70                  75                  80

Cys Pro Gln Cys Lys Thr Arg Tyr Lys Arg Ile Lys Gly Ser Pro Arg
                 85                  90                  95

Val Asp Gly Asp Asp Glu Glu Glu Asp Ile Asp Asp Leu Glu Tyr
            100                 105                 110

Glu Phe Asp His Gly Met Asp Pro Glu His Ala Ala Glu Ala Ala Leu
            115                 120                 125

Ser Ser Arg Leu Asn Thr Gly Arg Gly Gly Leu Asp Ser Ala Pro Pro
        130                 135                 140

Gly Ser Gln Ile Pro Leu Leu Thr Tyr Cys Asp Glu Asp Ala Asp Met
145                 150                 155                 160

Tyr Ser Asp Arg His Ala Leu Ile Val Pro Pro Ser Thr Gly Tyr Gly
                165                 170                 175

Asn Arg Val Tyr Pro Ala Pro Phe Thr Asp Ser Ser Ala Pro Pro Gln
            180                 185                 190

Ala Arg Ser Met Val Pro Gln Lys Asp Ile Ala Glu Tyr Gly Tyr Gly
        195                 200                 205

Ser Val Ala Trp Lys Asp Arg Met Glu Val Trp Lys Arg Arg Gln Gly
    210                 215                 220

Glu Lys Leu Gln Val Ile Lys His Glu Gly Gly Asn Asn Gly Arg Gly
225                 230                 235                 240

Ser Asn Asp Asp Asp Glu Leu Asp Asp Pro Asp Met Pro Met Met Asp
                245                 250                 255

Glu Gly Arg Gln Pro Leu Ser Arg Lys Leu Pro Ile Arg Ser Ser Arg
            260                 265                 270

Ile Asn Pro Tyr Arg Met Leu Ile Leu Cys Arg Leu Ala Ile Leu Gly
        275                 280                 285

Leu Phe Phe His Tyr Arg Ile Leu His Pro Val Asn Asp Ala Tyr Gly
    290                 295                 300

Leu Trp Leu Thr Ser Val Ile Cys Glu Ile Trp Phe Ala Val Ser Trp
305                 310                 315                 320

Ile Leu Asp Gln Phe Pro Lys Trp Tyr Pro Ile Glu Arg Glu Thr Tyr
                325                 330                 335

Leu Asp Arg Leu Ser Leu Arg Tyr Glu Lys Glu Gly Lys Pro Ser Gly
            340                 345                 350

Leu Ala Pro Val Asp Val Phe Val Ser Thr Val Asp Pro Leu Lys Glu
        355                 360                 365

Pro Pro Leu Ile Thr Ala Asn Thr Val Leu Ser Ile Leu Ala Val Asp
    370                 375                 380

Tyr Pro Val Asp Lys Val Ala Cys Tyr Val Ser Asn Asn Gly Ala Ala
385                 390                 395                 400
```

```
Met Leu Thr Phe Glu Ala Leu Ser Asp Thr Ala Asp Phe Ala Thr Lys
            405                 410                 415
Trp Val Pro Phe Cys Lys Lys Phe Asn Ile Glu Pro Arg Ala Pro Glu
            420                 425                 430
Trp Tyr Phe Ser Gln Lys Met Asp Tyr Leu Lys Asn Lys Val His Pro
            435                 440                 445
Ala Phe Val Arg Glu Arg Arg Ala Met Lys Arg Asp Tyr Glu Glu Phe
            450                 455                 460
Lys Val Lys Ile Asn Ala Leu Val Ala Thr Ala Gln Lys Val Pro Glu
465                 470                 475                 480
Glu Arg Trp Thr Met Gln Asp Gly Thr Pro Trp Pro Gly Asn Asn Val
            485                 490                 495
Arg Asp His Pro Gly Met Ile Gln Val Phe Leu Gly His Ser Gly Val
            500                 505                 510
Arg Asp Thr Asp Gly Asn Glu Leu Pro Arg Leu Val Tyr Val Ser Arg
            515                 520                 525
Glu Lys Arg Pro Gly Phe Asp His His Lys Lys Ala Gly Ala Met Asn
            530                 535                 540
Ser Leu Ile Arg Val Ser Ala Val Leu Ser Asn Ala Pro Tyr Leu Leu
545                 550                 555                 560
Asn Val Asp Cys Asp His Tyr Ile Asn Asn Ser Lys Ala Ile Arg Glu
            565                 570                 575
Ser Met Cys Phe Met Met Asp Pro Gln Ser Gly Lys Lys Val Cys Tyr
            580                 585                 590
Val Gln Phe Pro Gln Arg Phe Asp Gly Ile Asp Arg His Asp Arg Tyr
            595                 600                 605
Ser Asn Arg Asn Val Val Phe Phe Asp Ile Asn Met Lys Gly Leu Asp
            610                 615                 620
Gly Ile Gln Gly Pro Ile Tyr Val Gly Thr Gly Cys Val Phe Arg Lys
625                 630                 635                 640
Gln Ala Leu Tyr Gly Phe Asp Ala Pro Lys Lys Lys Pro Pro Gly
            645                 650                 655
Lys Thr Cys Asn Cys Trp Pro Lys Trp Cys Cys Leu Cys Cys Gly Leu
            660                 665                 670
Arg Lys Lys Ser Lys Thr Lys Ala Thr Asp Lys Lys Thr Asn Thr Lys
            675                 680                 685
Glu Thr Ser Lys Gln Ile His Ala Leu Glu Asn Val Asp Glu Gly Val
            690                 695                 700
Ile Val Pro Val Ser Asn Val Glu Lys Arg Ser Glu Ala Thr Gln Leu
705                 710                 715                 720
Lys Leu Glu Lys Lys Phe Gly Gln Ser Pro Val Phe Val Ala Ser Ala
            725                 730                 735
Val Leu Gln Asn Gly Gly Val Pro Arg Asn Ala Ser Pro Ala Cys Leu
            740                 745                 750
Leu Arg Glu Ala Ile Gln Val Ile Ser Cys Gly Tyr Gln Asp Lys Thr
            755                 760                 765
Glu Trp Gly Lys Glu Ile Gly Trp Ile Tyr Gly Ser Val Thr Glu Asp
            770                 775                 780
Ile Leu Thr Gly Phe Lys Met His Cys His Gly Trp Arg Ser Val Tyr
785                 790                 795                 800
Cys Met Pro Lys Arg Ala Ala Phe Lys Gly Ser Ala Pro Ile Asn Leu
            805                 810                 815
```

```
Ser Asp Arg Leu His Gln Val Leu Arg Trp Ala Leu Gly Ser Val Glu
        820                 825                 830

Ile Phe Leu Ser Arg His Cys Pro Ile Trp Tyr Gly Tyr Gly Gly Gly
        835                 840                 845

Leu Lys Trp Leu Glu Arg Phe Ser Tyr Ile Asn Ser Val Val Tyr Pro
    850                 855                 860

Trp Thr Ser Leu Pro Leu Ile Val Tyr Cys Ser Leu Pro Ala Val Cys
865                 870                 875                 880

Leu Leu Thr Gly Lys Phe Ile Val Pro Glu Ile Ser Asn Tyr Ala Gly
                885                 890                 895

Ile Leu Phe Met Leu Met Phe Ile Ser Ile Ala Val Thr Gly Ile Leu
                900                 905                 910

Glu Met Gln Trp Gly Val Gly Ile Asp Asp Trp Arg Asn Glu
        915                 920                 925

Gln Phe Trp Val Ile Gly Ala Ser Ser His Leu Phe Ala Leu Phe
        930                 935                 940

Gln Gly Leu Leu Lys Val Leu Ala Gly Val Asn Thr Asn Phe Thr Val
945                 950                 955                 960

Thr Ser Lys Ala Ala Asp Asp Gly Ala Phe Ser Glu Leu Tyr Ile Phe
                965                 970                 975

Lys Trp Thr Thr Leu Leu Ile Pro Pro Thr Thr Leu Leu Ile Ile Asn
                980                 985                 990

Ile Ile Gly Val Ile Val Gly Val Ser Asp Ala Ile Ser Asn Gly Tyr
                995                 1000                1005

Asp Ser Trp Gly Pro Leu Phe Gly Arg Leu Phe Phe Ala Leu Trp Val
        1010                1015                1020

Ile Val His Leu Tyr Pro Phe Leu Lys Gly Met Leu Gly Lys Gln Asp
1025                1030                1035                1040

Lys Met Pro Thr Ile Ile Val Val Trp Ser Ile Leu Leu Ala Ser Ile
                1045                1050                1055

Leu Thr Leu Leu Trp Val Arg Ile Asn Pro Phe Val Ala Lys Gly Gly
        1060                1065                1070

Pro Val Leu Glu Ile Cys Gly Leu Asn Cys Gly Asn
        1075                1080

<210> SEQ ID NO 9
<211> LENGTH: 3614
<212> TYPE: DNA
<213> ORGANISM: Arabidopsis thaliana
<220> FEATURE:
<221> NAME/KEY: CDS
<222> LOCATION: (217)..(3411)

<400> SEQUENCE: 9
gaattcgcgg ccgcgtcgac tacggctgcg agaagacgac agaagggat cccaagattc      60 tcctcttcgt cttccttata aactatctct ctgtagagaa gaaagcttgg atccagattg    120
agagagattc agagagccac atcaccacac tccatcttca gatctcatga tttgaactat    180
tccgacgttt cggtgttgga agcaactaag tgacaa atg gaa tcc gaa gga gaa      234
                                     Met Glu Ser Glu Gly Glu
                                       1               5 acc gcg gga aag ccg atg aag aac att gtt ccg cag act tgc cag atc    282
Thr Ala Gly Lys Pro Met Lys Asn Ile Val Pro Gln Thr Cys Gln Ile
            10                  15                  20 tgt agt gac aat gtt ggc aag act gtt gat gga gat cgt ttt gtg gct    330
Cys Ser Asp Asn Val Gly Lys Thr Val Asp Gly Asp Arg Phe Val Ala
        25                  30                  35
```

```
tgt gat att tgt tca ttc cca gtt tgt cgg cct tgc tac gag tat gag      378
Cys Asp Ile Cys Ser Phe Pro Val Cys Arg Pro Cys Tyr Glu Tyr Glu
         40                  45                  50 agg aaa gat ggg aat caa tct tgt cct cag tgc aaa acc aga tac aag      426
Arg Lys Asp Gly Asn Gln Ser Cys Pro Gln Cys Lys Thr Arg Tyr Lys
 55                  60                  65                  70 agg ctc aaa ggt agt cct gct att cct ggt gat aaa gac gag gat ggc      474
Arg Leu Lys Gly Ser Pro Ala Ile Pro Gly Asp Lys Asp Glu Asp Gly
                 75                  80                  85 tta gct gat gaa ggt act gtt gag ttc aac tac cct cag aag gag aaa      522
Leu Ala Asp Glu Gly Thr Val Glu Phe Asn Tyr Pro Gln Lys Glu Lys
             90                  95                 100 att tca gag cgg atg ctt ggt tgg cat ctt act cgt ggg aag gga gag      570
Ile Ser Glu Arg Met Leu Gly Trp His Leu Thr Arg Gly Lys Gly Glu
        105                 110                 115 gaa atg ggg gaa ccc cag tat gat aaa gag gtc tct cac aat cat ctt      618
Glu Met Gly Glu Pro Gln Tyr Asp Lys Glu Val Ser His Asn His Leu
    120                 125                 130 cct cgt ctc acg agc aga caa gat act tca gga gag ttt tct gct gcc      666
Pro Arg Leu Thr Ser Arg Gln Asp Thr Ser Gly Glu Phe Ser Ala Ala
135                 140                 145                 150 tca cct gaa cgc ctc tct gta tct tct act atc gct ggg gga aag cgc      714
Ser Pro Glu Arg Leu Ser Val Ser Ser Thr Ile Ala Gly Gly Lys Arg
                155                 160                 165 ctt ccc tat tca tca gat gtc aat caa tca cca aat aga agg att gtg      762
Leu Pro Tyr Ser Ser Asp Val Asn Gln Ser Pro Asn Arg Arg Ile Val
            170                 175                 180 gat cct gtt gga ctc ggg aat gta gct tgg aag gag aga gtt gat ggc      810
Asp Pro Val Gly Leu Gly Asn Val Ala Trp Lys Glu Arg Val Asp Gly
        185                 190                 195 tgg aaa atg aag caa gag aag aat act ggt cct gtc agc acg cag gct      858
Trp Lys Met Lys Gln Glu Lys Asn Thr Gly Pro Val Ser Thr Gln Ala
    200                 205                 210 gct tct gaa aga ggt gga gta gat att gat gcc agc aca gat atc cta      906
Ala Ser Glu Arg Gly Gly Val Asp Ile Asp Ala Ser Thr Asp Ile Leu
215                 220                 225                 230 gca gat gag gct ctg ctg aat gac gaa gcg agg cag ctt ctg tca agg      954
Ala Asp Glu Ala Leu Leu Asn Asp Glu Ala Arg Gln Leu Leu Ser Arg
                235                 240                 245 aaa gtt tca att cct tca tca cgg atc aat cct tac aga atg gtt att     1002
Lys Val Ser Ile Pro Ser Ser Arg Ile Asn Pro Tyr Arg Met Val Ile
            250                 255                 260 atg ctg cgg ctt gtt atc ctt tgt ctc ttc ttg cat tac cgt ata aca     1050
Met Leu Arg Leu Val Ile Leu Cys Leu Phe Leu His Tyr Arg Ile Thr
        265                 270                 275 aac cca gtg cca aat gcc ttt gct cta tgg ctg gtc tct gtg ata tgt     1098
Asn Pro Val Pro Asn Ala Phe Ala Leu Trp Leu Val Ser Val Ile Cys
    280                 285                 290 gag atc tgg ttt gcc tta tcc tgg att ttg gat cag ttt ccc aag tgg     1146
Glu Ile Trp Phe Ala Leu Ser Trp Ile Leu Asp Gln Phe Pro Lys Trp
295                 300                 305                 310 ttt cct gtg aac cgt gaa acc tac ctc gac agg ctt gct tta aga tat     1194
Phe Pro Val Asn Arg Glu Thr Tyr Leu Asp Arg Leu Ala Leu Arg Tyr
                315                 320                 325 gat cgt gaa ggt gag cca tca cag tta gct gct gtt gac att ttc gtg     1242
Asp Arg Glu Gly Glu Pro Ser Gln Leu Ala Ala Val Asp Ile Phe Val
            330                 335                 340 agt act gtt gac ccc ttg aag gag cca ccc ctt gtg aca gcc aac aca     1290
Ser Thr Val Asp Pro Leu Lys Glu Pro Pro Leu Val Thr Ala Asn Thr
```

-continued

```
                345                 350                 355
gtg ctc tct att ctg gct gtt gac tac cca gtt gac aag gtg tcc tgt    1338
Val Leu Ser Ile Leu Ala Val Asp Tyr Pro Val Asp Lys Val Ser Cys
    360                 365                 370 tat gtt tct gat gat ggt gct gct atg tta tca ttt gaa tca ctt gca    1386
Tyr Val Ser Asp Asp Gly Ala Ala Met Leu Ser Phe Glu Ser Leu Ala
375                 380                 385                 390 gaa aca tca gag ttt gct cgt aaa tgg gta cca ttt tgc aag aaa tat    1434
Glu Thr Ser Glu Phe Ala Arg Lys Trp Val Pro Phe Cys Lys Lys Tyr
                395                 400                 405 agc ata gag cct cgt gca cca gaa tgg tac ttt gct gcg aaa ata gat    1482
Ser Ile Glu Pro Arg Ala Pro Glu Trp Tyr Phe Ala Ala Lys Ile Asp
            410                 415                 420 tac ttg aag gat aaa gtt cag aca tca ttt gtc aaa gat cgt aga gct    1530
Tyr Leu Lys Asp Lys Val Gln Thr Ser Phe Val Lys Asp Arg Arg Ala
        425                 430                 435 atg aag agg gaa tat gag gaa ttt aaa atc cga atc aat gca ctt gtt    1578
Met Lys Arg Glu Tyr Glu Glu Phe Lys Ile Arg Ile Asn Ala Leu Val
    440                 445                 450 tcc aaa gcc cta aaa tgt cct gaa gaa ggg tgg gtt atg caa gat ggc    1626
Ser Lys Ala Leu Lys Cys Pro Glu Glu Gly Trp Val Met Gln Asp Gly
455                 460                 465                 470 aca ccg tgg cct gga aat aat aca ggg gac cat cca gga atg atc cag    1674
Thr Pro Trp Pro Gly Asn Asn Thr Gly Asp His Pro Gly Met Ile Gln
                475                 480                 485 gtc ttc tta ggg caa aat ggt gga ctt gat gca gag ggc aat gag ctc    1722
Val Phe Leu Gly Gln Asn Gly Gly Leu Asp Ala Glu Gly Asn Glu Leu
            490                 495                 500 ccg cgt ttg gta tat gtt tct cga gaa aag cga cca gga ttc cag cac    1770
Pro Arg Leu Val Tyr Val Ser Arg Glu Lys Arg Pro Gly Phe Gln His
        505                 510                 515 cac aaa aag gct ggt gct atg aat gca ctg gtg aga gtt tca gca gtt    1818
His Lys Lys Ala Gly Ala Met Asn Ala Leu Val Arg Val Ser Ala Val
    520                 525                 530 ctt acc aat gga cct ttc atc ttg aat ctt gat tgt gat cat tac ata    1866
Leu Thr Asn Gly Pro Phe Ile Leu Asn Leu Asp Cys Asp His Tyr Ile
535                 540                 545                 550 aat aac agc aaa gcc tta aga gaa gca atg tgc ttc ctg atg gac cca    1914
Asn Asn Ser Lys Ala Leu Arg Glu Ala Met Cys Phe Leu Met Asp Pro
                555                 560                 565 aac ctc ggg aag caa gtt tgt tat gtt cag ttc cca caa aga ttt gat    1962
Asn Leu Gly Lys Gln Val Cys Tyr Val Gln Phe Pro Gln Arg Phe Asp
            570                 575                 580 ggt atc gat aag aac gat aga tat gct aat cgt aat acc gtg ttc ttt    2010
Gly Ile Asp Lys Asn Asp Arg Tyr Ala Asn Arg Asn Thr Val Phe Phe
        585                 590                 595 gat att aac ttg aga ggt tta gat ggg att caa gga cct gta tat gtc    2058
Asp Ile Asn Leu Arg Gly Leu Asp Gly Ile Gln Gly Pro Val Tyr Val
    600                 605                 610 gga act gga tgt gtt ttc aac aga aca gca tta tac ggt tat gaa cct    2106
Gly Thr Gly Cys Val Phe Asn Arg Thr Ala Leu Tyr Gly Tyr Glu Pro
615                 620                 625                 630 cca ata aaa gta aaa cac aag aag cca agt ctt tta tct aag ctc tgt    2154
Pro Ile Lys Val Lys His Lys Lys Pro Ser Leu Leu Ser Lys Leu Cys
                635                 640                 645 ggt gga tca aga aag aag aat tcc aaa gct aag aaa gag tcg gac aaa    2202
Gly Gly Ser Arg Lys Lys Asn Ser Lys Ala Lys Lys Glu Ser Asp Lys
            650                 655                 660 aag aaa tca ggc agg cat act gac tca act gtt cct gta ttc aac ctc    2250
```

```
                                                            -continued

Lys Lys Ser Gly Arg His Thr Asp Ser Thr Val Pro Val Phe Asn Leu
        665                 670                 675 gat gac ata gaa gag gga gtt gaa ggt gct ggt ttt gat gat gaa aag     2298
Asp Asp Ile Glu Glu Gly Val Glu Gly Ala Gly Phe Asp Asp Glu Lys
680                 685                 690 gcg ctc tta atg tcg caa atg agc ctg gag aag cga ttt gga cag tct     2346
Ala Leu Leu Met Ser Gln Met Ser Leu Glu Lys Arg Phe Gly Gln Ser
695                 700                 705                 710 gct gtt ttt gtt gct tct acc cta atg gaa aat ggt ggt gtt cct cct     2394
Ala Val Phe Val Ala Ser Thr Leu Met Glu Asn Gly Gly Val Pro Pro
                715                 720                 725 tca gca act cca gaa aac ttt ctc aaa gag gct atc cat gtc att agt     2442
Ser Ala Thr Pro Glu Asn Phe Leu Lys Glu Ala Ile His Val Ile Ser
            730                 735                 740 tgt ggt tat gag gat aag tca gat tgg gga atg gag att gga tgg atc     2490
Cys Gly Tyr Glu Asp Lys Ser Asp Trp Gly Met Glu Ile Gly Trp Ile
        745                 750                 755 tat ggt tct gtg aca gaa gat att ctg act ggg ttc aaa atg cat gcc     2538
Tyr Gly Ser Val Thr Glu Asp Ile Leu Thr Gly Phe Lys Met His Ala
760                 765                 770 cgt gga tgg cga tcc att tac tgc atg cct aag ctt cca gct ttc aag     2586
Arg Gly Trp Arg Ser Ile Tyr Cys Met Pro Lys Leu Pro Ala Phe Lys
775                 780                 785                 790 ggt tct gct cct atc aat ctt tca gat cgt ctg aac caa gtg ctg agg     2634
Gly Ser Ala Pro Ile Asn Leu Ser Asp Arg Leu Asn Gln Val Leu Arg
                795                 800                 805 tgg gct tta ggt tca gtt gag att ctc ttc agt cgg cat tgt cct ata     2682
Trp Ala Leu Gly Ser Val Glu Ile Leu Phe Ser Arg His Cys Pro Ile
            810                 815                 820 tgg tat ggt tac aat ggg agg cta aaa ttt ctt gag agg ttt gcg tat     2730
Trp Tyr Gly Tyr Asn Gly Arg Leu Lys Phe Leu Glu Arg Phe Ala Tyr
        825                 830                 835 gtg aac acc acc atc tac cct atc acc tcc att cct ctt ctc atg tat     2778
Val Asn Thr Thr Ile Tyr Pro Ile Thr Ser Ile Pro Leu Leu Met Tyr
840                 845                 850 tgt aca ttg cta gcc gtt tgt ctc ttc acc aac cag ttt att att cct     2826
Cys Thr Leu Leu Ala Val Cys Leu Phe Thr Asn Gln Phe Ile Ile Pro
855                 860                 865                 870 cag att agt aac att gca agt ata tgg ttt ctg tct ctc ttt ctc tcc     2874
Gln Ile Ser Asn Ile Ala Ser Ile Trp Phe Leu Ser Leu Phe Leu Ser
                875                 880                 885 att ttc gcc acg ggt ata cta gaa atg agg tgg agt ggc gta ggc ata     2922
Ile Phe Ala Thr Gly Ile Leu Glu Met Arg Trp Ser Gly Val Gly Ile
            890                 895                 900 gac gaa tgg tgg aga aac gag cag ttt tgg gtc att ggt gga gta tcc     2970
Asp Glu Trp Trp Arg Asn Glu Gln Phe Trp Val Ile Gly Gly Val Ser
        905                 910                 915 gct cat tta ttc gct gtg ttt caa ggt atc ctc aaa gtc ctt gcc ggt     3018
Ala His Leu Phe Ala Val Phe Gln Gly Ile Leu Lys Val Leu Ala Gly
920                 925                 930 att gac aca aac ttc aca gtt acc tca aaa gct tca gat gaa gac gga     3066
Ile Asp Thr Asn Phe Thr Val Thr Ser Lys Ala Ser Asp Glu Asp Gly
935                 940                 945                 950 gac ttt gct gag ctc tac ttg ttc aaa tgg aca aca ctt ctg att ccg     3114
Asp Phe Ala Glu Leu Tyr Leu Phe Lys Trp Thr Thr Leu Leu Ile Pro
                955                 960                 965 cca acg acg ctg ctc att gta aac tta gtg gga gtt gtt gca gga gtc     3162
Pro Thr Thr Leu Leu Ile Val Asn Leu Val Gly Val Val Ala Gly Val
            970                 975                 980
```

```
tct tat gct atc aac agt gga tac caa tca tgg gga cca ctc ttt ggt    3210
Ser Tyr Ala Ile Asn Ser Gly Tyr Gln Ser Trp Gly Pro Leu Phe Gly
        985                 990                 995 aag ttg ttc ttt gcc ttc tgg gtg att gtt cac ttg tac cct ttc ctc    3258
Lys Leu Phe Phe Ala Phe Trp Val Ile Val His Leu Tyr Pro Phe Leu
    1000                1005                1010 aag ggt ttg atg ggt cga cag aac cgg act cct acc att gtt gtg gtc    3306
Lys Gly Leu Met Gly Arg Gln Asn Arg Thr Pro Thr Ile Val Val Val
1015                1020                1025                1030 tgg tct gtt ctc ttg gct tct atc ttc tcg ttg ttg tgg gtt agg att    3354
Trp Ser Val Leu Leu Ala Ser Ile Phe Ser Leu Leu Trp Val Arg Ile
                1035                1040                1045 gat ccc ttc act agc cga gtc act ggc ccg gac att ctg gaa tgt gga    3402
Asp Pro Phe Thr Ser Arg Val Thr Gly Pro Asp Ile Leu Glu Cys Gly
            1050                1055                1060 atc aac tgt tgagaagcga gcaaatattt acctgttttg agggttaaaa            3451
Ile Asn Cys
        1065 aaaacacaga atttaaatta tttttcattg ttttatttgt tcacttttt acttttgttg   3511 tgtgtatctg tctgttcgtt cttctgtctt ggtgtcataa atttatgtgt agaatatatc  3571 ttactctagt tactttggaa agttataatt aaagtgaaag cca                    3614
```

<210> SEQ ID NO 10
<211> LENGTH: 1065
<212> TYPE: PRT
<213> ORGANISM: Arabidopsis thaliana

<400> SEQUENCE: 10

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
            85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220
```

-continued

```
Ala Ser Thr Asp Ile Leu Ala Asp Glu Ala Leu Leu Asn Asp Glu Ala
225                 230                 235                 240

Arg Gln Leu Leu Ser Arg Lys Val Ser Ile Pro Ser Ser Arg Ile Asn
            245                 250                 255

Pro Tyr Arg Met Val Ile Met Leu Arg Leu Val Ile Leu Cys Leu Phe
                260                 265                 270

Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
            325                 330                 335

Ala Val Asp Ile Phe Val Ser Thr Val Asp Pro Leu Lys Glu Pro Pro
                340                 345                 350

Leu Val Thr Ala Asn Thr Val Leu Ser Ile Leu Ala Val Asp Tyr Pro
            355                 360                 365

Val Asp Lys Val Ser Cys Tyr Val Ser Asp Asp Gly Ala Ala Met Leu
370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
            435                 440                 445

Arg Ile Asn Ala Leu Val Ser Lys Ala Leu Lys Cys Pro Glu Glu Gly
            450                 455                 460

Trp Val Met Gln Asp Gly Thr Pro Trp Pro Gly Asn Asn Thr Gly Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
            515                 520                 525

Val Arg Val Ser Ala Val Leu Thr Asn Gly Pro Phe Ile Leu Asn Leu
530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                565                 570                 575

Phe Pro Gln Arg Phe Asp Gly Ile Asp Lys Asn Asp Arg Tyr Ala Asn
            580                 585                 590

Arg Asn Thr Val Phe Phe Asp Ile Asn Leu Arg Gly Leu Asp Gly Ile
            595                 600                 605

Gln Gly Pro Val Tyr Val Gly Thr Gly Cys Val Phe Asn Arg Thr Ala
610                 615                 620

Leu Tyr Gly Tyr Glu Pro Pro Ile Lys Val Lys His Lys Lys Pro Ser
625                 630                 635                 640
```

-continued

```
Leu Leu Ser Lys Leu Cys Gly Gly Ser Arg Lys Lys Asn Ser Lys Ala
                645                 650                 655
Lys Lys Glu Ser Asp Lys Lys Ser Gly Arg His Thr Asp Ser Thr
            660                 665                 670
Val Pro Val Phe Asn Leu Asp Asp Ile Glu Glu Gly Val Glu Gly Ala
            675                 680                 685
Gly Phe Asp Asp Glu Lys Ala Leu Leu Met Ser Gln Met Ser Leu Glu
    690                 695                 700
Lys Arg Phe Gly Gln Ser Ala Val Phe Val Ala Ser Thr Leu Met Glu
705                 710                 715                 720
Asn Gly Gly Val Pro Pro Ser Ala Thr Pro Glu Asn Phe Leu Lys Glu
                725                 730                 735
Ala Ile His Val Ile Ser Cys Gly Tyr Glu Asp Lys Ser Asp Trp Gly
            740                 745                 750
Met Glu Ile Gly Trp Ile Tyr Gly Ser Val Thr Glu Asp Ile Leu Thr
            755                 760                 765
Gly Phe Lys Met His Ala Arg Gly Trp Arg Ser Ile Tyr Cys Met Pro
    770                 775                 780
Lys Leu Pro Ala Phe Lys Gly Ser Ala Pro Ile Asn Leu Ser Asp Arg
785                 790                 795                 800
Leu Asn Gln Val Leu Arg Trp Ala Leu Gly Ser Val Glu Ile Leu Phe
                805                 810                 815
Ser Arg His Cys Pro Ile Trp Tyr Gly Tyr Asn Gly Arg Leu Lys Phe
            820                 825                 830
Leu Glu Arg Phe Ala Tyr Val Asn Thr Thr Ile Tyr Pro Ile Thr Ser
    835                 840                 845
Ile Pro Leu Leu Met Tyr Cys Thr Leu Leu Ala Val Cys Leu Phe Thr
850                 855                 860
Asn Gln Phe Ile Ile Pro Gln Ile Ser Asn Ile Ala Ser Ile Trp Phe
865                 870                 875                 880
Leu Ser Leu Phe Leu Ser Ile Phe Ala Thr Gly Ile Leu Glu Met Arg
                885                 890                 895
Trp Ser Gly Val Gly Ile Asp Glu Trp Trp Arg Asn Glu Gln Phe Trp
            900                 905                 910
Val Ile Gly Gly Val Ser Ala His Leu Phe Ala Val Phe Gln Gly Ile
            915                 920                 925
Leu Lys Val Leu Ala Gly Ile Asp Thr Asn Phe Thr Val Thr Ser Lys
    930                 935                 940
Ala Ser Asp Glu Asp Gly Asp Phe Ala Glu Leu Tyr Leu Phe Lys Trp
945                 950                 955                 960
Thr Thr Leu Leu Ile Pro Pro Thr Thr Leu Leu Ile Val Asn Leu Val
                965                 970                 975
Gly Val Val Ala Gly Val Ser Tyr Ala Ile Asn Ser Gly Tyr Gln Ser
            980                 985                 990
Trp Gly Pro Leu Phe Gly Lys Leu Phe Phe Ala Phe Trp Val Ile Val
    995                 1000                1005
His Leu Tyr Pro Phe Leu Lys Gly Leu Met Gly Arg Gln Asn Arg Thr
    1010                1015                1020
Pro Thr Ile Val Val Trp Ser Val Leu Leu Ala Ser Ile Phe Ser
1025                1030                1035                1040
Leu Leu Trp Val Arg Ile Asp Pro Phe Thr Ser Arg Val Thr Gly Pro
                1045                1050                1055
Asp Ile Leu Glu Cys Gly Ile Asn Cys
```

-continued

```
                 1060                1065
```

<210> SEQ ID NO 11
<211> LENGTH: 3673
<212> TYPE: DNA
<213> ORGANISM: Arabidopsis thaliana
<220> FEATURE:
<221> NAME/KEY: CDS
<222> LOCATION: (71)..(3313)

<400> SEQUENCE: 11

```
gaatcggcta cgaatttccc aattttgaat tttgtgaatc tctctctttc tctgtgtgtc      60
ggtggctgcg atg gag gcc agt gcc ggc ttg gtt gct gga tcc tac cgg        109
            Met Glu Ala Ser Ala Gly Leu Val Ala Gly Ser Tyr Arg
              1               5                  10 aga aac gag ctc gtt cgg atc cga cat gaa tct gat ggc ggg acc aaa      157
Arg Asn Glu Leu Val Arg Ile Arg His Glu Ser Asp Gly Gly Thr Lys
 15                  20                  25 cct ttg aag aat atg aat ggc cag ata tgt cag atc tgt ggt gat gat      205
Pro Leu Lys Asn Met Asn Gly Gln Ile Cys Gln Ile Cys Gly Asp Asp
 30                  35                  40                  45 gtt gga ctc gct gaa act gga gat gtc ttt gtc gcg tgt aat gaa tgt      253
Val Gly Leu Ala Glu Thr Gly Asp Val Phe Val Ala Cys Asn Glu Cys
                 50                  55                  60 gcc ttc cct gtg tgt cgg cct tgc tat gag tac gag agg aaa gat gga      301
Ala Phe Pro Val Cys Arg Pro Cys Tyr Glu Tyr Glu Arg Lys Asp Gly
             65                  70                  75 act cag tgt tgc cct caa tgc aag act aga ttc aga cga cac agg ggg      349
Thr Gln Cys Cys Pro Gln Cys Lys Thr Arg Phe Arg Arg His Arg Gly
         80                  85                  90 agt cct cgt gtt gaa gga gat gaa gat gag gat gat gtt gat gat atc      397
Ser Pro Arg Val Glu Gly Asp Glu Asp Glu Asp Asp Val Asp Asp Ile
     95                 100                 105 gag aat gag ttc aat tac gcc cag gga gct aac aag gcg aga cac caa      445
Glu Asn Glu Phe Asn Tyr Ala Gln Gly Ala Asn Lys Ala Arg His Gln
110                 115                 120                 125 cgc cat ggc gaa gag ttt tct tct tcc tct aga cat gaa tct caa cca      493
Arg His Gly Glu Glu Phe Ser Ser Ser Ser Arg His Glu Ser Gln Pro
                130                 135                 140 att cct ctt ctc acc cat ggc cat acg gtt tct gga gag att cgc acg      541
Ile Pro Leu Leu Thr His Gly His Thr Val Ser Gly Glu Ile Arg Thr
            145                 150                 155 cct gat aca caa tct gtg cga act aca tca ggt cct ttg ggt cct tct      589
Pro Asp Thr Gln Ser Val Arg Thr Thr Ser Gly Pro Leu Gly Pro Ser
        160                 165                 170 gac agg aat gct att tca tct cca tat att gat cca cgg caa cct gtc      637
Asp Arg Asn Ala Ile Ser Ser Pro Tyr Ile Asp Pro Arg Gln Pro Val
    175                 180                 185 cct gta aga atc gtg gac ccg tca aaa gac ttg aac tct tat ggg ctt      685
Pro Val Arg Ile Val Asp Pro Ser Lys Asp Leu Asn Ser Tyr Gly Leu
190                 195                 200                 205 ggt aat gtt gac tgg aaa gaa aga gtt gaa ggc tgg aag ctg aag cag      733
Gly Asn Val Asp Trp Lys Glu Arg Val Glu Gly Trp Lys Leu Lys Gln
                210                 215                 220 gag aaa aat atg tta cag atg act ggt aaa tac cat gaa ggg aaa gga      781
Glu Lys Asn Met Leu Gln Met Thr Gly Lys Tyr His Glu Gly Lys Gly
            225                 230                 235 gga gaa att gaa ggg act ggt tcc aat ggc gaa gaa ctc caa atg gct      829
Gly Glu Ile Glu Gly Thr Gly Ser Asn Gly Glu Glu Leu Gln Met Ala
        240                 245                 250
```

```
gat gat aca cgt ctt cct atg agt cgt gtg gtg cct atc cca tct tct    877
Asp Asp Thr Arg Leu Pro Met Ser Arg Val Val Pro Ile Pro Ser Ser
    255                 260                 265 cgc cta acc cct tat cgg gtt gtg att att ctc cgg ctt atc atc ttg    925
Arg Leu Thr Pro Tyr Arg Val Val Ile Ile Leu Arg Leu Ile Ile Leu
270                 275                 280                 285 tgt ttc ttc ttg caa tat cgt aca act cac cct gtg aaa aat gca tat    973
Cys Phe Phe Leu Gln Tyr Arg Thr Thr His Pro Val Lys Asn Ala Tyr
                290                 295                 300 cct ttg tgg ttg acc tcg gtt atc tgt gag atc tgg ttt gca ttt tct   1021
Pro Leu Trp Leu Thr Ser Val Ile Cys Glu Ile Trp Phe Ala Phe Ser
        305                 310                 315 tgg ctt ctt gat cag ttt ccc aaa tgg tac ccc att aac agg gag act   1069
Trp Leu Leu Asp Gln Phe Pro Lys Trp Tyr Pro Ile Asn Arg Glu Thr
            320                 325                 330 tat ctt gac cgt ctc gct ata aga tat gat cga gac ggt gaa cca tca   1117
Tyr Leu Asp Arg Leu Ala Ile Arg Tyr Asp Arg Asp Gly Glu Pro Ser
335                 340                 345 cag ctc gtt cct gtt gat gtg ttt gtt agt aca gtg gac cca ttg aaa   1165
Gln Leu Val Pro Val Asp Val Phe Val Ser Thr Val Asp Pro Leu Lys
350                 355                 360                 365 gag cct ccc ctt gtt aca gca aac aca gtt ctc tcg att ctt tct gtg   1213
Glu Pro Pro Leu Val Thr Ala Asn Thr Val Leu Ser Ile Leu Ser Val
                370                 375                 380 gac tac ccg gta gat aaa gta gcc tgt tat gtt tca gat gat ggt tca   1261
Asp Tyr Pro Val Asp Lys Val Ala Cys Tyr Val Ser Asp Asp Gly Ser
            385                 390                 395 gct atg ctt acc ttt gaa tcc ctt tct gaa acc gct gag ttt gca aag   1309
Ala Met Leu Thr Phe Glu Ser Leu Ser Glu Thr Ala Glu Phe Ala Lys
400                 405                 410 aaa tgg gta cca ttt tgc aag aaa ttc aac att gaa cct agg gcc cct   1357
Lys Trp Val Pro Phe Cys Lys Lys Phe Asn Ile Glu Pro Arg Ala Pro
    415                 420                 425 gaa ttc tat ttt gcc cag aag ata gat tac ttg aag gac aag atc caa   1405
Glu Phe Tyr Phe Ala Gln Lys Ile Asp Tyr Leu Lys Asp Lys Ile Gln
430                 435                 440                 445 ccg tct ttt gtt aaa gag cga cga gct atg aag aga gag tat gaa gag   1453
Pro Ser Phe Val Lys Glu Arg Arg Ala Met Lys Arg Glu Tyr Glu Glu
                450                 455                 460 ttt aaa gtg agg ata aat gct ctt gtt gcc aaa gca cag aaa atc cct   1501
Phe Lys Val Arg Ile Asn Ala Leu Val Ala Lys Ala Gln Lys Ile Pro
            465                 470                 475 gaa gaa ggc tgg aca atg cag gat ggt act ccc tgg cct ggt aac aac   1549
Glu Glu Gly Trp Thr Met Gln Asp Gly Thr Pro Trp Pro Gly Asn Asn
480                 485                 490 act aga gat cat cct gga atg ata cag gtg ttc tta ggc cat agt ggg   1597
Thr Arg Asp His Pro Gly Met Ile Gln Val Phe Leu Gly His Ser Gly
    495                 500                 505 ggt ctg gat acc gat gga aat gag ctg cct aga ctc atc tat gtt tct   1645
Gly Leu Asp Thr Asp Gly Asn Glu Leu Pro Arg Leu Ile Tyr Val Ser
510                 515                 520                 525 cgt gaa aag cgg cct gga ttt caa cac cac aaa aag gct gga gct atg   1693
Arg Glu Lys Arg Pro Gly Phe Gln His His Lys Lys Ala Gly Ala Met
                530                 535                 540 aat gca ttg atc cgt gta tct gtt gtt ctt acc aat gga gca tat ctt   1741
Asn Ala Leu Ile Arg Val Ser Val Val Leu Thr Asn Gly Ala Tyr Leu
            545                 550                 555 ttg aac gtg gat tgt gat cat tac ttt aat aac agt aag gct att aaa   1789
Leu Asn Val Asp Cys Asp His Tyr Phe Asn Asn Ser Lys Ala Ile Lys
560                 565                 570
```

-continued

```
gaa gct atg tgt ttc atg atg gac ccg gct att gga aag aag tgc tgc      1837
Glu Ala Met Cys Phe Met Met Asp Pro Ala Ile Gly Lys Lys Cys Cys
    575                 580                 585 tat gtc cag ttc cct caa cgt ttt gac ggt att gat ttg cac gat cga      1885
Tyr Val Gln Phe Pro Gln Arg Phe Asp Gly Ile Asp Leu His Asp Arg
590                 595                 600                 605 tat gcc aac agg aat ata gtc ttt ttc gat att aac atg aag ggg ttg      1933
Tyr Ala Asn Arg Asn Ile Val Phe Phe Asp Ile Asn Met Lys Gly Leu
                610                 615                 620 gat ggt atc cag ggt cca gta tat gtg ggt act ggt tgt tgt ttt aat      1981
Asp Gly Ile Gln Gly Pro Val Tyr Val Gly Thr Gly Cys Cys Phe Asn
                625                 630                 635 agg cag gct cta tat ggg tat gat cct gtt ttg acg gaa gaa gat tta      2029
Arg Gln Ala Leu Tyr Gly Tyr Asp Pro Val Leu Thr Glu Glu Asp Leu
                640                 645                 650 gaa cca aat att att gtc aag agc tgt tgc ggg tca agg aag aaa ggt      2077
Glu Pro Asn Ile Ile Val Lys Ser Cys Cys Gly Ser Arg Lys Lys Gly
    655                 660                 665 aaa agt agc aag aag tat aac tac gaa aag agg aga ggc atc aac aga      2125
Lys Ser Ser Lys Lys Tyr Asn Tyr Glu Lys Arg Arg Gly Ile Asn Arg
670                 675                 680                 685 agt gac tcc aat gct cca ctt ttc aat atg gag gac atc gat gag ggt      2173
Ser Asp Ser Asn Ala Pro Leu Phe Asn Met Glu Asp Ile Asp Glu Gly
                690                 695                 700 ttt gaa ggt tat gat gat gag agg tct att cta atg tcc cag agg agt      2221
Phe Glu Gly Tyr Asp Asp Glu Arg Ser Ile Leu Met Ser Gln Arg Ser
                705                 710                 715 gta gag aag cgt ttt ggt cag tcg ccg gta ttt att gcg gca acc ttc      2269
Val Glu Lys Arg Phe Gly Gln Ser Pro Val Phe Ile Ala Ala Thr Phe
                720                 725                 730 atg gaa caa ggc ggc att cca cca aca acc aat ccc gct act ctt ctg      2317
Met Glu Gln Gly Gly Ile Pro Pro Thr Thr Asn Pro Ala Thr Leu Leu
    735                 740                 745 aag gag gct att cat gtt ata agc tgt ggt tac gaa gac aag act gaa      2365
Lys Glu Ala Ile His Val Ile Ser Cys Gly Tyr Glu Asp Lys Thr Glu
750                 755                 760                 765 tgg ggc aaa gag att ggt tgg atc tat ggt tcc gtg acg gaa gat att      2413
Trp Gly Lys Glu Ile Gly Trp Ile Tyr Gly Ser Val Thr Glu Asp Ile
                770                 775                 780 ctt act ggg ttc aag atg cat gcc cgg ggt tgg ata tcg atc tac tgc      2461
Leu Thr Gly Phe Lys Met His Ala Arg Gly Trp Ile Ser Ile Tyr Cys
                785                 790                 795 aat cct cca cgc cct gcg ttc aag gga tct gca cca atc aat ctt tct      2509
Asn Pro Pro Arg Pro Ala Phe Lys Gly Ser Ala Pro Ile Asn Leu Ser
                800                 805                 810 gat cgt ttg aac caa gtt ctt cga tgg gct ttg gga tct atc gag att      2557
Asp Arg Leu Asn Gln Val Leu Arg Trp Ala Leu Gly Ser Ile Glu Ile
815                 820                 825 ctt ctt agc aga cat tgt cct atc tgg tat ggt tac cat gga agg ttg      2605
Leu Leu Ser Arg His Cys Pro Ile Trp Tyr Gly Tyr His Gly Arg Leu
830                 835                 840                 845 aga ctt ttg gag agg atc gct tat atc aac acc atc gtc tat cct att      2653
Arg Leu Leu Glu Arg Ile Ala Tyr Ile Asn Thr Ile Val Tyr Pro Ile
                850                 855                 860 aca tcc atc cct ctt att gcg tat tgt att ctt ccc gct ttt tgt ctc      2701
Thr Ser Ile Pro Leu Ile Ala Tyr Cys Ile Leu Pro Ala Phe Cys Leu
                865                 870                 875 atc acc gac aga ttc atc ata ccc gag ata agc aac tac gcg agt att      2749
Ile Thr Asp Arg Phe Ile Ile Pro Glu Ile Ser Asn Tyr Ala Ser Ile
```

-continued

```
                    880                 885                 890
tgg ttc att cta ctc ttc atc tca att gct gtg act gga atc ctg gag    2797
Trp Phe Ile Leu Leu Phe Ile Ser Ile Ala Val Thr Gly Ile Leu Glu
    895                 900                 905 ctg aga tgg agc ggt gtg agc att gag gat tgg tgg agg aac gag cag    2845
Leu Arg Trp Ser Gly Val Ser Ile Glu Asp Trp Trp Arg Asn Glu Gln
910                 915                 920                 925 ttc tgg gtc att ggt ggc aca tcc gcc cat ctt ttt gct gtc ttc caa    2893
Phe Trp Val Ile Gly Gly Thr Ser Ala His Leu Phe Ala Val Phe Gln
                930                 935                 940 ggt cta ctt aag gtt ctt gct ggt atc gac acc aac ttc acc gtt aca    2941
Gly Leu Leu Lys Val Leu Ala Gly Ile Asp Thr Asn Phe Thr Val Thr
            945                 950                 955 tct aaa gcc aca gac gaa gat ggg gat ttt gca gaa ctc tac atc ttc    2989
Ser Lys Ala Thr Asp Glu Asp Gly Asp Phe Ala Glu Leu Tyr Ile Phe
        960                 965                 970 aaa tgg aca gct ctt ctc att cca cca acc acc gtc cta ctt gtg aac    3037
Lys Trp Thr Ala Leu Leu Ile Pro Pro Thr Thr Val Leu Leu Val Asn
    975                 980                 985 ctc ata ggc att gtg gct ggt gtc tct tat gct gta aac agt ggc tac    3085
Leu Ile Gly Ile Val Ala Gly Val Ser Tyr Ala Val Asn Ser Gly Tyr
990                 995                 1000                1005 cag tcg tgg ggt ccg ctt ttc ggg aag ctc ttc ttc gcc tta tgg gtt    3133
Gln Ser Trp Gly Pro Leu Phe Gly Lys Leu Phe Phe Ala Leu Trp Val
                1010                1015                1020 att gcc cat ctc tac cct ttc ttg aaa ggt ctg ttg gga aga caa aac    3181
Ile Ala His Leu Tyr Pro Phe Leu Lys Gly Leu Leu Gly Arg Gln Asn
            1025                1030                1035 cga aca cca acc atc gtc att gtc tgg tct gtt ctt ctc gcc tcc atc    3229
Arg Thr Pro Thr Ile Val Ile Val Trp Ser Val Leu Leu Ala Ser Ile
        1040                1045                1050 ttc tcg ttg ctt tgg gtc agg atc aat ccc ttt gtg gac gcc aat ccc    3277
Phe Ser Leu Leu Trp Val Arg Ile Asn Pro Phe Val Asp Ala Asn Pro
    1055                1060                1065 aat gcc aac aac ttc aat ggc aaa gga ggt gtc ttt tagaccctat         3323
Asn Ala Asn Asn Phe Asn Gly Lys Gly Gly Val Phe
1070                1075                1080 ttatatactt gtgtgtgcat atatcaaaaa cgcgcaatgg gaattccaaa tcatctaaac  3383
ccatcaaacc ccagtgaacc gggcagttaa ggtgattcca tgtccaagat tagctttctc  3443
cgagtagcca gagaaggtga aattgttcgt aacactattg taatgatttt ccagtgggga  3503
agaagatgtg gacccaaatg atacatagtc tacaaaaaga atttgttatt ctttcttata  3563
tttattttat ttaaagcttg ttagactcac acttatgtaa tgttggaact tgttgtccta  3623
aaaagggatt ggagttttct ttttatctaa gaatctgaag tttatatgct              3673
```

<210> SEQ ID NO 12
<211> LENGTH: 1081
<212> TYPE: PRT
<213> ORGANISM: Arabidopsis thaliana

<400> SEQUENCE: 12

```
Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45
```

-continued

```
Ala Glu Thr Gly Asp Val Phe Val Ala Cys Asn Glu Cys Ala Phe Pro
     50                  55                  60
Val Cys Arg Pro Cys Tyr Glu Tyr Glu Arg Lys Asp Gly Thr Gln Cys
 65                  70                  75                  80
Cys Pro Gln Cys Lys Thr Arg Phe Arg Arg His Arg Gly Ser Pro Arg
                 85                  90                  95
Val Glu Gly Asp Glu Asp Glu Asp Val Asp Asp Ile Glu Asn Glu
                100                 105                 110
Phe Asn Tyr Ala Gln Gly Ala Asn Lys Ala Arg His Gln Arg His Gly
            115                 120                 125
Glu Glu Phe Ser Ser Ser Arg His Glu Ser Gln Pro Ile Pro Leu
130                 135                 140
Leu Thr His Gly His Thr Val Ser Gly Glu Ile Arg Thr Pro Asp Thr
145                 150                 155                 160
Gln Ser Val Arg Thr Thr Ser Gly Pro Leu Gly Pro Ser Asp Arg Asn
                165                 170                 175
Ala Ile Ser Ser Pro Tyr Ile Asp Pro Arg Gln Pro Val Pro Val Arg
            180                 185                 190
Ile Val Asp Pro Ser Lys Asp Leu Asn Ser Tyr Gly Leu Gly Asn Val
        195                 200                 205
Asp Trp Lys Glu Arg Val Glu Gly Trp Lys Leu Lys Gln Glu Lys Asn
    210                 215                 220
Met Leu Gln Met Thr Gly Lys Tyr His Glu Gly Lys Gly Gly Glu Ile
225                 230                 235                 240
Glu Gly Thr Gly Ser Asn Gly Glu Glu Leu Gln Met Ala Asp Asp Thr
                245                 250                 255
Arg Leu Pro Met Ser Arg Val Val Pro Ile Pro Ser Ser Arg Leu Thr
            260                 265                 270
Pro Tyr Arg Val Val Ile Ile Leu Arg Leu Ile Ile Leu Cys Phe Phe
        275                 280                 285
Leu Gln Tyr Arg Thr Thr His Pro Val Lys Asn Ala Tyr Pro Leu Trp
    290                 295                 300
Leu Thr Ser Val Ile Cys Glu Ile Trp Phe Ala Phe Ser Trp Leu Leu
305                 310                 315                 320
Asp Gln Phe Pro Lys Trp Tyr Pro Ile Asn Arg Glu Thr Tyr Leu Asp
                325                 330                 335
Arg Leu Ala Ile Arg Tyr Asp Arg Asp Gly Glu Pro Ser Gln Leu Val
            340                 345                 350
Pro Val Asp Val Phe Val Ser Thr Val Asp Pro Leu Lys Glu Pro Pro
        355                 360                 365
Leu Val Thr Ala Asn Thr Val Leu Ser Ile Leu Ser Val Asp Tyr Pro
    370                 375                 380
Val Asp Lys Val Ala Cys Tyr Val Ser Asp Asp Gly Ser Ala Met Leu
385                 390                 395                 400
Thr Phe Glu Ser Leu Ser Glu Thr Ala Glu Phe Ala Lys Lys Trp Val
                405                 410                 415
Pro Phe Cys Lys Lys Phe Asn Ile Glu Pro Arg Ala Pro Glu Phe Tyr
            420                 425                 430
Phe Ala Gln Lys Ile Asp Tyr Leu Lys Asp Lys Ile Gln Pro Ser Phe
        435                 440                 445
Val Lys Glu Arg Arg Ala Met Lys Arg Glu Tyr Glu Glu Phe Lys Val
    450                 455                 460
Arg Ile Asn Ala Leu Val Ala Lys Ala Gln Lys Ile Pro Glu Glu Gly
```

```
465                 470                 475                 480
Trp Thr Met Gln Asp Gly Thr Pro Trp Pro Gly Asn Asn Thr Arg Asp
                    485                 490                 495
His Pro Gly Met Ile Gln Val Phe Leu Gly His Ser Gly Gly Leu Asp
                500                 505                 510
Thr Asp Gly Asn Glu Leu Pro Arg Leu Ile Tyr Val Ser Arg Glu Lys
            515                 520                 525
Arg Pro Gly Phe Gln His His Lys Lys Ala Gly Ala Met Asn Ala Leu
        530                 535                 540
Ile Arg Val Ser Val Val Leu Thr Asn Gly Ala Tyr Leu Leu Asn Val
545                 550                 555                 560
Asp Cys Asp His Tyr Phe Asn Asn Ser Lys Ala Ile Lys Glu Ala Met
                565                 570                 575
Cys Phe Met Met Asp Pro Ala Ile Gly Lys Lys Cys Cys Tyr Val Gln
                580                 585                 590
Phe Pro Gln Arg Phe Asp Gly Ile Asp Leu His Asp Arg Tyr Ala Asn
            595                 600                 605
Arg Asn Ile Val Phe Phe Asp Ile Asn Met Lys Gly Leu Asp Gly Ile
        610                 615                 620
Gln Gly Pro Val Tyr Val Gly Thr Gly Cys Cys Phe Asn Arg Gln Ala
625                 630                 635                 640
Leu Tyr Gly Tyr Asp Pro Val Leu Thr Glu Glu Asp Leu Glu Pro Asn
                645                 650                 655
Ile Ile Val Lys Ser Cys Cys Gly Ser Arg Lys Lys Gly Lys Ser Ser
                660                 665                 670
Lys Lys Tyr Asn Tyr Glu Lys Arg Arg Gly Ile Asn Arg Ser Asp Ser
            675                 680                 685
Asn Ala Pro Leu Phe Asn Met Glu Asp Ile Asp Glu Gly Phe Glu Gly
        690                 695                 700
Tyr Asp Asp Glu Arg Ser Ile Leu Met Ser Gln Arg Ser Val Glu Lys
705                 710                 715                 720
Arg Phe Gly Gln Ser Pro Val Phe Ile Ala Ala Thr Phe Met Glu Gln
                725                 730                 735
Gly Gly Ile Pro Pro Thr Thr Asn Pro Ala Thr Leu Leu Lys Glu Ala
                740                 745                 750
Ile His Val Ile Ser Cys Gly Tyr Glu Asp Lys Thr Glu Trp Gly Lys
            755                 760                 765
Glu Ile Gly Trp Ile Tyr Gly Ser Val Thr Glu Asp Ile Leu Thr Gly
        770                 775                 780
Phe Lys Met His Ala Arg Gly Trp Ile Ser Ile Tyr Cys Asn Pro Pro
785                 790                 795                 800
Arg Pro Ala Phe Lys Gly Ser Ala Pro Ile Asn Leu Ser Asp Arg Leu
                805                 810                 815
Asn Gln Val Leu Arg Trp Ala Leu Gly Ser Ile Glu Ile Leu Leu Ser
                820                 825                 830
Arg His Cys Pro Ile Trp Tyr Gly Tyr His Gly Arg Leu Arg Leu Leu
            835                 840                 845
Glu Arg Ile Ala Tyr Ile Asn Thr Ile Val Tyr Pro Ile Thr Ser Ile
        850                 855                 860
Pro Leu Ile Ala Tyr Cys Ile Leu Pro Ala Phe Cys Leu Ile Thr Asp
865                 870                 875                 880
Arg Phe Ile Ile Pro Glu Ile Ser Asn Tyr Ala Ser Ile Trp Phe Ile
                885                 890                 895
```

```
Leu Leu Phe Ile Ser Ile Ala Val Thr Gly Ile Leu Glu Leu Arg Trp
            900                 905                 910

Ser Gly Val Ser Ile Glu Asp Trp Trp Arg Asn Glu Gln Phe Trp Val
            915                 920                 925

Ile Gly Gly Thr Ser Ala His Leu Phe Ala Val Phe Gln Gly Leu Leu
            930                 935                 940

Lys Val Leu Ala Gly Ile Asp Thr Asn Phe Thr Val Thr Ser Lys Ala
945                 950                 955                 960

Thr Asp Glu Asp Gly Asp Phe Ala Glu Leu Tyr Ile Phe Lys Trp Thr
                965                 970                 975

Ala Leu Leu Ile Pro Pro Thr Thr Val Leu Leu Val Asn Leu Ile Gly
            980                 985                 990

Ile Val Ala Gly Val Ser Tyr Ala Val Asn Ser Gly Tyr Gln Ser Trp
            995                1000                1005

Gly Pro Leu Phe Gly Lys Leu Phe Phe Ala Leu Trp Val Ile Ala His
           1010                1015                1020

Leu Tyr Pro Phe Leu Lys Gly Leu Leu Gly Arg Gln Asn Arg Thr Pro
1025                1030                1035                1040

Thr Ile Val Ile Val Trp Ser Val Leu Leu Ala Ser Ile Phe Ser Leu
           1045                1050                1055

Leu Trp Val Arg Ile Asn Pro Phe Val Asp Ala Asn Pro Asn Ala Asn
           1060                1065                1070

Asn Phe Asn Gly Lys Gly Gly Val Phe
           1075                1080

<210> SEQ ID NO 13
<211> LENGTH: 1741
<212> TYPE: DNA
<213> ORGANISM: Oryza sativa
<220> FEATURE:
<221> NAME/KEY: CDS
<222> LOCATION: (101)..(1741)

<400> SEQUENCE: 13
gtgcggccgc cgcgcatcta ggcttgccgc gcgcgcgcgg atctgcgagc tgcgtagccg      60
tttctcgctg tgagtggagg aggaggagga agggaggagg atg gcg gcg aac gcg     115
                                            Met Ala Ala Asn Ala
                                              1               5 ggg atg gtg gcg gga tcc cgc aac cgg aac gag ttc gtc atg atc cgc     163
Gly Met Val Ala Gly Ser Arg Asn Arg Asn Glu Phe Val Met Ile Arg
             10                  15                  20 ccc gac ggc gac gcg cca ccg ccg gct aag cca ggg aag agt gtg aat     211
Pro Asp Gly Asp Ala Pro Pro Pro Ala Lys Pro Gly Lys Ser Val Asn
         25                  30                  35 ggt cag gtc tgc cag att tgt ggc gac act gtt ggc gtc tcg gcc acc     259
Gly Gln Val Cys Gln Ile Cys Gly Asp Thr Val Gly Val Ser Ala Thr
     40                  45                  50 ggc gac gtc ttt gtt gcc tgc aat gag tgc gcc ttc ccg gtc tgc cgc     307
Gly Asp Val Phe Val Ala Cys Asn Glu Cys Ala Phe Pro Val Cys Arg
 55                  60                  65 cct tgc tac gag tac gaa cgc aag gaa ggg aac cag tgc tgc ccc cag     355
Pro Cys Tyr Glu Tyr Glu Arg Lys Glu Gly Asn Gln Cys Cys Pro Gln
 70                  75                  80                  85 tgc aag act aga tac aag agg cac aaa ggt tgc cct aga gtt cag ggc     403
Cys Lys Thr Arg Tyr Lys Arg His Lys Gly Cys Pro Arg Val Gln Gly
                 90                  95                 100 gat gag gaa gaa gaa gat gtt gat gac ctg gac aat gaa ttc cat tat     451
```

-continued

```
                Asp Glu Glu Glu Asp Val Asp Asp Leu Asp Asn Glu Phe His Tyr
                    105                 110                 115 aag cat ggc aat ggc aaa ggt cca gag tgg cag ata cag aga cag ggg        499
Lys His Gly Asn Gly Lys Gly Pro Glu Trp Gln Ile Gln Arg Gln Gly
            120                 125                 130 gaa gat gtt gac ctg tct tca tct tct cgc cac gaa caa cat cgg att        547
Glu Asp Val Asp Leu Ser Ser Ser Ser Arg His Glu Gln His Arg Ile
135                 140                 145 ccc cgt ctg aca agt ggg caa cag atc tca gga gag atc cct gat gct        595
Pro Arg Leu Thr Ser Gly Gln Gln Ile Ser Gly Glu Ile Pro Asp Ala
150                 155                 160                 165 tcc ccc gat cgc cat tct atc cgc agc gga aca tca agc tat gtt gat        643
Ser Pro Asp Arg His Ser Ile Arg Ser Gly Thr Ser Ser Tyr Val Asp
                170                 175                 180 cca agt gtt cca gtt cct gtg agg att gtg gac ccc tcc aag gac ttg        691
Pro Ser Val Pro Val Pro Val Arg Ile Val Asp Pro Ser Lys Asp Leu
            185                 190                 195 aat tcc tat ggg att aac agt gtt gac tgg caa gaa aga gtt gcc agc        739
Asn Ser Tyr Gly Ile Asn Ser Val Asp Trp Gln Glu Arg Val Ala Ser
            200                 205                 210 tgg agg aac aag cag gac aaa aat atg atg cag gta gct aat aaa tat        787
Trp Arg Asn Lys Gln Asp Lys Asn Met Met Gln Val Ala Asn Lys Tyr
215                 220                 225 cca gag gca aga ggg gga gac atg gaa ggg act ggt tca aat ggt gaa        835
Pro Glu Ala Arg Gly Gly Asp Met Glu Gly Thr Gly Ser Asn Gly Glu
230                 235                 240                 245 gat atc caa atg gtt gat gat gca cgt cta cct ctg agc cgc ata gtg        883
Asp Ile Gln Met Val Asp Asp Ala Arg Leu Pro Leu Ser Arg Ile Val
                250                 255                 260 cct atc cct tca aac cag ctc aac ctt tac cgg att gtt atc att ctc        931
Pro Ile Pro Ser Asn Gln Leu Asn Leu Tyr Arg Ile Val Ile Ile Leu
            265                 270                 275 cgt ctt atc atc ctg atg ttc ttc ttc caa tat cgt gtc act cat cca        979
Arg Leu Ile Ile Leu Met Phe Phe Phe Gln Tyr Arg Val Thr His Pro
            280                 285                 290 gtg cgg gat gct tat gga ttg tgg cta gta tct gtt atc tgt gaa att       1027
Val Arg Asp Ala Tyr Gly Leu Trp Leu Val Ser Val Ile Cys Glu Ile
        295                 300                 305 tgg ttg ccc tta tcc tgg ctc cta gat caa ttc cca aag tgg tac ccg       1075
Trp Leu Pro Leu Ser Trp Leu Leu Asp Gln Phe Pro Lys Trp Tyr Pro
310                 315                 320                 325 ata aac cgt gaa aca tac ctt gac agg ctt gca ttg aga tat gat agg       1123
Ile Asn Arg Glu Thr Tyr Leu Asp Arg Leu Ala Leu Arg Tyr Asp Arg
                330                 335                 340 gag gga gag cca tca cag ctt gct ccc att gat gtc ttt gtc agt acg       1171
Glu Gly Glu Pro Ser Gln Leu Ala Pro Ile Asp Val Phe Val Ser Thr
            345                 350                 355 gtg gat cca cta aag gaa cct cct ctg atc aca gca aac act gtt ttg       1219
Val Asp Pro Leu Lys Glu Pro Pro Leu Ile Thr Ala Asn Thr Val Leu
            360                 365                 370 tcc att ctg gct gtg gat tac cct gtt gac aaa gtg tca tgc tat gtt       1267
Ser Ile Leu Ala Val Asp Tyr Pro Val Asp Lys Val Ser Cys Tyr Val
375                 380                 385 tct gac gat ggt tca gct atg tta act ttt gag gct ctg tca gaa act       1315
Ser Asp Asp Gly Ser Ala Met Leu Thr Phe Glu Ala Leu Ser Glu Thr
390                 395                 400                 405 gca gaa ttt gct agg aag tgg gtt ccg ttt tgc aag aag cac aat att       1363
Ala Glu Phe Ala Arg Lys Trp Val Pro Phe Cys Lys Lys His Asn Ile
            410                 415                 420
```

```
gaa cca cga gct cca gag ttt tac ttt gct caa aaa ata gat tac ctg   1411
Glu Pro Arg Ala Pro Glu Phe Tyr Phe Ala Gln Lys Ile Asp Tyr Leu
            425                 430                 435 aag gac aaa atc caa cct tcc ttt gtt aaa gaa agg cgg gca atg aag   1459
Lys Asp Lys Ile Gln Pro Ser Phe Val Lys Glu Arg Arg Ala Met Lys
        440                 445                 450 aga gag tat gaa gaa ttc aag gta cgg atc aat gct ctt gtt gcg aag   1507
Arg Glu Tyr Glu Glu Phe Lys Val Arg Ile Asn Ala Leu Val Ala Lys
    455                 460                 465 gca caa aaa gta cct gaa gag ggg tgg acc atg gct gat ggc act gct   1555
Ala Gln Lys Val Pro Glu Glu Gly Trp Thr Met Ala Asp Gly Thr Ala
470                 475                 480                 485 tgg cct ggg aat aac cca agg gat cac cct ggc atg att cag gtg ttc   1603
Trp Pro Gly Asn Asn Pro Arg Asp His Pro Gly Met Ile Gln Val Phe
                490                 495                 500 ttg ggg cac agt ggt ggg ctt gac act gat ggt aac gag ttg cca cgg   1651
Leu Gly His Ser Gly Gly Leu Asp Thr Asp Gly Asn Glu Leu Pro Arg
            505                 510                 515 ctt gtc tac gtc tct cgt gaa aag agg cca gga ttc cag cat cac aag   1699
Leu Val Tyr Val Ser Arg Glu Lys Arg Pro Gly Phe Gln His His Lys
        520                 525                 530 aag gct ggt gca atg aat gca ttg att cgt gta tct gct gtg           1741
Lys Ala Gly Ala Met Asn Ala Leu Ile Arg Val Ser Ala Val
    535                 540                 545
```

<210> SEQ ID NO 14
<211> LENGTH: 547
<212> TYPE: PRT
<213> ORGANISM: Oryza sativa

<400> SEQUENCE: 14

```
Met Ala Ala Asn Ala Gly Met Val Ala Gly Ser Arg Asn Arg Asn Glu
 1               5                  10                  15

Phe Val Met Ile Arg Pro Asp Gly Asp Ala Pro Pro Ala Lys Pro
            20                  25                  30

Gly Lys Ser Val Asn Gly Gln Val Cys Gln Ile Cys Gly Asp Thr Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg His Lys Gly Cys
                85                  90                  95

Pro Arg Val Gln Gly Asp Glu Glu Glu Asp Val Asp Asp Leu Asp
            100                 105                 110

Asn Glu Phe His Tyr Lys His Gly Asn Gly Lys Gly Pro Glu Trp Gln
        115                 120                 125

Ile Gln Arg Gln Gly Glu Asp Val Asp Leu Ser Ser Ser Arg His
130                 135                 140

Glu Gln His Arg Ile Pro Arg Leu Thr Ser Gly Gln Gln Ile Ser Gly
145                 150                 155                 160

Glu Ile Pro Asp Ala Ser Pro Asp Arg His Ser Ile Arg Ser Gly Thr
                165                 170                 175

Ser Ser Tyr Val Asp Pro Ser Val Pro Val Pro Val Arg Ile Val Asp
            180                 185                 190

Pro Ser Lys Asp Leu Asn Ser Tyr Gly Ile Asn Ser Val Asp Trp Gln
        195                 200                 205
```

```
Glu Arg Val Ala Ser Trp Arg Asn Lys Gln Asp Lys Asn Met Met Gln
    210                 215                 220
Val Ala Asn Lys Tyr Pro Glu Ala Arg Gly Gly Asp Met Glu Gly Thr
225                 230                 235                 240
Gly Ser Asn Gly Glu Asp Ile Gln Met Val Asp Asp Ala Arg Leu Pro
                245                 250                 255
Leu Ser Arg Ile Val Pro Ile Pro Ser Asn Gln Leu Asn Leu Tyr Arg
            260                 265                 270
Ile Val Ile Ile Leu Arg Leu Ile Ile Leu Met Phe Phe Phe Gln Tyr
            275                 280                 285
Arg Val Thr His Pro Val Arg Asp Ala Tyr Gly Leu Trp Leu Val Ser
        290                 295                 300
Val Ile Cys Glu Ile Trp Leu Pro Leu Ser Trp Leu Leu Asp Gln Phe
305                 310                 315                 320
Pro Lys Trp Tyr Pro Ile Asn Arg Glu Thr Tyr Leu Asp Arg Leu Ala
                325                 330                 335
Leu Arg Tyr Asp Arg Glu Gly Glu Pro Ser Gln Leu Ala Pro Ile Asp
            340                 345                 350
Val Phe Val Ser Thr Val Asp Pro Leu Lys Glu Pro Pro Leu Ile Thr
        355                 360                 365
Ala Asn Thr Val Leu Ser Ile Leu Ala Val Asp Tyr Pro Val Asp Lys
    370                 375                 380
Val Ser Cys Tyr Val Ser Asp Asp Gly Ser Ala Met Leu Thr Phe Glu
385                 390                 395                 400
Ala Leu Ser Glu Thr Ala Glu Phe Ala Arg Lys Trp Val Pro Phe Cys
                405                 410                 415
Lys Lys His Asn Ile Glu Pro Arg Ala Pro Glu Phe Tyr Phe Ala Gln
            420                 425                 430
Lys Ile Asp Tyr Leu Lys Asp Lys Ile Gln Pro Ser Phe Val Lys Glu
        435                 440                 445
Arg Arg Ala Met Lys Arg Glu Tyr Glu Glu Phe Lys Val Arg Ile Asn
    450                 455                 460
Ala Leu Val Ala Lys Ala Gln Lys Val Pro Glu Glu Gly Trp Thr Met
465                 470                 475                 480
Ala Asp Gly Thr Ala Trp Pro Gly Asn Asn Pro Arg Asp His Pro Gly
                485                 490                 495
Met Ile Gln Val Phe Leu Gly His Ser Gly Gly Leu Asp Thr Asp Gly
            500                 505                 510
Asn Glu Leu Pro Arg Leu Val Tyr Val Ser Arg Glu Lys Arg Pro Gly
        515                 520                 525
Phe Gln His His Lys Lys Ala Gly Ala Met Asn Ala Leu Ile Arg Val
    530                 535                 540
Ser Ala Val
545

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
agaacagcag atacacgga                                              19
```

```
<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
ctgaagaagg ctggacaat                                              19

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
caatgcattc atagctccag cct                                         23

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
aaaaggctgg agctatgaat gcat                                        24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
tcaccgacag attcatcata cccg                                        24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
gacatggaat caccttaact gcc                                         23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
ccattcagtc ttgtcttcgt aacc                                        24
```

```
<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
ggttacgaag acaagactga aatgg                                   25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
gaacctcata ggcattgtgg gctgg                                   25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
gcaggctcta tatgggtatg atcc                                    24

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
agaacagcag atacacgga                                          19

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
atccgtgtat ctgctgttct tacc                                    24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 27
aatgctcttg ttgccaaagc ac                                      22

<210> SEQ ID NO 28
```

```
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 28
attgtccagc cttcttcagg                                              20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 29
ctgaagaagg ctggacaatg c                                            21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 30
aggtaagcat agctgaacca tc                                           22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 31
agtagattgc agatggtttt ctac                                         24

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 32
ttcaatgggt ccactgtact aac                                          23

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 33
attcagatgc accattgtc                                               19

<210> SEQ ID NO 34
<211> LENGTH: 25
```

```
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_feature
<222> LOCATION: (1)..(25)
<223> OTHER INFORMATION: R is A or G, N is inosine, and Y is C or T.

<400> SEQUENCE: 34
araagatnga ytayytnaar gayaa                                          25

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_feature
<222> LOCATION: (1)..(26)
<223> OTHER INFORMATION: N at positions, 3, 6, 9, and 12, is inosine.
      K at positions 14 and 23,  is G or T, R at position 15
      is A or G,  Y at position 18 is C or T, N at
      positions 21 and 24, is G, A, C or T.

<400> SEQUENCE: 35
atngtnggng tnckrttytg nckncc                                         26

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer
<221> NAME/KEY: misc_feature
<222> LOCATION: (1)..(23)
<223> OTHER INFORMATION: N is inosine, R is A or G, Y is C or T,
      and M is A or C.

<400> SEQUENCE: 36
gcnatgaarm gngantayga rga                                            23

<210> SEQ ID NO 37
<211> LENGTH: 5
<212> TYPE: PRT
<213> ORGANISM: Arabidopsis thaliana
<220> FEATURE:
<221> NAME/KEY: VARIANT
<222> LOCATION: (1)..(5)
<223> OTHER INFORMATION: Xaa at positions 2 and 3 is any amino acid.

<400> SEQUENCE: 37

Gln Xaa Xaa Arg Trp
 1               5
```

MANIPULATION OF CELLULOSE AND/OR β-1,4-GLUCAN

CROSS REFERENCE TO RELATED APPLICATIONS

This application is a continuation of International Patent application PCT/AU97/00402, filed Jun. 24, 1997, which application is incorporated herein and which application claims priority to Australian Patent Application PO 0699, filed Jun. 27, 1996.

The present invention relates generally to isolated genes which encode polypeptides involved in cellulose biosynthesis and transgenic organisms expressing same in sense or antisense orientation, or as ribozymes, co-suppression or gene-targeting molecules. More particularly, the present invention is directed to a nucleic acid molecule isolated from Arabidopsis thaliana, Oryza sativa, wheat, barley, maize, Brassica ssp., Gossypium hirsutum and Eucalyptus ssp. which encode an enzyme which is important in cellulose biosynthesis, in particular the cellulose synthase enzyme and homologues, analogues and derivatives thereof and uses of same in the production of transgenic plants expressing altered cellulose biosynthetic properties.

Bibliographic details of the publications referred to by author in this specification are collected at the end of the description. Sequence identity numbers (SEQ ID Nos.) for the nucleotide and amino acid sequences referred to in the specification are defined after the bibliography.

Throughout the specification, unless the context requires otherwise, the word "comprise", or variations such as "comprises" or "comprising" will be understood to imply the inclusion of a stated element or integer or group of elements or integers but not the exclusion of any other element or integer or group of elements or integers.

Cellulose, the world's most abundant biopolymer, is the most characteristic component of plant cell walls in so far as it forms much of the structural framework of the cell wall. Cellulose is comprised of crystalline β-1,4-glucan microfibrils. The crystalline microfibrils are extremely strong and resist enzymic and mechanical degradation, an important factor in determining the nutritional quantity, digestibility and palatability of animal and human foodstuffs. As cellulose is also the dominant structural component of industrially-important plant fibres, such as cotton, flax, hemp, jute and the timber crops such as Eucalyptus ssp. and Pinus ssp., amongst others, there is considerable economic benefit to be derived from the manipulation of cellulose content and/or quantity in plants. In particular. the production of food and fibre crops with altered cellulose content are highly desirable objectives.

The synthesis of cellulose involves the β-1,4-linkage of glucose monomers, in the form of a nucleoside diphospoglucose such as UDP-glucose, to a pre-existing cellulose chain, catalysed by the enzyme cellulose synthase.

Several attempts to identify the components of the functional cellulose synthase in plants have failed, because levels of β-1,4-glucan or crystalline cellulose produced in such assays have hitherto been too low to permit enzyme purification for protein sequence determination. Insufficient homology between bacterial β-1,4-glucan synthase genes and plant cellulose synthase genes has also prevented the use of hybridisation as an approach to isolating the plant homologues of bacterial β-1,4-glucan (cellulose) synthases.

Furthermore, it has not been possible to demonstrate that the cellulose synthase enzyme from plants is the same as, or functionally related to, other purified and characterised enzymes involved in polysaccharide biosynthesis. As a consequence, the cellulose synthase enzyme has not been isolated from plants and, until the present invention, no nucleic acid molecule has been characterised which functionally-encodes a plant cellulose synthase enzyme.

In work leading up to the present invention, the inventors have generated several novel mutant Arabidopsis thaliana plants which are defective in cellulose biosynthesis. The inventors have further isolated a cellulose synthase gene designated RSW1, which is involved in cellulose biosynthesis in Arabidopsis thaliana, and homologous sequences in Oryza sativa, wheat, barley, maize, Brassica ssp., Gossypium hirsutum and Eucalyptus ssp. The isolated nucleic acid molecules of the present invention provide the means by which cellulose content and structure may be modified in plants to produce a range of useful fibres suitable for specific industrial purposes, for example increased decay resistance of timber and altered digestibility of foodstuffs, amongst others.

Accordingly, one aspect of the present invention provides an isolated nucleic acid molecule comprising a sequence of nucleotides which encodes, or is complementary to a sequence which encodes a polypeptide of the cellulose biosynthetic pathway or a functional homologue, analogue or derivative thereof.

The nucleic acid molecule of the invention may be derived from a prokaryotic source or a eukaryotic source.

Those skilled in the art will be aware that cellulose production requires not only the presence of a catalytic subunit, but also its activation and organisation into arrays which favour the crystallization of glucan chains. This organisation is radically different between bacteria, which possess linear arrays, and higher plants, which possess hexameric clusters or "rosettes", of glucan chains. The correct organisation and activation of the bacterial enzyme may require many factors which are either not known, or alternatively, not known to be present in plant cells, for example specific membrane lipids to impart an active conformation on the enzyme complex or protein, or the bacterial c-di-GMP activation system. Accordingly, the use of a plant-derived sequence in eukaryotic cells such as plants provides significant advantages compared to the use of bacterially-derived sequences.

Accordingly, the present invention does not extend to known genes encoding the catalytic subunit of Agrobacterium tumefaciens or Acetobacter xylinum or Acetobacter pasteurianus cellulose synthase, or the use of such known bacterial genes and polypeptides to manipulate cellulose.

Preferably, the subject nucleic acid molecule is derived from an eukaryotic organism.

In a more preferred embodiment of the invention, the isolated nucleic acid molecule of the invention encodes a plant cellulose synthase or a catalytic subunit thereof, or a homologue, analogue or derivative thereof.

More preferably, the isolated nucleic acid molecule encodes a plant cellulose synthase polypeptide which is associated with the primary cell wall of a plant cell. In an alternative preferred embodiment, the nucleic acid molecule of the invention encodes a plant cellulose synthase or catalytic subunit thereof which is normally associated with the secondary cell wall of a plant cell.

In a more preferred embodiment, the nucleic acid molecule of the invention is a cDNA molecule, genomic clone, mRNA molecule or a synthetic oligonucleotide molecule.

In a particularly preferred embodiment, the present invention provides an isolated nucleic acid molecule which encodes or is complementary to a nucleic acid molecule which encodes the *Arabidopsis thaliana, Gossypium hirsutum* (cotton), *Oryza sativa* (rice), Eucalyptus ssp., Brassica ssp. wheat, barley or maize cellulose synthase enzyme or a catalytic subunit thereof or a polypeptide component, homologue, analogue or derivative thereof.

As exemplified herein, the present inventors have identified cellulose biosynthesis genes in maize, wheat, barley, rice, cotton, Brassica ssp. and Eucalyptus ssp., in addition to the specific *Arabidopsis thaliana* RSW1 gene sequence which has been shown to be particularly useful for altering cellulose and/or β-1,4-glucan and/or starch levels in cells.

Hereinafter the term "polypeptide of the cellulose biosynthetic pathway" or similar term shall be taken to refer to a polypeptide or a protein or a part, homologue, analogue or derivative thereof which is involved in one or more of the biosynthetic steps leading to the production of cellulose or any related β-1,4-glucan polymer in plants. In the present context, a polypeptide of the cellulose biosynthetic pathway shall also be taken to include both an active enzyme which contributes to the biosynthesis of cellulose or any related β-1,4-glucan polymer in plants and to a polypeptide component of such an enzyme. As used herein, a polypeptide of the cellulose biosynthetic pathway thus includes cellulose synthase. Those skilled in the art will be aware of other cellulose biosynthetic pathway polypeptides in plants.

The term "related β-1,4-glucan polymer" shall be taken to include any carbohydrate molecule comprised of a primary structure of β-1,4-linked glucose monomers similar to the structure of the components of the cellulose microfibril, wherein the relative arrangement or relative configuration of the glucan chains may differ from their relative configuration in microfibrils of cellulose. As used herein, a related β-1,4-glucan polymer includes those β-1,4-glucan polymers wherein individual β-1,4-glucan microfibrils are arranged in an anti-parallel or some other relative configuration not found in a cellulose molecule of plants and those non-crystalline β-1,4-glucans described as lacking the resistance to extraction and degradation that characterise cellulose microfibrils.

The term "cellulose synthase" shall be taken to refer to a polypeptide which is required to catalyse a β-1,4-glucan linkage to a cellulose microfibril.

Reference herein to "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term "gene" is also used to describe synthetic or fusion molecules encoding all or part of a functional product.

In the present context, the term "cellulose gene" or "cellulose genetic sequence" or similar term shall be taken to refer to any gene as hereinbefore defined which encodes a polypeptide of the cellulose biosynthetic pathway and includes a cellulose synthase gene.

The term "cellulose synthase gene" shall be taken to refer to any cellulose gene which specifically encodes a polypeptide which is a component of a functional enzyme having cellulose synthase activity i.e. an enzyme which catalyses a β-1,4-glucan linkage to a cellulose microfibril.

Preferred cellulose genes may be derived from a naturally-occurring cellulose gene by standard recombinant techniques. Generally, a cellulose gene may be subjected to mutagenesis to produce single or multiple nucleotide substitutions, deletions and/or additions. Nucleotide insertional derivatives of the cellulose synthase gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

As used herein, the term "derived from" shall be taken to indicate that a particular integer or group of integers has originated from the species specified, but has not necessarily been obtained directly from the specified source.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

The present invention extends to the isolated nucleic acid molecule when integrated into the genome of a cell as an addition to the endogenous cellular complement of cellulose synthase genes. The said integrated nucleic acid molecule may, or may not, contain promoter sequences to regulate expression of the subject genetic sequence.

The isolated nucleic acid molecule of the present invention may be introduced into and expressed in any cell, for example a plant cell, fungal cell, insect cell. animal cell, yeast cell or bacterial cell. Those skilled in the art will be aware of any moficiations which are required to the codon usage or promoter sequences or other regulatory sequences, in order for expression to occur in such cells.

Another aspect of the present invention is directed to a nucleic acid molecule which comprises a sequence of nucleotides corresponding or complementary to any one or more of the sequences set forth in SEQ ID Nos:1, 3, 4, 5, 7, 9, 11, or 13, or having at least about 40%, more preferably at least about 55%, still more preferably at least about 65%, yet still more preferably at least about 75–80% and even still more preferably at least about 85–95% nucleotide similarity to all, or a part thereof.

According to this aspect of the invention, said nucleic acid molecule encodes, or is complementary to a nucleotide sequence encoding, a polypeptide of the cellulose biosynthetic pathway in a plant or a homologue. analogue or derivative thereof.

Preferably, a nucleic acid molecule which is at least 40% related to any one or more of the sequences set forth in SEQ ID Nos:1, 3, 4, 5, 7, 9, 11, or 13 comprises a nucleotide sequence which encodes or is complementary to a sequence which encodes a plant cellulose synthase, more preferably a cellulose synthase which is associated with the primary or the secondary plant cell wall of the species from which it has been derived.

Furthermore, the nucleic acid molecule according to this aspect of the invention may be derived from a monocotyledonous or dicotyledonous plant species. In a particularly preferred embodiment, the nucleic acid molecule is derived from *Arabidopsis thaliana, Oryza sativa,* wheat, barley, maize, Brassica ssp., *Gossypium hirsutum* (cotton) or Eucalyptus ssp., amongst others.

For the purposes of nomenclature, the nucleotide sequence shown in SEQ ID NO:1 relates to a cellulose gene as hereinbefore defined which comprises a cDNA sequence designated T20782 and which is derived from *Arabidopsis thaliana*. The amino acid sequence set forth in SEQ ID NO:2 relates to the polypeptide encoded by T20782.

The nucleotide sequence set forth in SEQ ID NO:3 relates to the nucleotide sequence of the complete *Arabidopsis thaliana* genomic gene RSW1, including both intron and exon sequences. The nucleotide sequence of SEQ ID NO:3 comprises exons 1–14 of the genomic gene and includes 2295 bp of 5'-untranslated sequences, of which approximately the first 1.9 kb comprises RSW1 promoter sequence (there is a putative TATA box motif at positions 1843–1850 of SEQ ID NO:3). The nucleotide sequence set forth in SEQ ID NO:3 is derived from the cosmid clone 23H12. This sequence is also the genomic gene equivalent of SEQ ID Nos:1 and 5.

The nucleotide sequence set forth in SEQ ID NO:4 relates to the partial nucleotide sequence of a genomic gene variant of RSW1, derived from cosmid clone 12C4. The nucleotide sequence of SEQ ID NO:4 comprises exon sequence 1–11 and part of exon 12 of the genomic gene sequence and includes 862 bp of 5'-untranslated sequences, of which approximately 700 nucleotides comprise RSW1 promoter sequences (there is a putative TATA box motif at positions 668–673 of SEQ ID NO:4). The genomic gene sequence set forth in SEQ ID NO:4 is the equivalent of the cDNA sequence set forth in SEQ ID NO:7 (i.e. cDNA clone Ath-A).

The nucleotide sequence shown in SEQ ID NO:5 relates to a cellulose gene as hereinbefore defined which comprises a cDNA equivalent of the *Arabidopsis thaliana* RSW1 gene set forth in SEQ ID NO:3. The amino acid sequence set forth in SEQ ID NO:6 relates to the polypeptide encoded by the wild-type RSW1 gene sequences set forth in SEQ ID Nos:3 and 5.

The nucleotide sequence shown in SEQ ID NO:7 relates to a cellulose gene as hereinbefore defined which comprises a cDNA equivalent of the *Arabidopsis thaliana* RSW1 gene set forth in SEQ ID NO:4. The nucleotide sequence is a variant of the nucleotide sequences set forth in SEQ ID Nos:3 and 5. The amino acid sequence set forth in SEQ ID NO:8 relates to the polypeptide encoded by the wild-type RSW1 gene sequences set forth in SEQ ID Nos:4 and 6.

The nucleotide sequence shown in SEQ ID NO:9 relates to a cellulose gene as hereinbefore defined which comprises a further wild-type variant of the *Arabidopsis thaliana* RSW1 gene set forth in SEQ ID Nos:3 and 5. The nucleotide sequence variant is designated Ath-B. The amino acid sequence set forth in SEQ ID NO:10 relates to the polypeptide encoded by the wild-type RSW1 gene sequence set forth in SEQ ID No:9.

The nucleotide sequence shown in SEQ ID NO:11 relates to a cellulose gene as hereinbefore defined which comprises a cDNA equivalent of the *Arabidopsis thaliana* rsw1 gene. The rsw1 gene is a mutant cellulose gene which produces a radial root swelling phenotype as described by Baskin et al (1992). The present inventors have shown herein that the rsw1 gene also produces reduced inflorescence length, reduced fertility, misshapen epidermal cells, reduced cellulose content and the accumulation of non-crystalline β-1,4-glucan, amongst others, when expressed in plant cells. The rsw1 nucleotide sequence is a further variant of the nucleotide sequences set forth in SEQ ID Nos:3 and 5. The amino acid sequence set forth in SEQ ID NO:12 relates to the rsw1 polypeptide encoded by the mutant rsw1 gene sequence set forth in SEQ ID No:11.

The nucleotide sequence shown in SEQ ID NO:13 relates to a cellulose gene as hereinbefore defined which comprises a cDNA equivalent of the *Oryza sativa* RSW1 or RSW1-like gene. The nucleotide sequence is closely-related to the *Arabidopsis thaliana* RSW1 and rsw1 nucleotide sequences set forth herein (SEQ ID Nos:1, 3, 4, 5, 7, 9 and 11). The amino acid sequence set forth in SEQ ID NO:14 relates to the polypeptide encoded by the RSW1 or RSW1-like gene sequences set forth in SEQ ID No: 13.

Those skilled in the art will be aware of procedures for the isolation of further cellulose genes to those specifically described herein, for example further cDNA sequences and genomic gene equivalents, when provided with one or more of the nucleotide sequences set forth in SEQ ID Nos:1, 3, 4, 5, 7, 9, 11, or 13. In particular, hybridisations may be performed using one or more nucleic acid hybridisation probes comprising at least 10 contiguous nucleotides and preferably at least 50 contiguous nucleotides derived from the nucleotide sequences set forth herein, to isolate cDNA clones, mRNA molecules, genomic clones from a genomic library (in particular genomic clones containing the entire 5' upstream region of the gene including the promoter sequence, and the entire coding region and 3'-untranslated sequences), and/or synthetic oligonucleotide molecules, amongst others. The present invention clearly extends to such related sequences.

The invention further extends to any homologues, analogues or derivatives of any one or more of SEQ ID Nos:1, 3, 4, 5, 7, 9, 11 or 13.

A further aspect of the present invention contemplates a nucleic acid molecule which encodes or is complementary to a nucleic acid molecule which encodes, a polypeptide which is required for cellulose biosynthesis in a plant, such as cellulose synthase, and which is capable of hybridising under at least low stringency conditions to the nucleic acid molecule set forth in any one or more of SEQ ID Nos:1, 3, 4, 5, 7, 9, 1 1 or 13, or to a complementary strand thereof.

As an exemplification of this embodiment, the present inventors have shown that it is possible to isolate variants of the Arabidopsis thaliana RSW1 gene sequence set forth in SEQ ID NO:3, by hybridization under low stringency conditions. Such variants include related sequences derived from Gossypium hirsutum (cotton), Eucalyptus ssp. and A. thaliana. Additional variant are clearly encompassed by the present invention.

Preferably, the nucleic acid molecule further comprises a nucleotide sequence which encodes, or is complementary to a nucleotide sequence which encodes, a cellulose synthase polypeptide, more preferably a cellulose synthase which is associated with the primary or secondary plant cell wall of the plant species from which said nucleic acid molecule was derived.

More preferably, the nucleic acid molecule according to this aspect of the invention encodes or is complementary to a nucleic acid molecule which encodes, a polypeptide which is required for cellulose biosynthesis in a plant, such as cellulose synthase, and which is capable of hybridising under at least medium stringency conditions to the nucleic acid molecule set forth in any one or more of SEQ ID Nos:1, 3, 4, 5, 7, 9, 11 or 13, or to a complementary strand thereof.

Even more preferably, the nucleic acid molecule according to this aspect of the invention encodes or is complementary to a nucleic acid molecule which encodes, a polypeptide which is required for cellulose biosynthesis in a plant, such as cellulose synthase, and which is capable of hybridising under at least high stringency conditions to the nucleic acid molecule set forth in any one or more of SEQ ID Nos:1, 3, 4, 5, 7, 9, 11 or 13, or to a complementary strand thereof.

For the purposes of defining the level of stringency, a low stringency is defined herein as being a hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. A medium stringency comprises a hybridisation and/or a wash carried out in 0.2×SSC–2× SSC buffer, 0.1% (w/v) SDS at 42° C. to 65° C., while a high stringency comprises a hybridisation and/or a wash carried out in 0.1×SSC–0.2×SSC buffer, 0.1% (w/v) SDS at a temperature of at least 55° C. Conditions for hybridisations and washes are well understood by one normally skilled in the art. For the purposes of further clarification only, reference to the parameters affecting hybridisation between nucleic acid molecules is found in pages 2.10.8 to 2.10.16. of Ausubel et al. (1987), which is herein incorporated by reference.

In an even more preferred embodiment of the invention, the isolated nucleic acid molecule further comprises a sequence of nucleotides which is at least 40% identical to at least 10 contiguous nucleotides derived from any one or more of SEQ ID Nos:1, 3, 4, 5, 7, 9, 11 or 13, or a complementary strand thereof.

Still more preferably, the isolated nucleic acid molecule further comprises a sequence of nucleotides which is at least 40% identical to at least 50 contiguous nucleotides derived from the sequence set forth in any one or more of SEQ ID Nos:1, 3, 4, 5, 7, 9, 11 or 13, or a complementary strand thereof.

The present invention is particularly directed to a nucleic acid molecule which is capable of functioning as a cellulose gene as hereinbefore defined, for example a cellulose synthase gene such as, but not limited to, the Arabidopsis thaliana, Oryza sativa, wheat, barley, maize, Brassica ssp., Gossypium hirsutum or Eucalyptus ssp. cellulose synthase genes, amongst others. The subject invention clearly contemplates additional cellulose genes to those specifically described herein which are derived from these plant species.

The invention further contemplates other sources of cellulose genes such as but not limited to, tissues and cultured cells of plant origin. Preferred plant species according to this embodiment include hemp, jute, flax and woody plants including, but not limited to Pinus ssp., Populus ssp., Picea spp., amongst others.

A genetic sequence which encodes or is complementary to a sequence which encodes a polypeptide which is involved in cellulose biosynthesis may correspond to the naturally occurring sequence or may differ by one or more nucleotide substitutions, deletions and/or additions. Accordingly, the present invention extends to cellulose genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules.

In a particularly preferred embodiment, the cellulose genetic sequences are employed to identify and isolate similar genes from plant cells, tissues, or organ types of the same species, or from the cells, tissues, or organs of another plant species.

According to this embodiment, there is contemplated a method for identifying a related cellulose gene or related cellulose genetic sequence, for example a cellulose synthase or cellulose synthase-like gene, said method comprising contacting genomic DNA, or mRNA, or cDNA with a hybridisation effective amount of a first cellulose genetic sequence comprising any one or more of SEQ ID Nos:1, 3, 4, 5, 7, 9, 11 or 13, or a complementary sequence. homologue, analogue or derivative thereof derived from at least 10 contiguous nucleotides of said first sequence, and then detecting said hybridisation.

Preferably, the first genetic sequence comprises at least 50 contiguous nucleotides, even more preferably at least 100 contiguous nucleotides and even more preferably at least 500 contiguous nucleotides, derived from any one or more of SEQ ID Nos:1, 3, 4, 5, 7, 9, 11 or 13, or a complementary strand, homologue, analogue or derivative thereof.

The related cellulose gene or related cellulose genetic sequence may be in a recombinant form, in a virus particle, bacteriophage particle, yeast cell, animal cell, or a plant cell. Preferably, the related cellulose gene or related cellulose genetic sequence is derived from a plant species, such as a monocotyledonous plant or a dicotyledonous plant selected from the list comprising Arabidopsis thaliana, wheat, barley, maize, Brassica ssp., Gossypium hirsutum (cotton), Oryza sativa (rice), Eucalyptus ssp., hemp, jute, flax, and woody plants including, but not limited to Pinus ssp., Populus ssp., Picea spp., amongst others.

More preferably, related cellulose gene or related cellulose genetic sequence is derived from a plant which is useful in the fibre or timber industries, for example Gossypium hirsutum (cotton), hemp, jute, flax, Eucalyptus ssp. or Pinus ssp., amongst others. Alternatively, the related cellulose gene or related cellulose genetic sequence is derived from a plant which is useful in the cereal or starch industry, for example wheat, barley, rice or maize, amongst others.

In a particularly preferred embodiment, the first cellulose genetic sequence is labelled with a reporter molecule capable of giving an identifiable signal (e.g. a radioisotope such as $^{32}P$ or $^{35}S$ or a biotinylated molecule).

An alternative method contemplated in the present invention involves hybridising two nucleic acid "primer molecules" to a nucleic acid "template molecule" which comprises a related cellulose gene or related cellulose genetic sequence or a functional part thereof, wherein the first of said primers comprises contiguous nucleotides derived from any one or more of SEQ ID Nos:1, 3, 4, 5. 7, 9, 11 or 13 or a homologue, analogue or derivative thereof and the second of said primers comprises contiguous nucleotides complementary to any one or more of SEQ ID Nos:1, 3, 4, 5, 7, 9, 11 or 13. Specific nucleic acid molecule copies of the template molecule are amplified enzymatically in a polymerase chain reaction, a technique that is well known to one skilled in the art.

In a preferred embodiment, each nucleic acid primer molecule is at least 10 nucleotides in length, more preferably at least 20 nucleotides. in length, even more preferably at least 30 nucleotides in length, still more preferably at least 40 nucleotides in length and even still more preferably at least 50 nucleotides in length.

Furthermore, the nucleic acid primer molecules consists of a combination of any of the nucleotides adenine, cytidine, guanine, thymidine, or inosine, or functional analogues or derivatives thereof which are at least capable of being incorporated into a polynucleotide molecule without having an inhibitory effect on the hybridisation of said primer to the template molecule in the environment in which it is used.

Furthermore, one or both of the nucleic acid primer molecules may be contained in an aqueous mixture of other nucleic acid primer molecules, for example a mixture of degenerate primer sequences which vary from each other by one or more nucleotide substitutions or deletions. Alternatively, one or both of the nucleic acid primer molecules may be in a substantially pure form.

The nucleic acid template molecule may be in a recombinant form, in a virus particle, bacteriophage particle, yeast cell, animal cell, or a plant cell. Preferably, the nucleic acid template molecule is derived from a plant cell, tissue or organ, in particular a cell, tissue or organ derived from a plant selected from the list comprising *Arabidopsis thaliana, Oryza sativa,* wheat, barley, maize, Brassica ssp., *Gossypium hirsutum* and Eucalyptus ssp., hemp, jute, flax, and woody plants including, but not limited to Pinus ssp., Populus ssp., Picea spp., amongst others.

Those skilled in the art will be aware that there are many known variations of the basic polymerase chain reaction procedure, which may be employed to isolate a related cellulose gene or related cellulose genetic sequence when provided with the nucleotide sequences set forth in any one or more of SEQ ID Nos:1, 3, 4, 5, 7, 9, 11 or 13. Such variations are discussed, for example, in McPherson et al (1991). The present invention extends to the use of all such variations in the isolation of related cellulose genes or related cellulose genetic sequences using the nucleotide sequences embodied by the present invention.

The isolated nucleic acid molecule according to any of the further embodiments may be cloned into a plasmid or bacteriophage molecule, for example to facilitate the preparation of primer molecules or hybridisation probes or for the production of recombinant gene products. Methods for the production of such recombinant plasmids, cosmids, bacteriophage molecules or other recombinant molecules are well-known to those of ordinary skill in the art and can be accomplished without undue experimentation. Accordingly, the invention further extends to any recombinant plasmid, bacteriophage, cosmid or other recombinant molecule comprising the nucleotide sequence set forth in any one or more of SEQ ID Nos:1, 3, 4, 5, 7, 9, 11 or 13, or a complementary sequence, homologue, analogue or derivative thereof.

The nucleic acid molecule of the present invention is also useful for developing genetic constructs which express a cellulose genetic sequence, thereby providing for the increased expression of genes involved in cellulose biosynthesis in plants, selected for example from the list comprising *Arabidopsis thaliana, Oryza sativa,* wheat, barley, maize, Brassica ssp., *Gossypium hirsutum* and Eucalyptus ssp., hemp, jute, flax, and woody plants including, but not limited to Pinus ssp., Populus ssp., Picea spp., amongst others. The present invention particularly contemplates the modification of cellulose biosynthesis in cotton, hemp, jute, flax, Eucalyptus ssp. and Pinus ssp. amongst others.

The present inventors have discovered that the genetic sequences disclosed herein are capable of being used to modify the level of non-crystalline β-1,4,-glucan, in addition to altering cellulose levels when expressed, particularly when expressed in plants cells. In particular, the *Arabidopsis thaliana* rsw1 mutant has increased levels of non-crystalline β-1,4,-glucan, when grown at 31° C. compared to wild-type plants, grown under identical conditions. The expression of a genetic sequence described herein in the antisense orientation in transgenic plants grown at only 21° C. is shown to reproduce many aspects of the rsw1 mutant phenotype. Accordingly, the present invention clearly extends to the modification of non-crystalline β-1,4,-glucan biosynthesis in plants, selected for example from the list comprising *Arabidopsis thaliana, Oryza sativa,* wheat, barley, maize, Brassica ssp., *Gossypium hirsutum* and Eucalyptus ssp., hemp, jute, flax, and woody plants including, but not limited to Pinus ssp., Populus ssp., Picea spp., amongst others. The present invention particularly contemplates the modification of non-crystalline β-1,4,-glucan biosynthesis in cotton, hemp, jute, flax, Eucalyptus ssp. and Pinus ssp., amongst others.

The present invention further extends to the production and use of non-crystalline β-1,4-glucan and to the use of the glucan to modify the properties of plant cell walls or cotton fibres or wood fibres. Such modified properties are described herein (Example 13).

The inventors have discovered that the rsw1 mutant has altered carbon partitioning compared to wild-type plants, resulting in significantly higher starch levels therein. The isolated nucleic acid molecules provided herein are further useful for altering the carbon partitioning in a cell. In particular, the present invention contemplates increased starch production in transgenic plants expressing the nucleic acid molecule of the invention in the antisense orientation or alternatively, expressing a ribozyme or co-suppression molecule comprising the nucleic acid sequence of the invention.

The invention further contemplates reduced starch and/or non-crystalline β-1,4-glucan product in transgenic plants expressing the nucleic acid molecule of the invention in the sense orientation such that cellulose production is increased therein.

Wherein it is desired to increase cellulose production in a plant cell, the coding region of a cellulose gene is placed operably behind a promoter, in the sense orientation, such that a cellulose gene product is capable of being expressed under the control of said promoter sequence. In a preferred embodiment, the cellulose genetic sequence is a cellulose synthase genomic sequence, cDNA molecule or protein-coding sequence.

In a particularly preferred embodiment, the cellulose genetic sequence comprises a sequence of nucleotides substantially the same as the sequence set forth in any one or more of SEQ ID Nos:1, 3, 4, 5, 7, 9, 11 or 13 or a homologue, analogue or derivative thereof.

Wherein it is desirable to reduce the content of cellulose or to increase the content of non-crystalline β-1,4-glucan, the nucleic acid molecule of the present invention is expressed in the antisense orientation under the control of a suitable promoter. Additionally, the nucleic acid molecule of the invention is also useful for developing ribozyme molecules, or in co-suppression of a cellulose gene. The expression of an antisense, ribozyme or co-suppression molecule comprising a cellulose gene, in a cell such as a plant cell, fungal cell, insect cell, animal cell, yeast cell or bacterial cell, may also increase the solubility, digestibility or extractability of metabolites from plant tissues or alternatively, or increase the availability of carbon as a precursor for any secondary metabolite other than cellulose (e.g. starch or sucrose). By targeting the endogenous cellulose gene, expression is diminished, reduced or otherwise lowered to a level that results in reduced deposition of cellulose in the primary or secondary cell walls of the plant cell, fungal cell, insect cell, animal cell, yeast cell or bacterial cell, and more particularly, a plant cell. Additionally, or alternatively, the content of non-crystalline β-1,4-glucan is increased in such cells.

Co-suppression is the reduction in expression of an endogenous gene that occurs when one or more copies of said gene, or one or more copies of a substantially similar gene are introduced into the cell. The present invention also extends to the use of co-suppression to inhibit the expression of a gene which encodes a cellulose gene product, such as but not limited to cellulose synthase. Preferably, the co-suppression molecule of the present invention targets a plant mRNA molecule which encodes a cellulose synthase enzyme, for example a plant, fungus, or bacterial cellulose synthase mRNA, and more preferably a plant mRNA derived from *Arabidopsis thaliana, Oryza saliva,* wheat, barley, maize, Brassica ssp., *Gossypium hirsutum* and Eucalyptus ssp., hemp, jute, flax, or a woody plant such as Pinus ssp., Populus ssp., or Picea spp., amongst others.

In a particularly preferred embodiment, the gene which is targeted by a co-suppression molecule, comprises a sequence of nucleotides set forth in any one or more of SEQ ID Nos:1, 3, 4, 5, 7, 9, 11 or 13, or a complement, homologue, analogue or derivative thereof.

In the context of the present invention, an antisense molecule is an RNA molecule which is transcribed from the complementary strand of a nuclear gene to that which is normally transcribed to produce a "sense" mRNA molecule capable of being translated into a polypeptide component of the cellulose biosynthetic pathway. The antisense molecule is therefore complementary to the mRNA transcribed from a sense cellulose gene or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a polypeptide gene product.

Preferably, the antisense molecule of the present invention targets a plant mRNA molecule which encodes a cellulose gene product, for example cellulose synthase. Preferably, the antisense molecule of the present invention targets a plant mRNA molecule which encodes a cellulose synthase enzyme, for example a plant mRNA derived from *Arabidopsis thaliana, Oryza saliva,* wheat, barley, maize, Brassica ssp., *Gossypium hirsutum* and Eucalyptus ssp., hemp, jute, flax, or a woody plant such as Pinus ssp., Populus ssp., or Picea spp., amongst others.

In a particularly preferred embodiment, the antisense molecule of the invention targets an mRNA molecule encoded by any one or more of SEQ ID Nos:1, 3, 4, 5, 7, 9, 11 or 13, or a homologue, analogue or derivative thereof.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852.

The present invention extends to ribozyme which target a sense mRNA encoding a cellulose gene product, thereby hybridising to said sense mRNA and cleaving it, such that it is no longer capable of being translated to synthesise a functional polypeptide product. Preferably, the ribozyme molecule of the present invention targets a plant mRNA molecule which encodes a cellulose synthase enzyme, for example a plant mRNA derived from *Arabidopsis thaliana, Gossypium hirsutum* (cotton), *Oryza sativa* (rice), Eucalyptus ssp., hemp, jute, flax, or a woody plant such as Pinus ssp., Populus ssp., or Picea spp., amongst others.

In a particularly preferred embodiment, the ribozyme molecule will target an mRNA encoded by any one or more of SEQ ID Nos:1, 3, 4, 5, 7, 9, 11 or 13, or a homologue, analogue or derivative thereof.

According to this embodiment, the present invention provides a ribozyme or antisense molecule comprising at least 5 contiguous nucleotide bases derived from any one or more of SEQ ID Nos:1, 3, 4, 5, 7, 9, 11 or 13, or a complementary nucleotide sequence or a homologue, analogue or derivative thereof, wherein said antisense or ribozyme molecule is able to form a hydrogen-bonded complex with a sense mRNA encoding a cellulose gene product to reduce translation thereof.

In a preferred embodiment, the antisense or ribozyme molecule comprises at least 10 to 20 contiguous nucleotides derived from any one or more of SEQ ID Nos:1, 3, 4, 5, 7, 9, 11 or 13, or a complementary nucleotide sequence or a homologue, analogue or derivative thereof. Although the preferred antisense and/or ribozyme molecules hybridise to at least about 10 to 20 nucleotides of the target molecule, the present invention extends to molecules capable of hybridising to at least about 50–100 nucleotide bases in length, or a molecule capable of hybridising to a full-length or substantially full-length mRNA encoded by a cellulose gene, such as a cellulose synthase gene.

Those skilled in the art will be aware of the necessary conditions, if any, for selecting or preparing the antisense or ribozyme molecules of the invention.

It is understood in the art that certain modifications, including nucleotide substitutions amongst others, may be made to the antisense and/or ribozyme molecules of the present invention, without destroying the efficacy of said molecules in inhibiting the expression of a gene encoding a cellulose gene product such as cellulose synthase. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridising to a sense mRNA molecule which encodes a cellulose gene product.

Gene targeting is the replacement of an endogenous gene sequence within a cell by a related DNA sequence to which it hybridises, thereby altering the form and/or function of the endogenous gene and the subsequent phenotype of the cell. According to this embodiment, at least a part of the DNA sequence defined by any one or more of SEQ ID Nos:1, 3, 4, 5, 7, 9, 11 or 13, or a related cellulose genetic sequence, may be introduced into target cells containing an endogenous cellulose gene, thereby replacing said endogenous cellulose gene.

According to this embodiment, the polypeptide product of said cellulose genetic sequence possesses different catalytic activity and/or expression characteristics, producing in turn modified cellulose deposition in the target cell. In a particularly preferred embodiment of the invention, the endogenous cellulose gene of a plant is replaced with a gene which is merely capable of producing non-crystalline β-1,4-glucan polymers or alternatively which is capable of producing a modified cellulose having properties similar to synthetic fibres such as rayon, in which the β-1,4-glucan polymers are arranged in an antiparallel configuration relative to one another.

The present invention extends to genetic constructs designed to facilitate expression of a cellulose genetic sequence which is identical, or complementary to the sequence set forth in any one or more of SEQ ID Nos:1, 3, 4, 5, 7, 9, 11 or 13, or a functional derivative, part, homologue, or analogue thereof, or a genetic construct designed to facilitate expression of a sense molecule, an antisense molecule, ribozyme molecule, co-suppression molecule, or gene targeting molecule containing said genetic sequence.

The said genetic construct of the present invention comprises the foregoing sense, antisense, or ribozyme, or co-suppression nucleic acid molecule, or gene-targeting molecule, placed operably under the control of a promoter sequence capable of regulating the expression of the said nucleic acid molecule in a prokaryotic or eukaryotic cell, preferably a plant cell. The said genetic construct optionally comprises, in addition to a promoter and sense, or antisense, or ribozyme, or co-suppression, or gene-targeting nucleic acid molecule, a terminator sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants. Examples of terminators particularly suitable for use in the genetic constructs of the present invention include the nopaline synthase (NOS) gene terminator of *Agrobacterium tumefaciens,* the terminator of the Cauliflower mosaic virus (CaMV) 35S gene, and the zein gene terminator from *Zea mays.*

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of said sense, antisense, or ribozyme, or co-suppression nucleic acid molecule, in a plant cell. Preferred promoters may contain additional copies of one or more specific regulatory elements, to further enhance expression of a sense antisense, ribozyme or co-suppression molecule and/or to alter the spatial expression and/or temporal expression of said sense or antisense, or ribozyme, or co-suppression, or gene-targeting molecule. For example, regulatory elements which confer copper inducibility may be placed adjacent to a heterologous promoter sequence driving expression of a sense, or antisense, or ribozyme, or co-suppression, or gene-targeting molecule, thereby conferring copper inducibility on the expression of said molecule.

Placing a sense or ribozyme, or antisense, or co-suppression, or gene-targeting molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include viral, fungal, bacterial, animal and plant derived promoters capable of functioning in prokaryotic or eukaryotic cells. Preferred promoters are those capable of regulating the expression of the subject cellulose genes of the invention in plants cells, fungal cells, insect cells, yeast cells, animal cells or bacterial cells, amongst others. Particularly preferred promoters are capable of regulating expression of the subject nucleic acid molecules in plant cells. The promoter may regulate the expression of the said molecule constitutively, or differentially with respect to the tissue in which expression occurs or, with respect to the developmental stage at which expression occurs, or in response to external stimuli such as physiological stresses, or plant pathogens, or metal ions, amongst others. Preferably, the promoter is capable of regulating expression of a sense, or ribozyme, or antisense, or co-suppression molecule or gene targeting, in a plant cell. Examples of preferred promoters include the CaMV 35S promoter, NOS promoter, octopine synthase (OCS) promoter and the like.

In a most preferred embodiment, the promoter is capable of expression in any plant cell, such as, but not limited to a plant selected from the list comprising *Arabidopsis thaliana, Oryza saliva,* wheat, barley, maize, Brassica ssp., *Gossypium hirsutum* and Eucalyptus ssp., hemp, jute, flax, and woody plants including, but not limited to Pinus ssp., Populus ssp., Picea spp., amongst others.

In a particularly preferred embodiment, the promoter may be derived from a genomic clone encoding a cellulose gene product, in particular the promoter contained in the sequence set forth in SEQ ID NO:3 or SEQ ID NO:4. Preferably, the promoter sequence comprises nucleotide 1 to about 1900 of SEQ ID NO:3 or nucleotides 1 to about 700 of SEQ ID NO:4 or a homologue, analogue or derivative capable of hybridizing thereto under at least low stringency conditions.

Optionally, the genetic construct of the present invention further comprises a terminator sequence.

In an exemplification of this embodiment, there is provided a binary genetic construct comprising the isolated nucleotide sequence of nucleotides set forth in SEQ ID NO:3. There is also provided a genetic construct comprising the isolated nucleotide sequence of nucleotides set forth in SEQ ID NO:1, in the antisense orientation, placed operably in connection with the CaMV 35S promoter.

In the present context, the term "in operable connection with" means that expression of the isolated nucleotide sequence is under the control of the promoter sequence with which it is connected, regardless of the relative physical distance of the sequences from each other or their relative orientation with respect to each other.

An alternative embodiment of the invention is directed to a genetic construct comprising a promoter or functional derivative, part, fragment, homologue, or analogue thereof, which is capable of directing the expression of a polypeptide early in the development of a plant cell at a stage when the cell wall is developing, such as during cell expansion or during cell division. In a particularly preferred embodiment, the promoter is contained in the sequence set forth in SEQ ID NO:3 or SEQ ID NO:4. Preferably, the promoter sequence comprises nucleotide 1 to about 1900 of SEQ ID NO:3 or nucleotides 1 to about 700 of SEQ ID NO:4 or a homologue, analogue or derivative capable of hybridizing thereto under at least low stringency conditions.

The polypeptide may be a reporter molecule which is encoded by a gene such as the bacterial β-glucuronidase gene or chloramphenicol acetyltransferase gene or alternatively, the firefly luciferase gene. Alternatively, the polypeptide may be encoded by a gene which is capable of producing a modified cellulose in the plant cell when placed in combination with the normal complement of cellulose genes which are expressible therein, for example it may be a cellulose-like gene obtained from a bacterial or fungal source or a cellulose gene obtained from a plant source.

The genetic constructs of the present invention are particularly useful in the production of crop plants with altered cellulose content or structure. In particular, the rate of cellulose deposition may be reduced leading to a reduction in the total cellulose content of plants by transferring one or more of the antisense, ribozyme or co-suppression molecules described supra into a plant or alternatively, the same or similar end-result may be achieved by replacing an endogenous cellulose gene with an inactive or modified cellulose gene using gene-targeting approaches. The benefits to be derived from reducing cellulose content in plants are especially apparent in food and fodder crops such as, but not limited to maize, wheat, barley, rye, rice, barley, millet or sorghum, amongst others where improved digestibility of said crop is desired. The foregoing antisense, ribozyme or co-suppression molecules are also useful in producing plants with altered carbon partitioning such that increased carbon is available for growth, rather than deposited in the form of cellulose.

Alternatively, the introduction to plants of additional copies of a cellulose gene in the 'sense' orientation and under the control of a strong promoter is useful for the production of plants with increased cellulose content or more rapid rates of cellulose biosynthesis. Accordingly, such plants may exhibit a range of desired traits including, but not limited to modified strength and/or shape and/or properties of fibres, cell and plants, increased protection against chemical, physical or environmental stresses such as dehydration, heavy metals (e.g. cadmium) cold, heat or wind, increased resistance to attack by pathogens such as insects, nematodes and the like which physically penetrate the cell wall barrier during invasion/infection of the plant.

Alternatively, the production of plants with altered physical properties is made possible by the introduction thereto of altered cellulose gene(s). Such plants may produce β-1,4-glucan which is either non-crystalline or shows altered crystallinity. Such plants may also exhibit a range of desired traits including but not limited to, altered dietary fibre content, altered digestibility and degradability or producing plants with altered extractability properties.

Furthermore, genetic constructs comprising a plant cellulose gene in the 'sense' orientation may be used to complement the existing range of cellulose genes present in a plant, thereby altering the composition or timing of deposition of cellulose deposited in the cell wall of said plant. In a preferred embodiment, the cellulose gene from one plant species or a β-1,4-glucan synthase gene from a non-plant species is used to transform a plant of a different species, thereby introducing novel cellulose biosynthetic metabolism to the second-mentioned plant species.

In a related embodiment, a recombinant fusion polypeptide may be produced containing the active site from one cellulose gene product fused to another cellulose gene product, wherein said fusion polypeptide exhibits novel catalytic properties compared to either 'parent' polypeptide from which it is derived. Such fusion polypeptides may be produced by conventional recombinant DNA techniques known to those skilled in the art, either by introducing a recombinant DNA capable of expressing the entire fusion polypeptide into said plant or alternatively, by a gene-targeting approach in which recombination at the DNA level occurs in vivo and the resultant gene is capable of expressing a recombinant fusion polypeptide.

The present invention extends to all transgenic methods and products described supra, including genetic constructs.

The recombinant DNA molecule carrying the sense, antisense, ribozyme or co-suppression molecule of the present invention and/or genetic construct comprising the same, may be introduced into plant tissue, thereby producing a "transgenic plant", by various techniques known to those skilled in the art. The technique used for a given plant species or specific type of plant tissue depends on the known successful techniques. Means for introducing recombinant DNA into plant tissue include, but are not limited to, transformation (Paszkowski et al., 1984), electroporation (Fromm et al., 1985), or microinjection of the DNA (Crossway et al., 1986), or T-DNA-mediated transfer from Agrobacterium to the plant tissue. Representative T-DNA vector systems are described in the following references: An et al.(1985); Herrera-Estrella et al. (1983a,b); Herrera-Estrella et al. (1985). Once introduced into the plant tissue, the expression of the introduced gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

A still further aspect of the present invention extends to a transgenic plant such as a crop plant, carrying the foregoing sense, antisense, ribozyme, co-suppression, or gene-targeting molecule and/or genetic constructs comprising the same. Preferably, the transgenic plant is one or more of the following: *Arabidopsis thaliana, Oryza sativa,* wheat, barley, maize, Brassica ssp., *Gossypium hirsutum* and Eucalyptus ssp., hemp, jute, flax, Pinus ssp., Populus ssp., or Picea spp. Additional species are not excluded.

The present invention further extends to the progeny of said transgenic plant.

Yet another aspect of the present invention provides for the expression of the subject genetic sequence in a suitable host (e.g. a prokaryote or eukaryote) to produce full length or non-full length recombinant cellulose gene products.

Hereinafter the term "cellulose gene product" shall be taken to refer to a recombinant product of a cellulose gene as hereinbefore defined. Accordingly, the term "cellulose gene product" includes a polypeptide product of any gene involved in the cellulose biosynthetic pathway in plants, such as, but not limited to a cellulose synthase gene product.

Preferably, the recombinant cellulose gene product comprises an amino acid sequence having the catalytic activity of a cellulose synthase polypeptide or a functional mutant, derivative part, fragment, or analogue thereof.

In a particularly preferred embodiment of the invention, the recombinant cellulose gene product comprises a sequence or amino acids that is at least 40% identical to any one or more of SEQ ID Nos:2, 6, 8, 10, 12 or 14, or a homologue, analogue or derivative thereof.

Single and three-letter abbreviations used for amino acid residues contained in the specification are provided in Table 1.

In the present context, "homologues" of an amino acid sequence refer to those polypeptides, enzymes or proteins which have a similar catalytic activity to the amino acid sequences described herein, notwithstanding any amino acid substitutions, additions or deletions thereto. A homologue may be isolated or derived from the same or another plant species as the species from which the polypeptides of the invention are derived.

"Analogues" encompass polypeptides of the invention notwithstanding the occurrence of any non-naturally occurring amino acid analogues therein.

"Derivatives" include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are particularly contemplated by the present invention. Additionally, derivatives of an amino acid sequence described herein which comprises fragments or parts of the subject amino acid sequences are within the scope of the invention, as are homopolymers or heteropolymers comprising two or more copies of the subject polypeptides. Procedures for derivatizing peptides are well-known in the art.

TABLE 1

| Amino Acid | Three-letter Abbreviation | One-letter Abbreviation |
|---|---|---|
| Alanine | Ala | A |
| Arginine | Arg | R |
| Asparagine | Asn | N |
| Aspartic acid | Asp | D |
| Cysteine | Cys | C |
| D-alanine | Dal | X |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tryosine | Tyr | Y |
| Valine | Val | V |
| Any amino acid | Xaa | X |

Substitutions encompass amino acid alterations in which an amino acid is replaced with a different naturally-occurring or a non-conventional amino acid residue. Such substitutions may be classified as "conservative", in which an amino acid residue contained in a cellulose gene product is replaced with another naturally-occurring amino acid of similar character, for example Gly←→Ala, Val←→Ile←→Leu, Asp←→Glu, Lys←→Arg, Asn←→Gln or Phe←→Trp←→Tyr.

Substitutions encompassed by the present invention may also be "non-conservative", in which an amino acid residue which is present in a cellulose gene product described herein is substituted with an amino acid with different properties, such as a naturally-occurring amino acid from a different group (eg. substituted a charged or hydrophobic amino acid with alanine), or alternatively, in which a naturally-occurring amino acid is substituted with a non-conventional amino acid.

Non-conventional amino acids encompassed by the invention include, but are not limited to those listed in Table 2.

Amino acid substitutions are typically of single residues, but may be of multiple residues, either clustered or dispersed.

Amino acid deletions will usually be of the order of about 1–10 amino acid residues, while insertions may be of any length. Deletions and insertions may be made to the N-terminus, the C-terminus or be internal deletions or insertions. Generally, insertions within the amino acid sequence will be smaller than amino- or carboxy-terminal fusions and of the order of 1–4 amino acid residues.

A homologue, analogue or derivative of a cellulose gene product as referred to herein may readily be made using peptide synthetic techniques well-known in the art, such as solid phase peptide synthesis and the like, or by recombinant DNA manipulations. Techniques for making substituent mutations at pre-determined sites using recombinant DNA technology, for example by M13 mutagenesis, are also well-known. The manipulation of nucleic acid molecules to produce variant peptides, polypeptides or proteins which manifest as substitutions, insertions or deletions are well-known in the art.

The cellulose gene products described herein may be derivatized further by the inclusion or attachment thereto of a protective group which prevents, inhibits or slows proteolytic or cellular degradative processes. Such derivatization may be useful where the half-life of the subject polypeptide is required to be extended, for ample to increase the amount of cellulose produced in a primary or secondary cell wall of a plant cell or alternatively, to increase the amount of protein produced in a bacterial or eukaryotic expression system. Examples of chemical groups suitable for this purpose include. but are not limited to, any of the non-conventional amino acid residues listed in Table 2, in particular a D-stereoisomer or a methylated form of a naturally-occurring amino acid listed in Table 1. Additional chemical groups which are useful for this purpose are selected from the list comprising aryl or heterocyclic N-acyl substituents, polyalkylene oxide moieties, desulphatohirudin muttons, alpha-muteins, alpha-aminophosphonic acids, water-soluble polymer groups such as polyethylene glycol attached to sugar residues using hydrazone or oxime groups, benzodiazepine dione derivatives, glycosyl groups such as beta-glycosylamine or a derivative thereof, isocyanate conjugated to a polyol functional group or polyoxyethylene polyol capped with diisocyanate, amongst others. Similarly, a cellulose gene product or a homologue, analogue or derivative thereof may be cross-linked or fused to itself or to a protease inhibitor peptide, to reduce susceptibility of said molecule to proteolysis.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarganine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methyfleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | [001b]Dnm-met |

TABLE 2-continued

| Non-conventional amino acid | Code | Non-conventional amino acid | Code |
|---|---|---|---|
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

In an alternative embodiment of the invention, the recombinant cellulose gene product is characterised by at least one functional β-glycosyl transferase domain contained therein.

The term "β-glycosyl transferase domain" as used herein refers to a sequence of amino acids which is highly conserved in different processive enzymes belonging to the class of glycosyl transferase enzymes (Saxena et al., 1995), for example the bacterial β-1,4-glycosyl transferase enzymes and plant cellulose synthase enzymes amongst others, wherein said domain possesses a putative function in contributing to or maintaining the overall catalytic activity, substrate specificity or substrate binding of an enzyme in said enzyme class. The β-glycosyl transferase domain is recognisable by the occurrence of certain amino acid residues at particular locations in a polypeptide sequence, however there is no stretch of contiguous amino acid residues comprised therein.

As a consequence of the lack of contiguity in a β-glycosyl transferase domain, it is not a straightforward matter to isolate a cellulose gene by taking advantage of the presence of a β-glycosyl transferase domain in the polypeptide encoded by said gene. For example, the β-glycosyl transferase domain would not be easily utilisable as a probe to facilitate the rapid isolation of all β-glycosyl transferase genetic sequences from a particular organism and then to isolate from those genetic sequences a cellulose gene such as cellulose synthase.

In a preferred embodiment, the present invention provides an isolated polypeptide which:
(i) contains at least one structural β-glycosyl transferase domain as hereinbefore defined; and
(ii) has at least 40% amino acid sequence similarity to at least 20 contiguous amino acid residues set forth in any one or more of SEQ ID Nos:2, 6, 8, 10, 12 or 14, or a homologue, analogue or derivative thereof.

More preferably, the polypeptide of the invention is at least 40% identical to at least 50 contiguous amino acid residues, even more preferably at least 100 amino acid residues of any one or more of SEQ ID Nos:2, 6, 8, 10, 12 or 14, or a homologue, analogue or derivative thereof.

In a particularly preferred embodiment, the percentage similarity to any one or more of SEQ ID Nos:2, 6, 8, 10, 12 or 14 is at least 50–60%. more preferably at least 65–70%, even more preferably at least 75–80% and even more preferably at least 85–90%, including about 91% or 95%.

In a related embodiment, the present invention provides a "sequencably pure" form of the amino acid sequence described herein. "Sequencably pure" is hereinbefore described as substantially homogeneous to facilitate amino acid determination.

In a further related embodiment, the present invention provides a "substantially homogeneous" form of the subject amino acid sequence, wherein the term "substantially homogeneous" is hereinbefore defined as being in a form suitable for interaction with an immunologically interactive molecule. Preferably, the polypeptide is at least 20% homogeneous, more preferably at least 50% homogeneous, still more preferably at least 75% homogeneous and yet still more preferably at least about 95–100% homogenous, in terms of activity per microgram of total protein in the protein preparation.

The present invention further extends to a synthetic peptide of at least 5 amino acid residues in length derived from or comprising a part of the amino acid sequence set forth in any one or more of SEQ ID Nos:2, 6, 8, 10, 12 or 14, or having at least 40% similarity thereto.

Those skilled in the art will be aware that such synthetic peptides may be useful in the production of immunologically interactive molecules for the preparation of antibodies or as the peptide component of an immunoassay.

The invention further extends to an antibody molecule such as a polyclonal or monoclonal antibody or an immunologically interactive part or fragment thereof which is capable of binding to a cellulose gene product according to any of the foregoing embodiments.

The term "antibody" as used herein, is intended to include fragments thereof which are also specifically reactive with a polypeptide of the invention. Antibodies can be fragmented using conventional techniques and the fragments screened for utility in the same manner as for whole antibodies. For example, F(ab')2 fragments can be generated by treating antibody with pepsin. The resulting F(ab')2 fragment can be treated to reduce disulfide bridges to produce Fab' fragments.

Those skilled in the art will be aware of how to produce antibody molecules when provided with the cellulose gene product of the present invention. For example, by using a polypeptide of the present invention polyclonal antisera or monoclonal antibodies can be made using standard methods. A mammal, (e.g., a mouse, hamster, or rabbit) can be immunized with an immunogenic form of the polypeptide which elicits an antibody response in the mammal. Techniques for conferring immunogenicity on a polypeptide include conjugation to carriers or other techniques well known in the art. For example, the polypeptide can be administered in the presence of adjuvant. The progress of immunization can be monitored by detection of antibody titers in plasma or serum. Standard ELISA or other immunoassay can be used with the immunogen as antigen to assess the levels of antibodies. Following immunization, antisera can be obtained and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (1975) as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse el al., 1989). Hybridoma cells can be screened immunochemically for production of antibodies which are specifically reactive with the polypeptide and monoclonal antibodies isolated.

As with all immunogenic compositions for eliciting antibodies, the immunogenically effective amounts of the polypeptides of the invention must be determined empirically. Factors to be considered include the immunogenicity of the native polypeptide, whether or not the polypeptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

It is within the scope of this invention to include any second antibodies (monoclonal, polyclonal or fragments of antibodies) directed to the first mentioned antibodies discussed above. Both the first and second antibodies may be used in detection assays as a first antibody may be used with a commercially available anti-immunoglobulin antibody.

The present invention is further described by reference to the following non-limiting Figures and Examples.

In the Figures:

FIG. 1 is a photographic representation showing the inflorescence length of wild-type *Arabidopsis thaliana* Columbia plants (plants 1 and 3) and rsw1 plants (plants 2 and 4) grown at 21° C. (plants 1 and 2) or 31° C. Plants were grown initially at 21° C. until bolting commenced, the bolts were removed and the re-growth followed in plants grown at each temperature.

Figure 4:
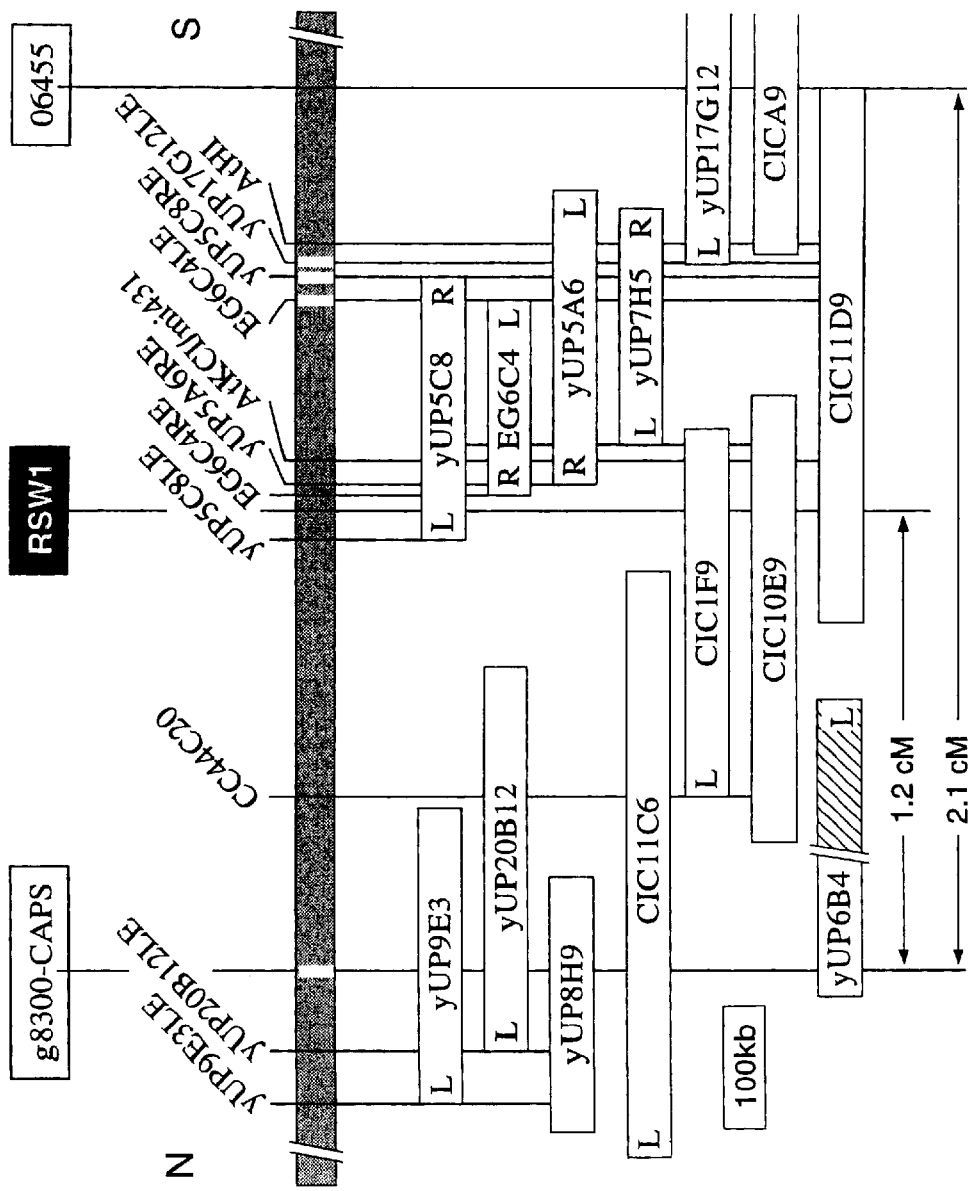

FIG. 4 is a schematic representation of the contiguous region of *Arabidopsis thaliana* chromosome 4 (stippled box) between the cosmid markers g8300 and 06455, showing the location of overlapping YAC clones (open boxes) within the contiguous region. The position of the RSW1 locus is also indicated, approximately 1.2 cM from g8300 and 0.9 cM from 06455. The scale indicates 100 kb in length. L, left-end of YAC; R, right-end of YAC. Above the representation of chromosome 4, the YAC fragments and cosmid clone fragments used to construct the contiguous region are indicated, using a prefix designation corresponding to the YAC or cosmid from which the fragments were obtained (eg yUP9E3, yUP20B12, etc) and a suffix designation indicating whether the fragment corresponds to the right-end (RE) or left-end (LE) of the YAC clone; N, North; S, South; CAPS, cleaved amplified polymorphic sequence (Konieczny and Ausubel, 1993) version of the g8300 marker.

Figure 5:
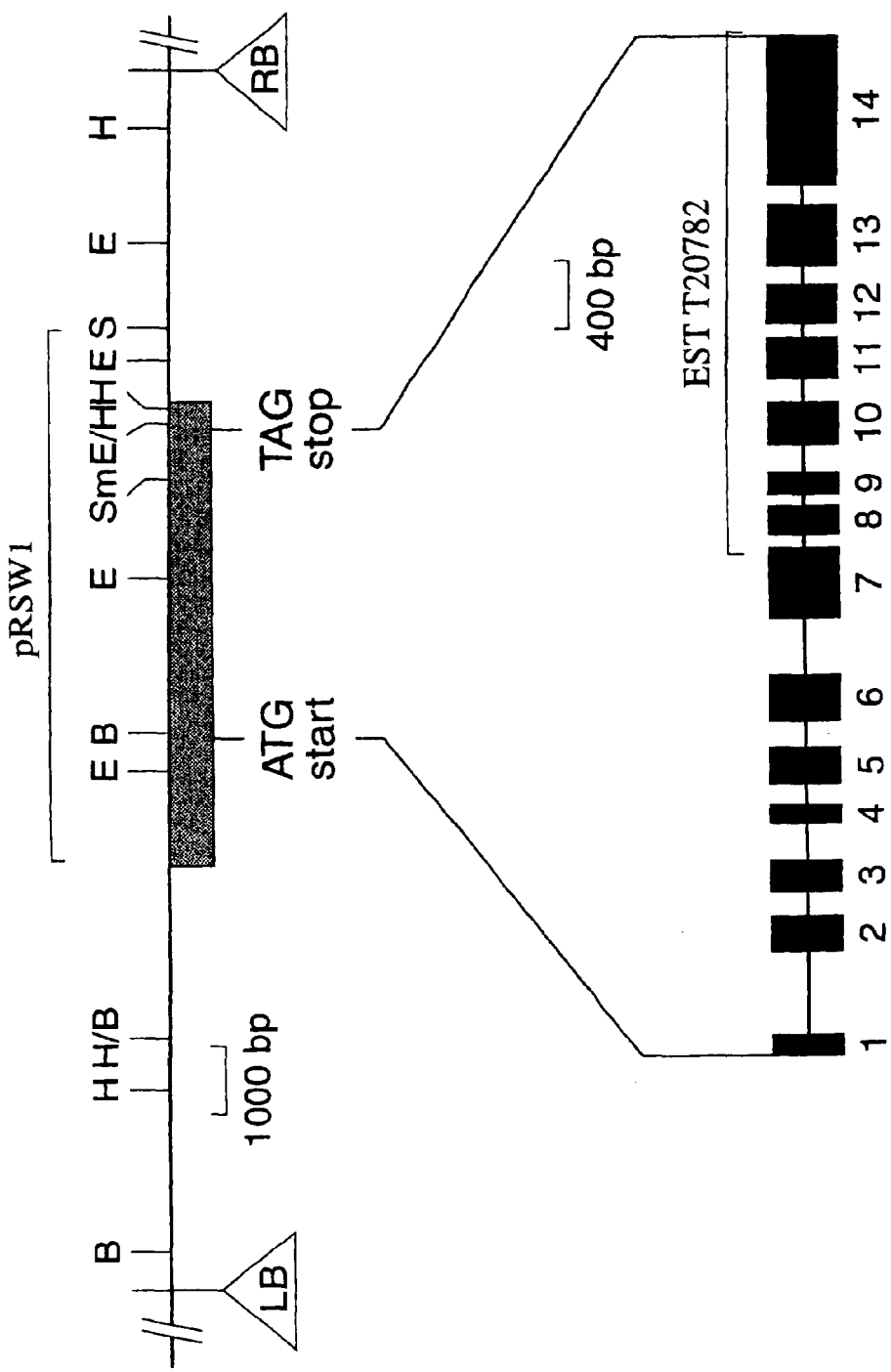

FIG. 5 is a schematic representation of a restriction map of construct 23H12 between the left T-DNA border (LB) and right T-DNA border (RB) sequences (top solid line), showing the position of the *Arabidopsis thaliana* RSW1 locus (stippled box). The line at the top of the figure indicates the region of 23H12 which is contained in construct pRSW1. The structure of the RSW1 gene between the translation start (ATG) and translation stop (TAG) codons is indicated at the bottom of the figure. Exons are indicated by filled boxes; introns are indicated by the solid black line. The alignment of EST clone T20782 to the 3'-end of the RSW1 gene, from near the end of exon 7 to the end of exon 14, is also indicated at the bottom of the figure. Restriction sites within 23H12 are as follows: B, BamHI; E, EcoRI; H, HindIII; S, SalI; Sm, SmaI.

Figure 6:
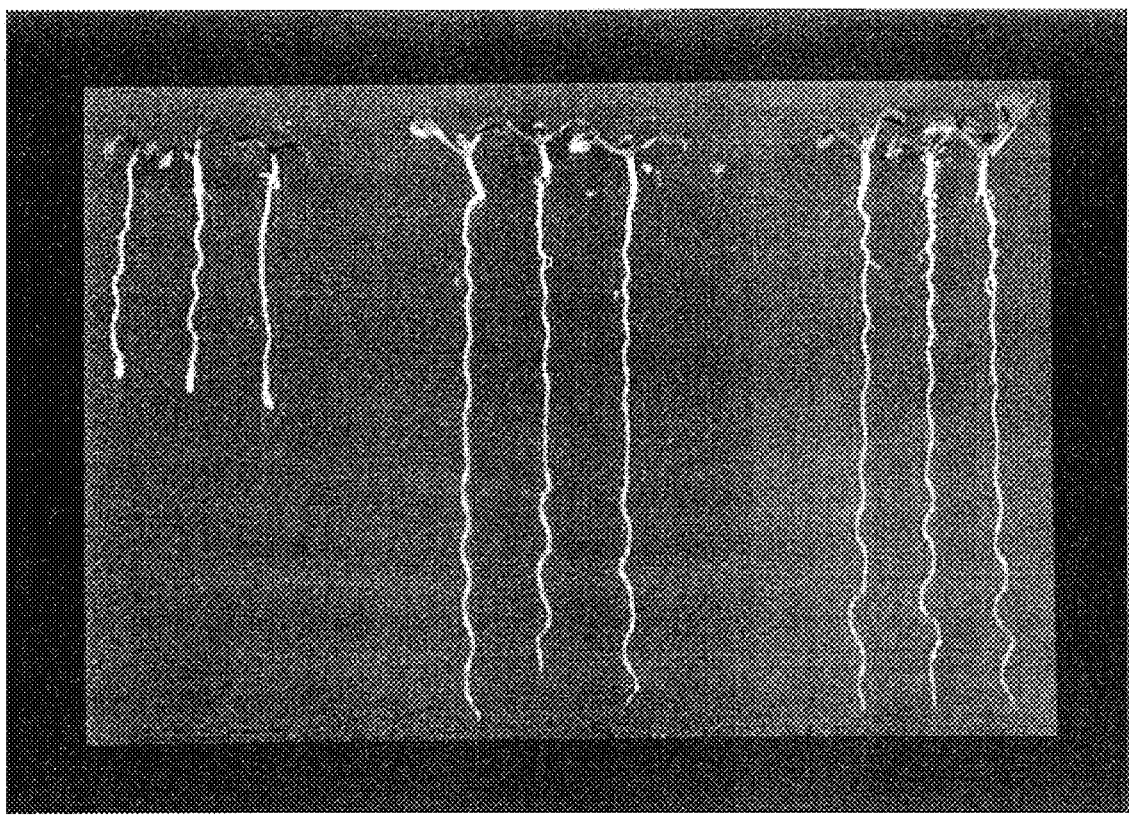

FIG. 6 is a photographic representation showing complementation of the radial root swelling phenotype of the rsw1 mutant by transformation with construct 23H12. The rsw1 mutant was transformed with 23H12 as described in Example 6. Transformed rsw1 plants (centre group of three seedlings), untransformed rsw1 plants (left group of three seedlings) and untransformed *A.thaliana* Columbia plants (right group of three seedlings) were grown at 21° C. for 5 days and then transferred to 31° C. for a further 2 days, after which time the degree of root elongation and radial root swelling was determined.

Figure 7:
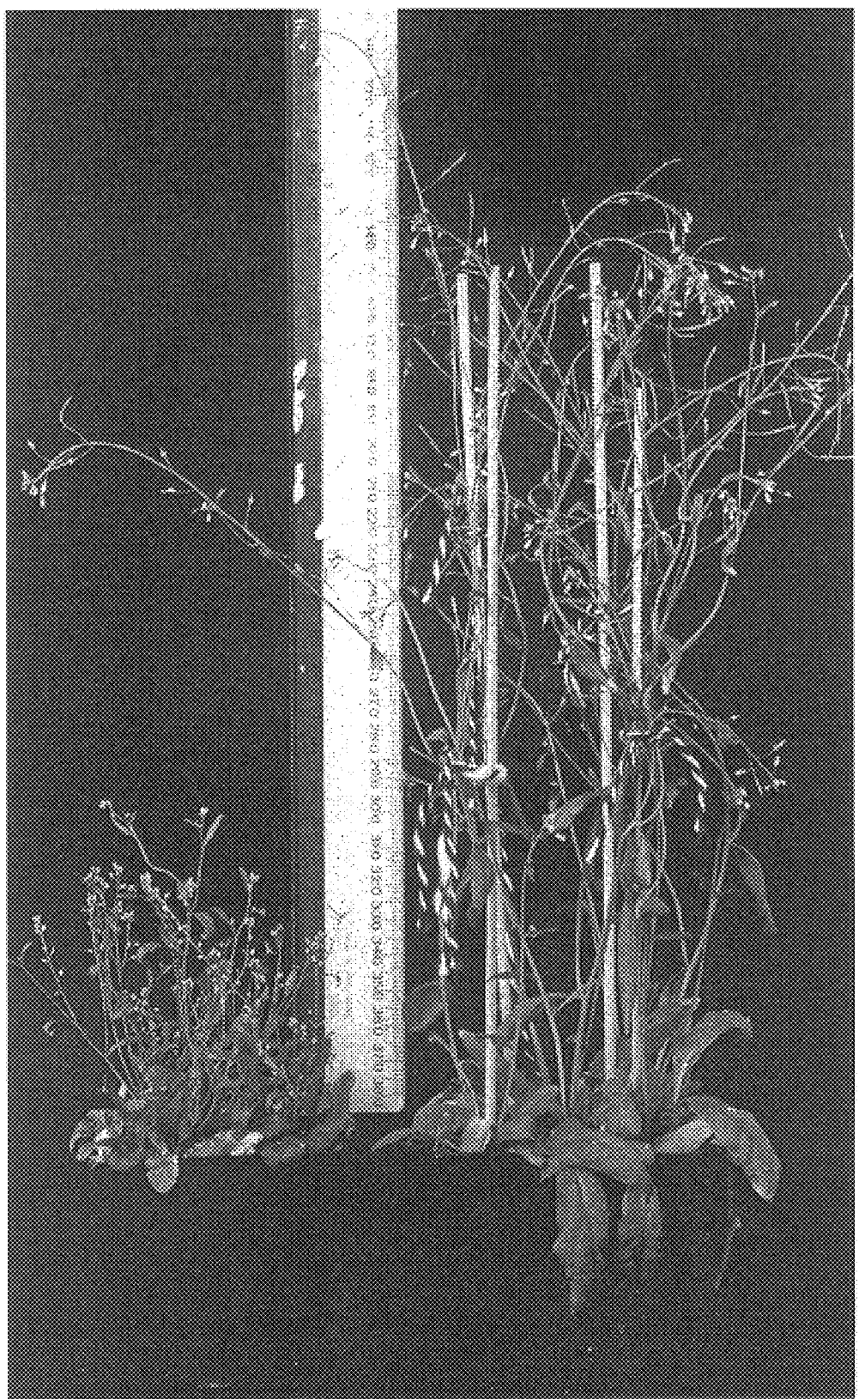

FIG. 7 is a photographic representation comparing wild-type *Arabidopsis thaliana* Columbia plants (right-hand side of the ruler) and *A.thaliana* Columbia plants transformed with the antisense RSW1 construct (i.e. EST T20782 expressed in the antisense orientation under control of the CaMV 35S promoter sequence; left-hand side of the ruler), showing inflorescence shortening at 21° C. in plants transformed with the antisense RSW1 construct compared to untransformed Columbia plants. The phenotype of the antisense plants at 21° C. is similar to the phenotype of the rsw1 mutant at 31° C. Inflorescence height is indicated in millimeters.

Figure 8:
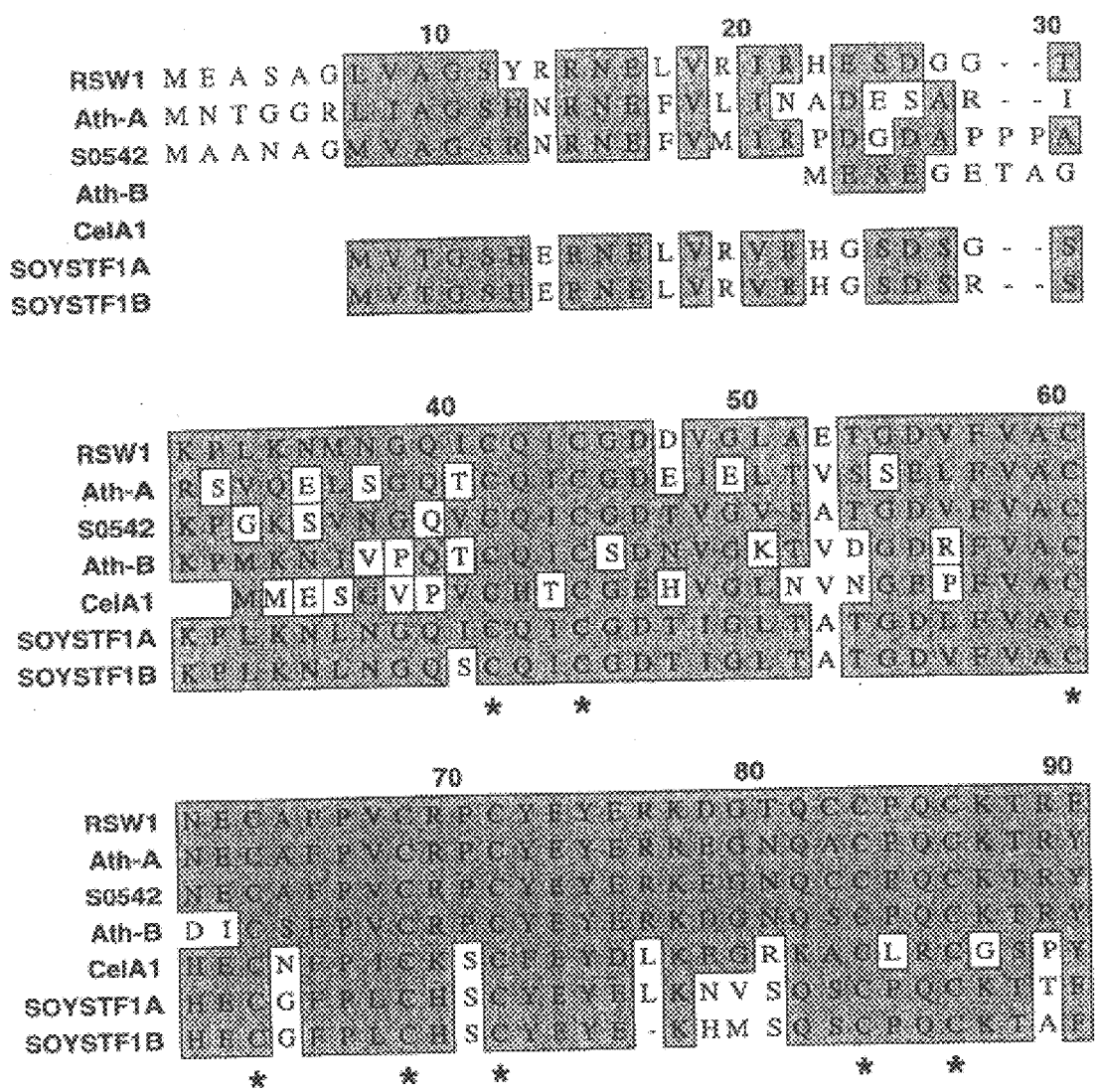

FIG. 8 is a schematic representation showing the first 90 amino acid residues of *Arabidopsis thaliana* RSW1 aligned to the amino acid sequences of homologous polypeptides from *A. thaliana* and other plant species. The shaded region indicates highly conserved sequences. Ath-A and Ath-B are closely related *Arabidopsis thaliana* cDNA clones identified by hybridisation screening using part of the RSW1 cDNA as a probe. S0542, rice EST clone (MAFF DNA bank, Japan); celA1 and celA2, cotton cDNA sequences expressed in cotton fibre (Pear et al, 1996); SOYSTF1A and SOYSTF1B, putative soybean bZIP transcription factors. Amino acid designations are as indicated in Table 1 incorporated herein. Conserved cysteine residues are indicated by the asterisk.

FIGS. (9A–9J) is a schematic representation showing the alignment of the complete amino acid sequence of *Arabidopsis thaliana* RSW1 to the amino acid sequences of homologous polypeptides from *A. thaliana* and other plant species. The shaded region indicates highly conserved sequences. Ath-A and Ath-B are closely related *Arabidopsis thaliana* cDNA clones identified by hybridisation screening using part of the RSW1 cDNA as a probe. S0542, rice EST clone (MAFF DNA bank, Japan); celA1, cotton genetic sequence (Pear et al, 1996); D48636, a partial cDNA clone obtained from rice (Pear et al, 1996). Amino acid designations are as indicated in Table 1 incorporated herein. Numbering indicates the amino acid position in the RSW1 sequence.

Figure 10:
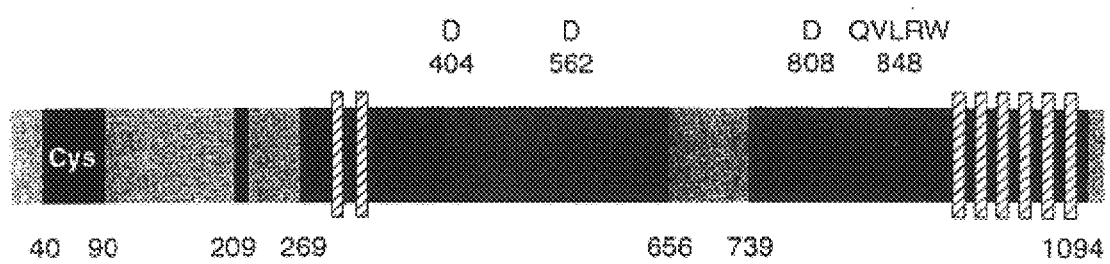

FIG. 10 is a schematic representation of the RSW1 polypeptide, showing the positions of putative transmembrane helices (hatched boxes), cysteine-rich region (Cys) and aspartate residues (D) and the QVLRW signature which are conserved between RSW1 and related amino acid sequences. Regions of RSW1 which are highly-conserved between putative cellulose biosynthesis polypeptides are indicated by the dark-shaded boxes, while less-conserved regions are indicated by the light-shaded boxes.

Figure 11:
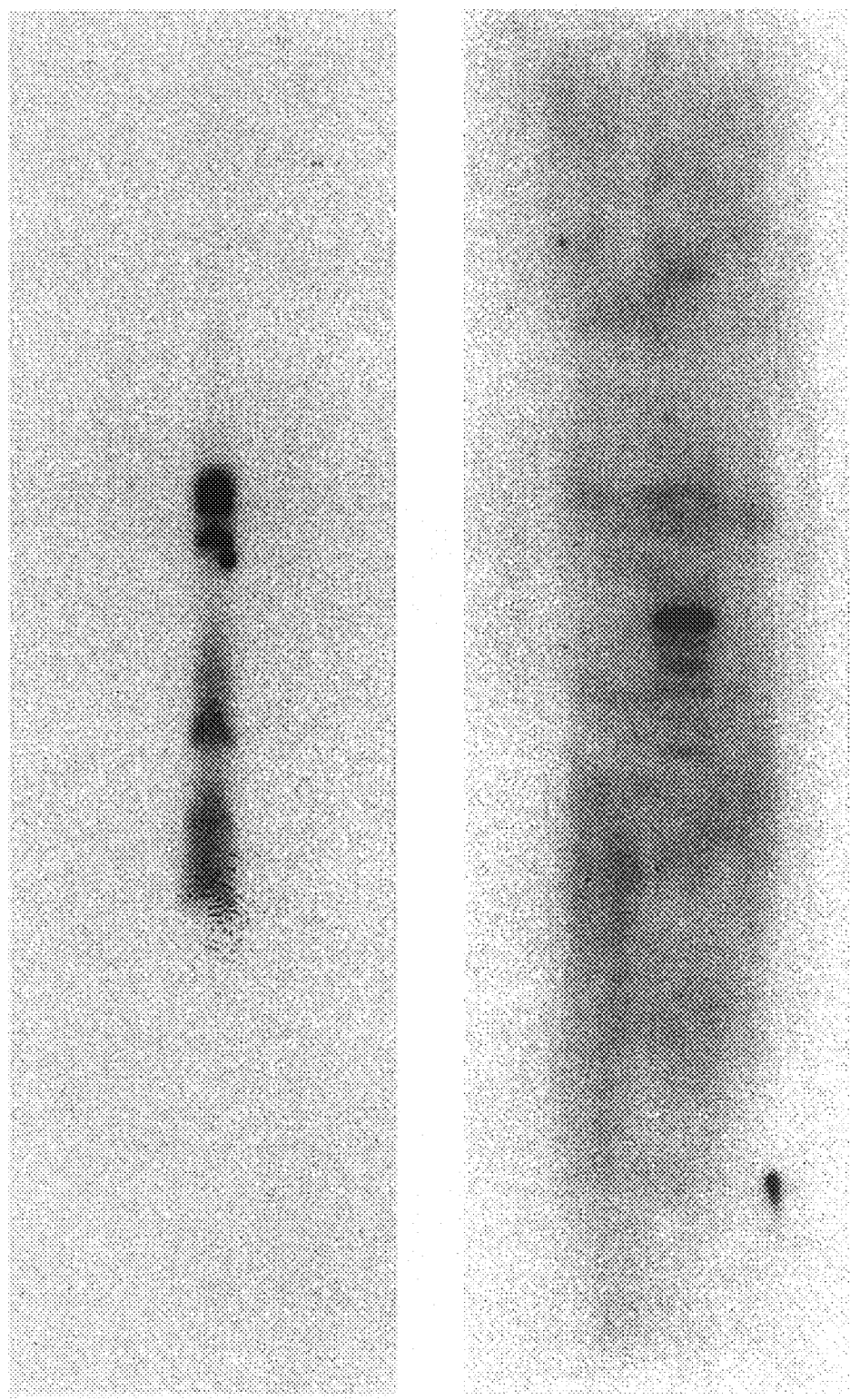

FIG. 11 is a photographic representation of a Southern blot hybridisation of the 5'-end of the *Arabidopsis thaliana* RSW1 cDNA to BglII-digested DNA derived from *A. thaliana* (lane 1) and cotton (lane 2). Hybridisations were carried out under low stringency conditions at 55° C. Arrows indicate the positions of hybridising bands.

EXAMPLE 1

Characterisation of the Cellulose-Deficient *Arabidopsis thaliana* Mutant rsw1

1. Morphology

The *Arabidopsis thaliana* rsw1 mutant was produced in a genetic background comprising the ecotype Columbia.

The altered root cell-shape and temperature sensitivity of the root morphology of the *Arabidopsis thaliana* mutant rsw1 are disclosed, among other morphological mutants, by Baskin et al. (1992).

Figure 1:
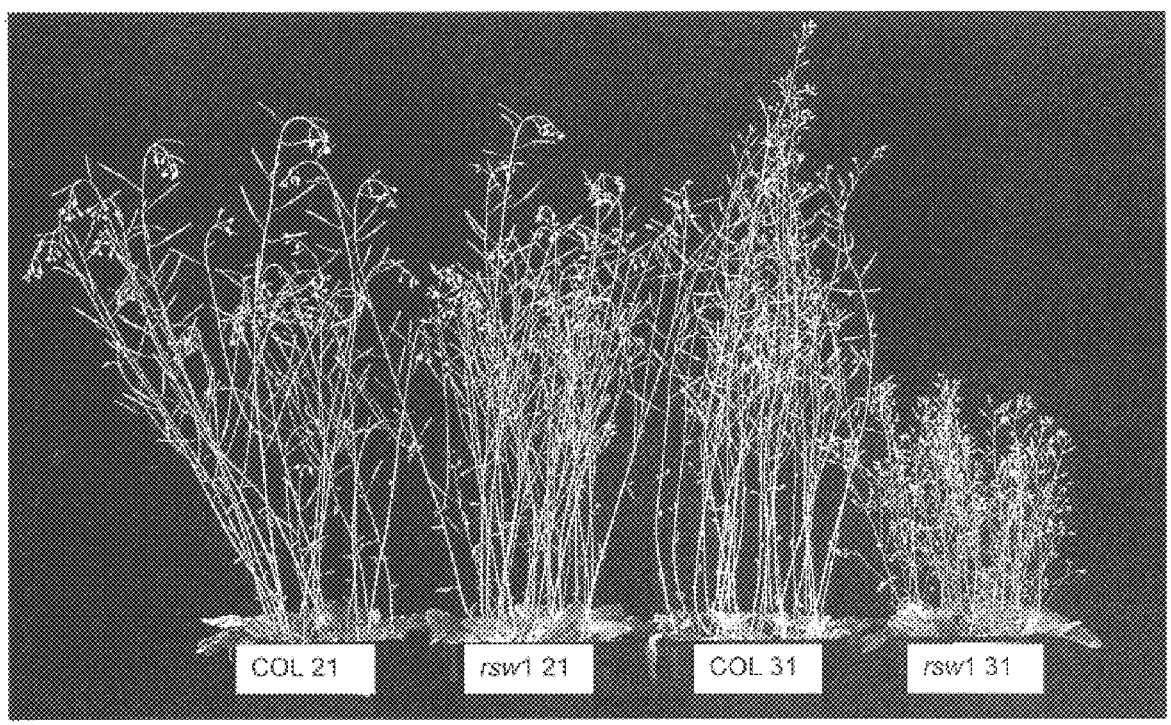

As shown in FIG. 1, the present inventors have shown that the rsw1 mutant exhibits the surprising phenotype of having reduced inflorescence height when grown at 31° C., compared to wild-type Columbia plants grown under similar conditions. In contrast, when grown at 21° C., the inflorescence height of rsw1 is not significantly different from wild type plants grown under similar conditions, indicating that the shoot phenotype of rsw1 is conditional and temperature-dependent.

Figure 2:
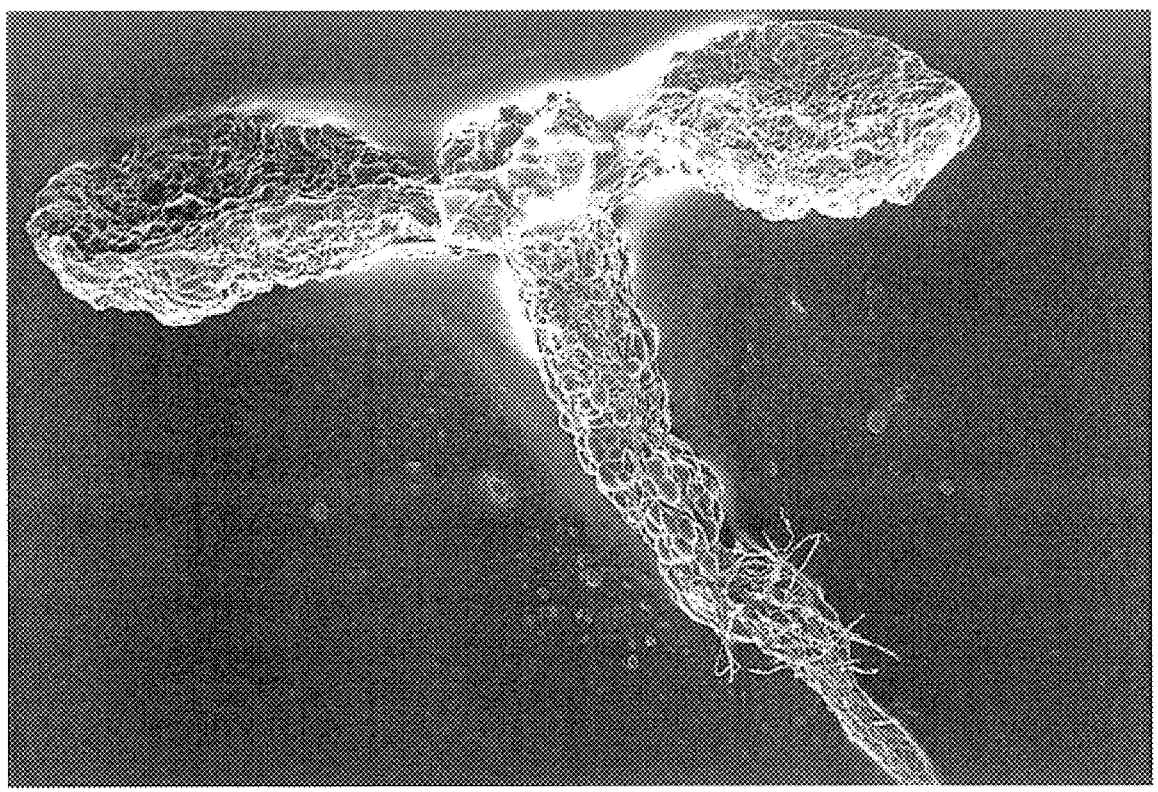
FIG. 2 is a photographic representation of a cryo-scanning electron micrograph showing misshapen epidermal cells in the cotyledons and hypocotyl of the rsw1 mutant when grown at 31° C. for 10 days.

Furthermore, cryo-scanning electron microscopy of the epidermal cells of the rsw1 mutant indicates significant abnormality in cell shape, particularly in respect of those epidermal cells forming the leaves, hypocotyl and cotyledons, when the seedlings are grown at 31° C. (FIG. 2).

Rosettes (terminal complexes) are the putative hexameric cellulose synthase complexes of higher plant plasma membranes (Herth, 1985). Freeze-fractured root cells of *Arabidopsis thaliana* rsw1 plants grown at 18° C. show cellulose microfibrils and rosettes on the PF face of the plasma membrane that resembles those of wild-type *A. thaliana* and other angiosperms. Transferring the rsw1 mutant to 31° C. reduces the number of rosettes in the mutant within 30 min, leading to extensive loss after 3 hours. Plasma membrane particles align in rows on prolonged exposure to the restrictive temperature. In contrast, there is no change in the appearance of cortical microtubules that align cellulose microfibrils, or of Golgi bodies that synthesise other wall polysaccharides and assemble rosettes.

2. Carbohydrate Content

The effect of mutations in the RSW1 gene on the synthesis of cellulose and other carbohydrates was assessed by measuring in vivo incorporation of $^{14}C$ (supplied as uniformly labelled glucose) into various cell wall fractions. Wild type (RSW1) and homozygous mutant rsw1 seed were germinated at 21° C. on agar containing Hoagland's nutrients and 1% (w/v) unlabelled glucose. After 5 d, half of the seedlings were transferred to 31° C. for 1 d while the remainder were maintained at 21° C. for the same time. Seedlings were covered with a solution containing Hoagland's nutrients and $^{14}C$-glucose and incubated for a further 3 h at the same temperature. Rinsed roots and shoots were separated and frozen in liquid nitrogen. Tissue was homogenised in cold, 0.5 M potassium phosphate buffer (0.5M $KH_2PO_4$, pH7.0) and a crude cell wall fraction collected by centrifugation at 2800 rpm. The wall fraction was extracted with chloroform/methanol [1:1 (v/v)] at 40° C. for 1 hour, followed by a brief incubation at 150° C., to remove lipids. The pellet was washed successively with 2 ml methanol, 2 ml acetone and twice with 2 ml of deionised water. Finally. the pellet was extracted successively with dimethyl sulphoxide under nitrogen to remove starch; 0.5% ammonium oxalate to remove pectins; 0.1 M KOH and 3 mg/ml $NaBH_4$ and then with 4 M KOH and 3 mg/ml $NaBH_4$ to extract hemicelluloses; boiling acetic acid/nitric acid/water [8:1:2 (v/v)], to extract any residual non-cellulosic carbohydrates and leave crystalline cellulose as the final insoluble pellet (Updegraph, 1969). All fractions were analysed by liquid scintillation counting and the counts in each fraction from the mutant were expressed as a percentage of the counts in the wild type under the same conditions.

As shown in Table 3, mutant and wild type plants behave in quite similar fashion at 21° C. (the permissive temperature) whereas, at the restrictive temperature of 31° C., the incorporation of $^{14}C$ into cellulose is severely inhibited (to 36% of wild type) by the rsw1 mutation. The data in Table 3 indicate that cellulose synthesis is specifically inhibited in the rsw1 mutant. The wild type RSW1 gene is therefore involved quite directly in cellulose synthesis and changing its sequence by mutation changes the rate of synthesis.

TABLE 3

Counts in fractions from rsw1 plants expressed as a % of counts in comparable fraction from wild type plants

| Pectins | | Hemicelluloses | | Cellulose | |
|---------|---------|----------------|---------|-----------|---------|
| 21° C. | 31° C. | 21° C. | 31° C. | 21° C. | 31° C. |
| 125 | 104 | 111 | 101 | 80 | 36 |

In homozygous mutant rsw1 plants. the pectin fraction extracted by ammonium oxalate contained abundant glucose, atypical of true uronic acid-rich pectins. The great majority of the glucose remained in the supernatant when cetyltrimethylammonium bromide precipitated the negatively charged pectins.

3. Non-crystalline β-1,4-glucan Content

The quantity of cellulose and the quantity of a non-crystalline β-1,4-glucan recovered from the ammonium oxalate fraction were determined for seedlings of wild type Columbia and for backcrossed, homozygous rsw1 that were grown for either 7 days at 21° C. or alternatively, for 2 days at 21° C. and 5 days at 31° C., on vertical agar plates containing growth medium (Baskin et al., 1992) plus 1% (w/v) glucose, and under continuous light (90 $\mu$mol m$^{-2}$ s$^{-1}$). Roots and shoots were separated from about 150 seedlings, freeze-dried to constant weight and ground in a mortar and pestle with 3 ml of cold 0.5 M potassium phosphate buffer (pH 7.0). The combined homogenate after two buffer rinses (2 ml each) was centrifuged at 2800×g for 10 min. After washing the pellet fraction twice with 2 ml buffer and twice with 2 ml distilled water, the pellet, comprising the crude cell wall fraction, and the pooled supernatants, comprising the phosphate buffer fraction were retained. The crude cell wall pellet fraction was stirred with two 3 ml aliquots of chloroform/methanol [1:1 (v/v)] for 1 hour at 40° C., 2 ml of methanol at 40° C. for 30 min, 2 ml of acetone for 30 min, and twice with water. The whole procedure repeated in the case of shoots. Combined supernatants were dried in a nitrogen stream. The pellet was successively extracted with: (i) 3 ml of DMSO-water 9:1 [v/v], sealed under nitrogen, overnight with shaking, followed by two 2 ml extractions using DMSO/water and three 2 ml water washes; (ii) 3 ml of ammonium oxalate (0.5%) at 100° C. for 1 hour, followed by two water washes; (iii) 3 ml of 0.1 M KOH containing 1 mg/ml sodium borohydride, for 1 hour at 25° C. (repeated once for root material or twice for shoot material), with a final wash with 2 ml water; (iv) 3 ml of 4 M KOH containing 1 mg/ml sodium borohydride, for 1 hour at 25° C. (repeated once for root material or twice for shoot material). The final pellet was boiled with intermittent stirring in 3 ml of acetic acid-nitric acid-water [8:1:2 (v/v)] (Updegraph 1969), combined with 2 water washes. and diluted with 5 ml water.

The insoluble residue of cellulose was solubilised in 67% (v/v) $H_2SO_4$, shown to contain greater than 97% (w/v) glucose using GC/MS (Fisons AS800/MD800) of alditol acetates (Doares et al., 1991) and quantified in three independent samples by anthrone/$H_2SO_4$ reaction. Results of GC/MS for pooled replica samples are presented in Table 4.

The non-crystalline β-1,4-glucan was recovered as the supernatant from the ammonium oxalate fraction when anionic pectins were precipitated by overnight incubation at 37° C. with 2% (w/v) cetyltrimethylammonium bromide (CTAB) and collected by centrifugation at 2800×g for 10 min. The glucan (250 $\mu$g/ml) or starch (Sigma; 200 $\mu$g/ml) were digested with mixtures of endocellulase (EC 3.2.1.4; Megazyme, Australia) from Trichoderma and almond β-glucosidase (EC 3.2.1.21; Sigma), or Bacillus sp. α-amylase (EC 3.2.1.1; Sigma) and rice α-glucosidase (EC 3.2.1.20; Sigma).

Figure 3:
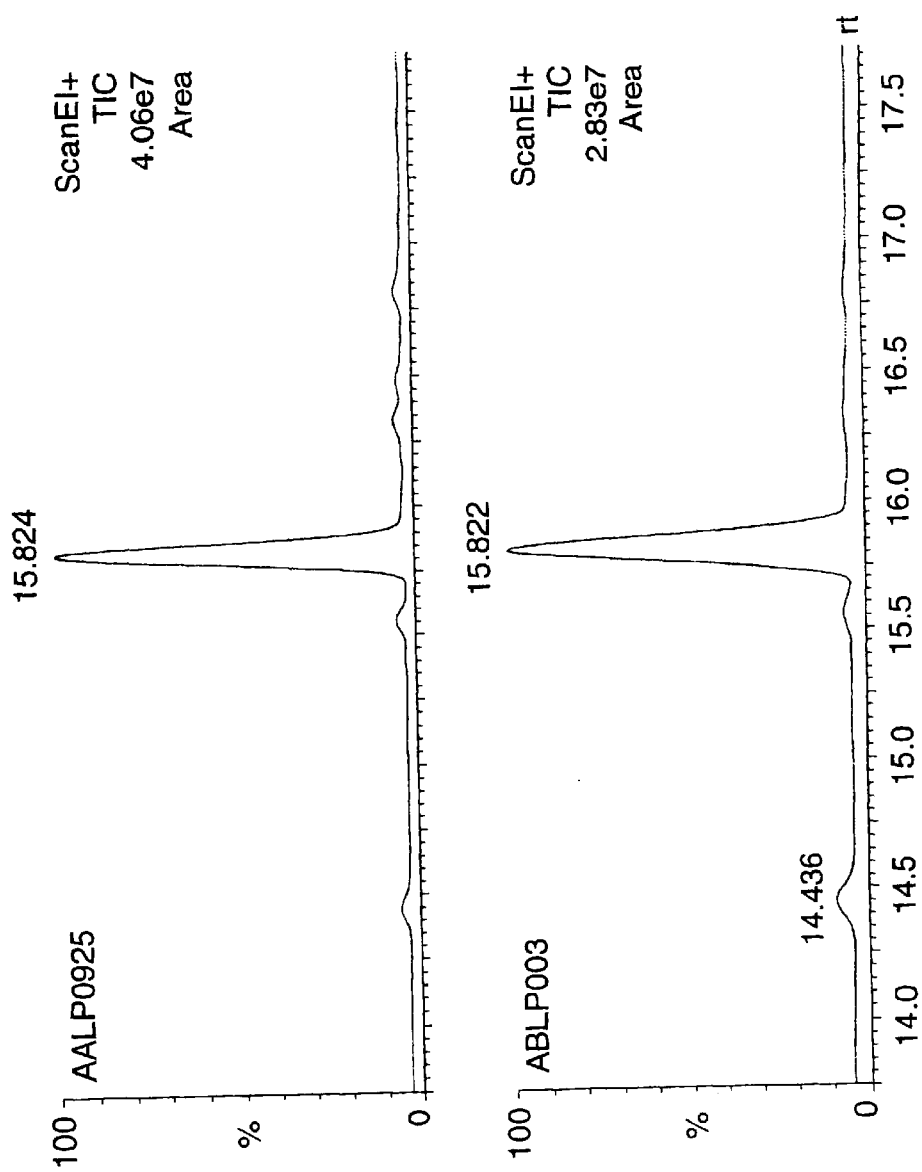
FIG. 3 is a graphical representation of a gas chromatograph of alditol acetates of methylated sugars from a cellulose standard (top panel) and from the neutral glucan derived from shoots of rsw1 plants grown at 31° C. (lower panel). The co-incident peaks show that the rsw1 glucan is 1,4-linked.

The material recovered in the supernatant from the ammonium oxalate fraction was shown to contain a pure β-1,4-glucan by demonstrating that: (i) only glucose was detectable when it was hydrolysed by 2 M TFA in a sealed tube for 1 h at 120° C. in an autoclave, the supernatant (2000 g for 5 min) was dried under vacuum at 45° C. to remove TFA and glucose was determined by GC/MS; (ii) methylation (Needs and Selvendran 1993) gave a dominant peak resolved by thin layer chromatography and by GC/MS that was identical to that from a cellulose standard and so indicative of 1,4-linked glucan (FIG. 3); and (iii) the endo-cellulase and β-1,4-glucosidase mixture released 83% of the TFA-releasable glucose from the glucan produced by rsw1 at 31° C. while the α-amylase/α-glucosidase mixture released no glucose from the glucan. Conversely, the α-amylase/α-glucosidase mixture released 95% of the TFA-releasable glucose from a starch sample, while the endo-cellulase/β-1,4-glucosidase mixture released no glucose from starch.

Extractability of the glucan using ammonium oxalate, and the susceptibility of the glucan to endocellulase/β-glucosidase and TFA hydrolysis indicate that the glucan in the rsw1 mutant is not crystalline, because it is the crystallinity of glucan which makes cellulose resistant to extraction and degradation.

Table 4 shows the quantity of glucose in cellulose determined by the anthrone/$H_2SO_4$ reaction and the quantity in the non-crystalline glucan after TFA hydrolysis, for shoots of wild type and mutant rsw1 Arabidopsis plants. The data indicate that the production of cellulose and of the non-crystalline β-1,4-glucan can be manipulated by mutational changes in the RSW1 gene.

TABLE 4

Glucose: contents of cellulose and of the ammonium oxalate-extractable glucan

| | wild type | | rsw1 | |
|---|---|---|---|---|
| | 21° C. | 31° C. | 21° C. | 31° C. |
| Cellulose | 273 + 28 | 363 + 18* | 218 + 20 | 159 + 19* |
| Glucan | 22 | 58 | 24 | 195 |

All values nmol glucose mg-1 plant dry weight + sd (n = 3).
*Differences significant at 0.001% level.

4. Starch Content

The quantity of starch recovered in the DMSO fraction from roots in the experiment described above was also determined by the anthrone/$H_2SO_4$ extraction (Table 5).

As shown in Table 5. the level of starch deposited in the rsw1 mutant is 4-fold that detectable in the roots of wild-type plants at the restrictive temperature of 31° C. A similar rise in starch is also seen if the data are expressed as nmol glucose per plant. There is no detectable difference in deposition at starch between rsw1 plants and wild-type plants at 21° C.

TABLE 5

Quantity of starch (nmol glucose per mg dry weight of seedling) extracted from roots of rsw1 and wild type seedlings

| | Phenotype | |
|---|---|---|
| Temperature | Wild-type | rsw1 mutant |
| 21° C. | 22 | 18 |
| 31° C. | 37 | 126 |

The composition of cell walls in the rsw1 mutant plant compared to wild type plants at the restrictive temperature of 31° C., is summarised in Table 6.

TABLE 6

Mol % composition of cell walls from shoots of rsw1 and wild-type seedlings grown at 31° C.

| | Phenotype | |
|---|---|---|
| Cell wall component | Wild-type | rsw1 mutant |
| Crystalline cellulose | 38.4 | 16.5 |
| Non-crystalline β-1,4-glucan | 8.5 | 27.1 |
| Pectin | 37.1 | 36.3 |
| Alkali-soluble | 15.6 | 19.8 |
| Acid-soluble | 0.3 | 0.4 |

In conclusion, the rsw1 mutation disassembles cellulose synthase complexes in the plasma membrane. reduces cellulose accumulation and causes β-1,4-glucan to accumulate in a non-crystalline form.

EXAMPLE 2

Mapping of YAC Clones to the rsw1 Locus

The rsw1 locus in the mutant *Arabidopsis thaliana* plant described in Example 1 above was mapped to chromosome 4 of *A. thaliana* using RFLP gene mapping techniques (Chang et al, 1988, Nam et al., 1989) to analyse the $F_2$ or $F_3$ progeny derived from a Columbia (Co)/Landsberg (Ler) cross. In particular, the rsw1 mutation was shown to be linked genetically to the ga5 locus, which is a chromosome 4 visual marker in *A. thaliana*.

Based on an analysis of map distances and chromosomal break points in 293 $F_2$ or $F_3$ progeny derived from a Columbia (Co)/Landsberg (Ler) cross, rsw1 was localised to an approximately 2.1 cM region between the RFLP markers g8300 and 06455, approximately 1.2 cM south of the CAPS (cleaved amplified polymorphic sequence; Konieczny and Ausubel, 1993) version of the g8300 marker (FIG. 4).

The interval between g8300 and 06455 in which rsw1 residues was found to be spanned by an overlapping set of Yeast Artificial Chromosome (YAC) clones. The clones were obtained from Plant Industry, Commonwealth Scientific and Industrial Research Organisation, Canberra, Australia. The YACs were positioned in the g8300/06455 interval by hybridisation using known DNA molecular markers (from within the interval) and DNA fragments from the ends of the YACs. The length of the interval was estimated to comprise 900 kb of DNA.

Refined gene mapping of recombinants within the region spanned by YAC clones established the genetic distance between the RFLP marker g8300 and the rsw1 locus.

The combination of genetic map distance data and the mapping of YAC clones within the region further localised the rsw1 locus to the YAC clone designated yUP5C8.

EXAMPLE 3

Mapping of cDNA Clones to the YAC Clone YUP5C8

An *Arabidopsis thaliana* cDNA clone designated T20782 was obtained from the public Arabidopsis Resource Centre, Ohio State University, 1735 Neil Avenue, Columbus, Ohio 43210. United States of America. The T20782 cDNA clone was localised broadly to the DNA interval on Arabidopsis chromosome 4 between the two markers g8300 and 06455 shown in FIG. 4. Using a polymerase chain reaction (PCR) based approach DNA primers (5'-AGAACAGCAGATACACGGA-3'SEQ ID NO:15 and 5'-CTGAAGAAGGCTGGACAAT-3'), SEQ ID NO:16 designed to the T20782 cDNA nucleotide sequence were used to screen Arabidopsis YAC clone libraries. The T20782 cDNA clone was found to localise to YACs (CIC1F9, CIC10E9, CIC11D9) identified on the Arabidopsis chromosome 4 g8300 and 06455 interval (FIG. 4). The same approach was used to further localise clone T20782 to YAC clone yUP5C8, the same YAC designated to contain the rsw1 locus in the same chromosome interval (FIG. 4).

Furthermore, amplification of the YAC clone yUP5C8 using primers derived from T20782 produces a 500 bp fragment containing two putative exons identical to part of the T20782 nucleotide sequence, in addition to two intron sequences.

The cDNA T20782 was considered as a candidate gene involved in cellulose biosynthesis.

EXAMPLE 4

Nucleotide Sequence Analysis of the cDNA Clone T20782

The nucleotide sequence of the cDNA clone T20782 is presented in SEQ ID NO:1. The nucleotide sequence was obtained using a Dye Terminator Cycle Sequencing kit (Perkin Elmer cat. #401384) as recommended by the manufacturer. Four template clones were used for nucleotide sequencing to generate the sequence listed. The first template was the cDNA clone T20782. This template was sequenced using the following sequencing primers:

a) 5'-CAATGCATTCATAGCTCCAGCCT-3' (SEQ ID NO:17)

b) 5'-AAAAGGCTGGAGCTATGAATGCAT-3' (SEQ ID NO:18)

c) 5'-TCACCGACAGATTCATCATACCCG-3' (SEQ ID NO:19)

d) 5'-GACATGGAATCACCTTAACTGCC-3' (SEQ ID NO:20)

e) 5'-CCATTCAGTCTTGTCTTCGTAACC-3' (SEQ ID NO:21)

f) 5'-GGTTACGAAGACAAGACTGAAATGG-3' (SEQ ID NO:22)

g) 5'-GAACCTCATAGGCATTGTGGGCTGG-3' (SEQ ID NO:23)

h) 5'-GCAGGCTCTATATGGGTATGATCC-3' (SEQ ID NO:24)

i) Standard M13 forward sequencing primer.

j) Standard T7 sequencing primer.

The second template clone (T20782 SphI deletion clone) was constructed by creating a DNA deletion within the T20782 clone. The T20782 clone was digested with the restriction enzyme SphI, the enzyme was heat-killed. the DNA ligated and electroporated into NM522 *E.coli* host cells. The T20782 SphI deletion clone was then sequenced using a standard M13 forward sequencing primer. Two other deletion clones were made for DNA sequencing in a similar fashion but the restriction enzymes EcoRI and SmaI were used. The T20782 EcoRI deletion clone and the T20782 SnaI deletion clone were sequenced using a standard T7 sequencing primer. The DNA sequence shown in SEQ ID NO:1 is for one DNA strand only however those skilled in the art will be able to generate the nucleotide sequence of the complementary strand from the data provided.

The amino acid sequence encoded by clone T20782 was derived and is set forth in SEQ ID NO:2.

The T20782 clone encodes all but the first Aspartate (D) residue of the D, D, D, QXXRW signature conserved in the general architecture of β-glycosyl transferases. In particular, T20782 encodes 5 amino acid residues of the D, D, D, QXXRW (SEQ ID NO:37) signature, between amino acid positions 109 and 370 of SEQ ID NO:2. The conserved Aspartate, Aspartate, Glutamine. Arginine and Tryptophan amino acid residues are shown below, in bold type, with the local amino acid residues also indicated:

1. Amino acid residues 105 to 113 of SEQ ID NO:2: LLNVDCDHY;

2. Amino acid residues 324 to 332 of SEQ ID NO:2: SVTEDILTG; and

3. Amino acid residues 362 to 374 of SEQ ID NO:2: DRLNQVLRWALGS.

It must be noted that these invariable amino acids merely indicate that the T20782 derived amino acid sequence belongs to a very broad group of glycosyl transferases. Some of these enzymes such as cellulose synthase, chitin synthase, alginate synthase and hyaluronic acid synthase produce functionally very different compounds.

The presence of the conserved amino acid residues merely indicate that the T20782 clone may encode a β-glycosyl transferase protein such as the cellulose gene product, cellulose synthase. The fact that the clone localises in the vicinity of a gene involved in cellulose iosynthesis is the key feature which now focus interest on the T20782 clone as a candidate for the RSW1 (cellulose synthase) gene.

The T20782 potentially codes for a cellulose synthase.

EXAMPLE 5

Nucleotide Sequence Analysis of the Genomic Clone 23H12

Clone 23H12 contains approximately 21 kb of *Arabidopsis thaliana* genomic DNA in the region between the left border and right border T-DNA sequences, and localises to the RSW1 candidate YAC yUP5C8. Clone 23H12 was isolated by hybridisation using EST20782 insert DNA. from a genomic DNA library made for plant transformation. Cosmid 12C4 was also shown to hybridize to the cDNA clone T20782, however this cosmid appears to comprise a partial genomic sequence corresponding to the related Ath-A cDNA sequence set forth in SEQ ID NO:7, for which the corresponding amino acid sequence is set forth in SEQ ID NO:8.

A restriction enzyme map of clone 23H12 is presented in FIG. 5.

Nucleotide sequence of 8411 bp of genomic DNA in the binary cosmid clone 23H12 was obtained (SEQ ID NO:3) by primer walking along the 23H12 template, using a Dye Terminator Cycle Sequencing kit (Perkin Elmer cat. #401384) as recommended by the manufacturer. The following primers at least, were used for DNA sequencing of the 23H12 clone DNA:

```
a)cs1-R      5'-CAATGCATTCATAGCTCCAGCCT-3'
             (SEQ ID NO: 17)
b)cs1-F      5'-AAAAGGCTGGAGCTATGAATGCAT-3'
             (SEQ ID NO: 18)
c)up         5'-AGAACAGCAGATACACGGA-3'
             (SEQ ID NO: 25)
d)ve76-R2    5'-ATCCGTGTATCTGCTGTTCTTACC-3'
             (SEQ ID NO: 26)
e)est1-R     5'-AATGCTCTTGTTGCCAAAGCAC-3'
             (SEQ ID NO: 27)
f)sve76-F    5'-ATTGTCCAGCCTTCTTCAGG-3'
             (SEQ ID NO: 28)
g)ve76-R     5'-CTGAAGAAGGCTGGACAATGC-3'
             (SEQ ID NO: 29)
h)B12-R1     5'-AGGTAAGCATAGCTGAACCATC-3'
             (SEQ ID NO: 30)
i)B12-R2     5'-AGTAGATTGCAGATGGTTTTCTAC-3'
             (SEQ ID NO: 31)
j)B12-R3     5'-TTCAATGGGTCCACTGTACTAAC-3'
             (SEQ ID NO: 32)
k)B12-R4     5'-ATTCAGATGCACCATTGTC-3'
             (SEQ ID NO: 33)
```

The structure of the RSW1 gene contained in cosmid clone 23H12 is also presented in FIG. 5. As shown therein, coding sequences in 23H12, from the last 12 bp of exon 7 to the end of exon 14, correspond to the full T20782 cDNA sequence (i.e. SEQ ID NO:1). The nucleotide sequences of the RSW1 gene comprising exons 1 to 8 were amplified from *A.thaliana* Columbia double-stranded cDNA, using amplification primers upstream of the RSW1 start site and a primer internal to the EST clone T20782.

The exons in the RSW1 gene range from 81 bp to 585 bp in length and all 5' and 3' intron/exon splice junctions conform to the conserved intron rule.

The RSW1 transcript comprises a 5'-untranslated sequence of at least 70 bp in length, a 3243 bp coding region and a 360 bp 3'-untranslated region. Northern hybridization analyses indicate that the RSW1 transcript in wild-type *A. thaliana* roots, leaves and inflorescences is approximately 4.0 kb in length, and that a similar transcript size occurs in mutant tissue (data not shown).

The derived amino acid sequence of the RSW1 polypeptide encoded by the cosmid clone 23H12 (i.e. the polypeptide set forth in SEQ ID NO:6) is 1081 amino acids in length and contains the entire D, D, D, QXXRW (SEQ ID NO:37) signature characteristic of β-glycosyl transferase proteins, between amino acid position 395 and amino acid position 822. The conserved Aspartate, Glutamine, Arginine and Tryptophan residues are shown below, in bold type, with the local amino acid residues also indicated:

1. amino acid residues 391 to 399 of SEQ ID NO:6: YVSDDGSAM
2. Amino acid residues 557 to 565 of SEQ ID NO:6: LLNVDCDHY;
3. Amino acid residues 776 to 784 of SEQ ID NO:6: SVTEDILTG; and
4. Amino acid residues 814 to 826 of SEQ ID NO:6: DRLNQVLRWALGS.

The second and third conserved Aspartate residues listed supra, and the fourth conserved amino acid sequence motif listed supra (i.e. QVLRW) are also present in the cDNA clone T20782 (see Example 4 above).

The 23H12 clone potentially encodes a cellulose synthase.

EXAMPLE 6

Complementation of the rsw1 Mutation

The complementation of the cellulose mutant plant rsw1 is the key test to demonstrate the function of the clone 23H12 gene product. Complementation of the rsw1 phenotype was demonstrated by transforming the binary cosmid clone 23H12, or a derivative clone thereof encoding a functional gene product, into the *Arabidopsis thaliana* cellulose mutant rsw1. Two DNA constructs (23H12 and pRSW1) were used to complement the rsw1 mutant plant line.

1. Construct 23H12

Clone 23H12 is described in Example 5 and FIG. 5.

2. Construct pRSW1

The 23H12 construct has an insert of about 21 kb in length. To demonstrate that any complementation of the phenotype of the rsw1 mutation is the result of expression of the gene which corresponds to SEQ ID NO:3. a genetic construct, designated as pRSW1, comprising the putative RSW1 gene with most of the surrounding DNA deleted, was produced. A restriction enzyme (RE) map of the RSW1 gene insert in pRSW 1 is provided in FIG. 5. To produce pRSW1, the RSW1 gene was subcloned from cosmid 23H12 and cloned into the binary plasmid pBIN19. Briefly, *Escherichia coli* cells containing cosmid 23H12 were grown in LB medium supplemented with tetracyclin (3.5 mg/L). Plasmid DNA was prepared by alkaline lysis and digested sequentially with restriction enzymes PvuII and SalI. Two co-migrating fragments of 9 kb and 10 kb. respectively, were isolated. as a single fraction from a 0.8% (w/v) agarose gel. The RSW1 gene was contained on the 10 kb PvuII/SalI fragment. The 9 kb fragment appeared to be a PvuII cleavage product not comprising the RSW1 gene. The restriction fragments were ligated into pBIN19 digested with SmaI and SalI. An aliquot of the ligation mix was introduced by electroporation into *E.coli* strain XLB1. Colonies resistant to kanamycin (50 mg/L) were selected and subsequently characterised by restriction enzyme analysis to identify those clones which contained only the 10 kb PvuII/SalI fragment comprising the RSW1 gene, in pBIN19.

3. Transfer of the 23H12 and pRSW1 Constructs to *Agrobacterium tumefaciens*

Cosmid 23H12 was transferred to Agrobacterium by triparental mating, essentially as described by Ditta et al. (1980). Three bacterial strains as follows were mixed on solid LB medium without antibiotics: Strain 1 was an *E. coli* helper strain containing the mobilising plasmid pRK2013, grown to stationary phase; Strain 2 was *E.coli* containing cosmid 23H12, grown to stationary phase; and Strain 3 was an exponential-phase culture of *A. tumefaciens* strain AGL1 (Lazo et al., 1991). The mixture was allowed to grow overnight at 28° C., before an aliquot was streaked out on solid LB medium containing antibiotics (ampicillin 50 mg/L. rifampicin 50 mg/L, tetracyclin 3.5 mg/L) to select for transformed A. tumefaciens AGL1. Resistant colonies appeared after 2–3 days at 28° C. and were streaked out once again on selective medium for further purification. Selected colonies were then subcultured in liquid LB medium supplemented with rifampicin (50 mg/L) and tetracyclin (3.5 mg/L) and stored at −80° C.

Plasmid pRSW1 (initially designated as p2029) was introduced into *A. tumefaciens* strain AGL1 by electroporation.

4. Transformation of rsw1 Plants

The rsw1 plant line was transformed with constructs 23H12 and pRSW1 using vacuum infiltration essentially as described by Bechtold et al. (1993).

5. Analysis of Radial Swelling in Transformants

Complementation of the radial swelling (rsw) phenotype , which is characteristic of the rsw1 mutant plant, was assayed by germinating transformed (i.e. T1 seed) rsw1 seeds obtained as described supra on Hoaglands plates containing 50 µg/ml kanamycin. Plates containing the transformed seeds were incubated at 21° C. for 10–12 days. Kanamycin-resistant seedlings were transferred to fresh Hoaglands plates containing 50 µg/ml kanamycin and incubated at 31° C. for 2 days Following this incubation, the root tip was examined for a radial swelling phenotype. Under these conditions, the roots of wild-type plants do not show any radial swelling phenotype however, the roots of rsw1 plants show clear radial swelling at the root tip and also have a short root compared to the wild-type plants. As a consequence, determination of the radial swelling phenotype of the transformed plants was indicative of successful complementation of the rsw1 phenotype.

The kanamycin-resistant seedlings were maintained by further growth of seedlings at 21° C., following the high temperature incubation. Once plants had recovered, the seedlings were transferred to soil and grown in cabinets at 21° C. (16 hr light/8 hr dark cycle). T2 seed was then harvested from mature individual plants.

Using the 23H12 construct for rsw1 transformation, a total of 262 kanamycin-resistant seedlings were obtained. All of these transformants were tested for complementation of the root radial swelling phenotype. A total of 230 seedlings showed a wild type root phenotype, while only 32 seedlings showed the radial swelling root phenotype characteristic of rsw1 plants. By way of example, FIG. 6 shows the phenotypes of transformed seedlings compared to untransformed wild-type and rsw1 seedlings, following incubation at 31° C. As shown in FIG. 6, there is clear complementation of the radial swelling phenotype in the transformed seedlings, with normal root length being exhibited by the transformed seedlings at 31° C.

Using the pRSW1 construct for transformation, a total of 140 kanamycin-resistant seedlings were obtained. All of the 11 seedlings tested for complementation of the root radial swelling phenotype showed a wild type root phenotype and none of the seedlings showed any signs of radial swelling in the roots (data not shown).

6. General Morphological Analysis of the Complemented rsw1 Mutant Line

Further characterisation of the complemented rsw1 plants has shown that other morphological characteristics of rsw1 have also been restored in the transgenic lines, for example the bolt (inflorescence) height, and the ability of the plants to grow wild type cotyledons, leaves, trichomes, siliques and flowers at 31° C. (data not shown).

7. Biochemical Complementation of the rsw1 Mutant Line

T2 seed from transformations using cosmid 23H12 as described supra or alternatively, using the binary plasmid pBin19 which lacks any RSW1 gene sequences, was sown on Hoagland's solid media containing kanamycin (50 µg/ml), incubated for 2 days at 21° C. and then transferred to 31° C. for 5 days. Wild-type *A. thaliana* Columbia plants were grown under similar conditions but without kanamycin in the growth medium. Kanamycin resistant T2 seedlings which have at least one copy of the 23H12 cosmid sequence, and wild-type seedlings, were collected and frozen for cellulose analysis.

Cellulose levels were determined as acetic-nitric acid insoluble material (Updegraph, 1969) for 10 lines of kanamycin-resistant T2 plants transformed with the 23H12 cosmid sequence, and compared to the cellulose levels in rsw1 mutant plants, wild-type *A.thaliana* Columbia plants and *A.thaliana* Columbia plants transformed with the binary plasmid pBin19. The results are provided in Table 7.

As shown in Table 7, the cellulose levels have been significantly elevated in the complemented rsw1 (T2) plants, compared to the cellulose levels measured in the rsw1 mutant parent plant. In fact, cellulose levels in the 23H12-transformed plants, expressed relative to the fresh weight of plant material or on a per seedling basis, are not significantly different from the cellulose levels of either wild-type *Arabidopsis thaliana* Columbia plants or *A.thaliana* Columbia transformed with the binary plasmid pBin19. These data indicate that the 23H12 cosmid is able to fully complement the cellulose-deficient phenotype of the rsw1 mutant.

Homozygous T3 lines are generated to confirm the data presented in Table 7.

Furthermore, data presented in Table 7 indicate that there is no difference in the rate of growth of the T2 transformed rsw1 plants and wild-type plants at 31° C., because the fresh weight of such plants does not differ significantly. In contrast, the fresh weight of mutant rsw1 seedlings grown under identical conditions is only approximately 55% of the level observed in T2 lines transformed with 23H12 (range about 30% to about 80%). These data support the conclusion that cellulose levels have been manipulated in the complemented rsw1 (T2) plants.

Furthermore, the rate of cellulose synthesis in 23H12-transformed plants and wild-type plants at 31° C. as measured by $^{14}C$ incorporation is also determined.

Furthermore, the β-1,4-glucan levels and starch levels in the 23H12 transformant lines are shown to be similar to the β-1,4-glucan and starch levels in wild-type plants.

TABLE 7

CELLULOSE LEVELS IN rsw1 PLANTS TRANSFORMED WITH COSMID CLONE 23H12

| PLANT LINE | SAMPLE SIZE (No. of plants) | SEEDLING FRESH WEIGHT (mg) | CELLULOSE (mg cellulose/ 100 mg tissue) | CELLULOSE (mg cellulose/ seedling) |
|---|---|---|---|---|
| 1.2 (rsw1 + 23H12) | 126 | 2.51 | 1.23 | 0.031 |
| 1.4 (rsw1 + 23H12) | 132 | 2.25 | 2.50 | 0.056 |
| 2.1 (rsw1 + 23H12) | 126 | 3.23 | 1.29 | 0.042 |
| 3.1 (rsw1 + 23H12) | 127 | 3.75 | 1.23 | 0.046 |
| 3.10 (rsw1 + 23H12) | 128 | 3.52 | 1.69 | 0.060 |
| 4.4 (rsw1 + 23H12) | 110 | 5.14 | 1.31 | 0.067 |
| 4.5 (rsw1 + 23H12) | 125 | 3.18 | 1.26 | 0.040 |
| 5.3 (rsw1 + 23H12) | 124 | 2.77 | 1.17 | 0.032 |
| 9.2 (rsw1 + 23H12) | 125 | 2.26 | 1.41 | 0.032 |
| 10.8 (rsw1 + 23H12) | 126 | 2.4 | 1.20 | 0.029 |
| Columbia/pBin19 | 106 | 2.64 | 1.34 | 0.035 |
| Columbia | 178 | 2.73 | 1.18 | 0.032 |
| rsw1 mutant | 179 | 1.77 | 0.84 | 0.015 |

EXAMPLE 7

Determination of the Full-Length Nucleotide Sequence Encoding the Wild-Type RSW1 Polypeptide

*Arabidopsis thaliana* double-stranded cDNA and cDNA libraries were prepared using the CAPFINDER cDNA kit (Clontech). RNA was isolated from wild-type Columbia grown in sterile conditions for 21 days.

Approximately 100,000 cDNA clones in an unamplified cDNA library were screened under standard hybridization conditions at 65° C., using a probe comprising $^{32}$P-labelled DNA amplified from double stranded cDNA. To prepare the hybridization probe, the following amplification primers were used:

1. 2280-F:5'GAATCGGCTACGAATTTCCCA 3' (2226–2246 of SEQ ID NO:3)
2. 2370-F:5'TTGGTTGCTGGATCCTACCGG 3' (2314–2334 of SEQ ID NO:3)
3. csp1-R:5'GGT TCT AAA TCT TCT TCC GTC 3' (6120–6140 of SEQ ID NO:3)

wherein the primer combinations were either 2280-F/csp1-R or 2370-F/csp1-R. The primer 2280-F corresponds to nucleotide positions 2226 to 2246 in SEQ ID NO:3, upstream of the translation start site. The primer 2370-F corresponds to nucleotide positions 2314 to 2334 in SEQ ID NO:3. encoding amino acids 7 through 13 of the RSW1 polypeptide. The primer csp1-R comprises nucleotide sequences complementary to nucleotides 588 to 608 of the T20782 clone (SEQ ID NO:1) corresponding to nucleotides 6120 to 6140 of SEQ ID NO:3. The hybridization probes produced are approximately 1858 nucleotides in length (2280-F/csp1-R primer combination) or 1946 nucleotides in length (2370-F/csp1-R primer combination).

Five hybridizing bacteriophage clones were identified, which were plaque-purified to homogeneity during two successive rounds of screening. Plasmids were rescued from the positively-hybridizing bacteriophage clones, using the Stratagene excision protocol for the ZapExpress™ vector according to the manufacturer's instructions. Colony hybridizations confirmed the identity of the clones.

Isolated cDNA clones were sequenced by primer walking similar to the method described in Examples 4 and 5 supra.

A full-length wild-type RSW1 nucleotide sequence was compiled from the nucleotide sequences of two cDNA clones. First, the 3'-end of the cDNA, encoding amino acids 453–1081 of RSW1, corresponded to the nucleotide sequence of the EST clone T20782 (SEQ ID NO:1). The remaining cDNA sequence, encoding amino acids 1–654 of RSW1, was generated by amplification of the 5'-end from cDNA, using primer 2280-F, which comprises nucleotide sequences approximately 50–70 bp upstream of the RSW1 translation start site in cosmid 23 H12, and primer csp1-R, which comprises nucleotide sequences complementary to nucleotides 588 to 608 of the T20782 clone (SEQ ID NO:1).

Several amplified clones are sequenced to show that no nucleotide errors were introduced by the amplification process. The 5' and 3' nucleotide sequences are spliced together to produce the complete RSW1 open reading frame and 3'-untranslated region provided in SEQ ID NO:5.

Those skilled in the art will be aware that the 5'-end and 3'-end of the two incomplete cDNAs are spliced together to obtain a full-length cDNA clone. the nucleotide sequence of which is set forth in SEQ ID NO:5.

Of the remaining cDNA clones, no isolated cDNA clone comprised a nucleotide sequence which precisely matched the nucleotide sequence of the RSW1 gene present in cosmid 23H12. However, several clones containing closely-related sequences were obtained, as summarised in Table 8. The nucleotide sequences of the Ath-A and Ath-B cDNAs are provided herein as SEQ ID Nos: 7 and 9, respectively.

TABLE 8

CHARACTERISATION OF *A. thaliana* cDNA CLONES

| CLONE NAME | DESCRIPTION | LENGTH | SEQ ID NO: |
|---|---|---|---|
| RSW1.1A | chimeric clone | partial | not provided |
| RSW1A | chimeric clone | partial | not provided |
| Ath-A | 12C4 cDNA | full-length | SEQ ID NO: 7 |
| Ath-B | new sequence | full-length | SEQ ID NO: 9 |
| RSW4A | identical to Ath-B | full-length | not provided |

Figure 9:
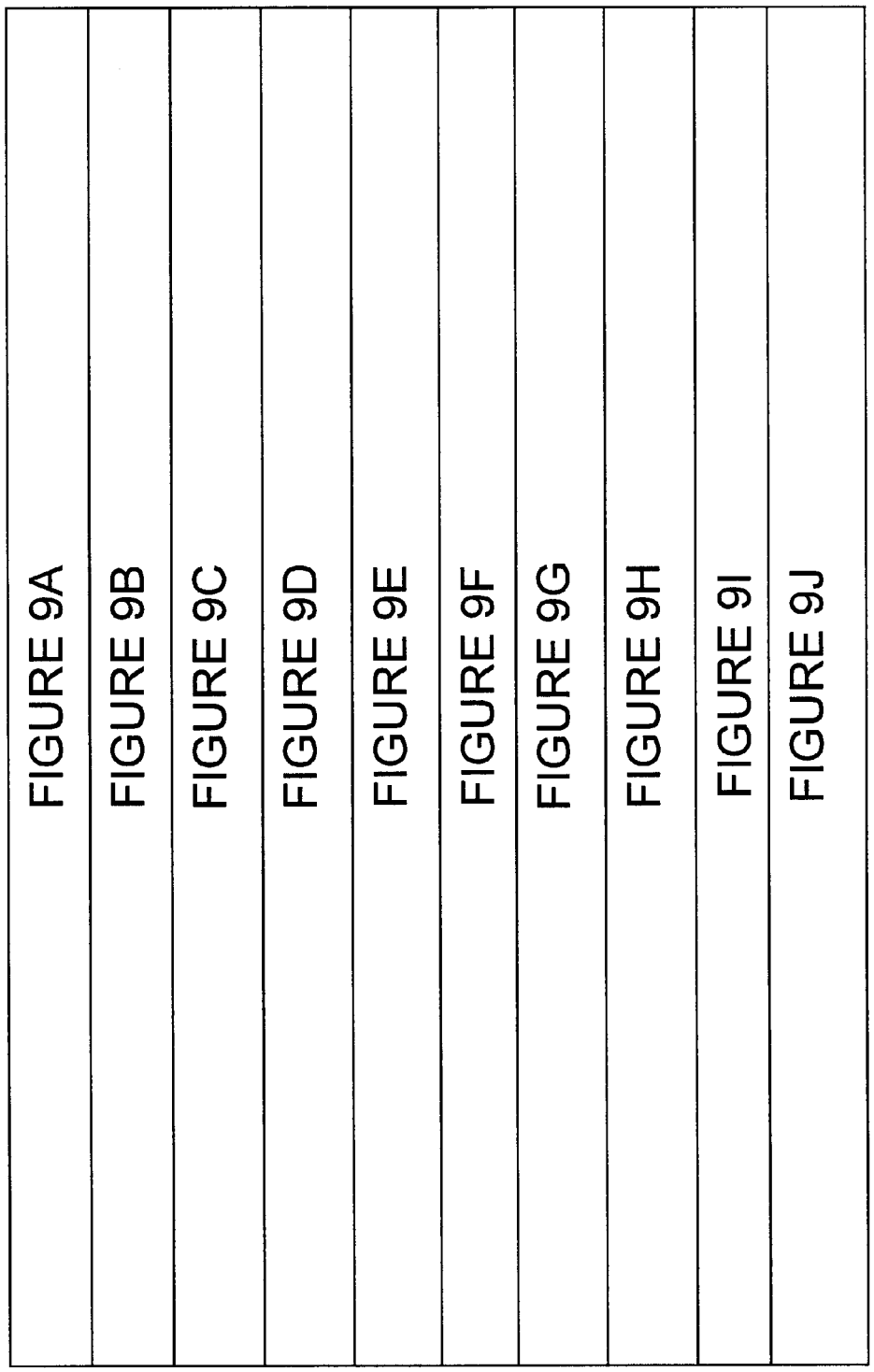

The derived amino acid sequences encoded by the cDNAs listed in Table 8, is provided in FIGS. 8 and 9 and SEQ ID Nos: 8 and 10 herein.

FIG. 10 a schematic representation of the important features of the RSW1 polypeptide which are conserved within *A.thaliana* and between *A.thaliana* and other plant species. In addition to the species indicated in FIG. 10, the present inventors have also identified maize, wheat, barley and Brassica ssp. cellulose biosynthetic genes by homology search. Accordingly, the present invention extends to cellulose genes and cellulose biosynthetic polypeptides as hereinbefore defined, derived from any plant species, including *A. thaliana*, cotton, rice, wheat, barley, maize, Eucalyptus ssp., Brassica ssp. Pinus ssp., Populus ssp., Picea ssp., hemp, jute and flax, amongst others.

EXAMPLE 8

Isolation of Full-Length Nucleotide Sequence Encoding the Mutant RSW1 Polypeptide

*Arabidopsis thaliana* double-stranded cDNA and cDNA libraries were prepared using the CAPFINDER cDNA kit (Clontech). RNA was isolated from *Arabidopsis thaliana* Columbia rsw1 mutant plants grown in sterile conditions for 21 days.

The full-length rsw1 mutant nucleotide sequence was generated by sequencing two amplified DNA fragments spanning the rsw1 mutant gene. The 5'-end sequence of the cDNA (comprising the 5'-untranslated region and exons 1–11) was amplified using the primer combination 2280-F/csp1-R (Example 7). The 3'-end sequence was amplified using the primers EST1-F and cs3-R set forth below:

1. Primer EST1-F: 5'AATGCTTCTTGTTGCCAAAGCA 3' (1399–1420 of SEQ ID NO:5)

2. Primer cs3-R: 5'GACATGGAATCACCTTAACTGCC 3' (3335–3359 of SEQ ID NO:5)

wherein primer EST1-F corresponds to nucleotide positions 1399–1420 of SEQ ID NO:5 (within exon 8) and primer cs3-R is complementary to nucleotides 3335–3359 of SEQ ID NO:5 (within the 3'-untranslated region of the wild-type transcript).

The full-length sequence of the mutant rsw1 transcript is set forth herein as SEQ ID NO:11.

Whilst not being bound by any theory or mode of action, a single nucleotide substitution in the rsw1 mutant nucleotide sequence (nucleotide position 1716 in SEQ ID NO:11), relative to the wild-type RSW1 nucleotide sequence (nucleotide position 1646 in SEQ ID NO:5), resulting in Ala549 being substituted with Val549 in the mutant polypeptide, may contribute to the altered activity of the RSW1 polypeptide at non-permissive temperatures such as 31° C. Additional amino acid substitutions are also contemplated by the present invention, to alter the activity of the RSW1 polypeptide, or to make the polypeptide temperature-sensitive.

EXAMPLE 9

Antisense Inhibition of Cellulose Production in Transgenic Plants

1. Construction of an Antisense RSW1 Binary Vector

One example of transgenic plants in which cellulose production is inhibited is provided by the expression of an antisense genetic construct therein. Antisense technology is used to target expression of a cellulose gene(s) to reduce the amount of cellulose produced by transgenic plants.

By way of exemplification, an antisense plant transformation construct has been engineered to contain the T20782 cDNA insert (or a part thereof) in the antisense orientation and in operable connection with the CaMV 35S promoter present in the binary plasmid pRD410 (Datla et al. 1992). More particularly, the T20782 cDNA clone, which comprises the 3'-end of the wild-type RSW1 gene, was digested with XbaI and KpnI and cloned into the kanamycin-resistant derivative of pGEM3zf(−), designated as plasmid, pJKKMf (−). The RSW1 sequence was sub-cloned, in the antisense orientation, into the binary vector pRD410 as a XbaI/SacI fragment, thereby replacing the β-glucuronidase (GUS or uidA) gene. This allows the RSW1 sequence to be transcribed in the antisense orientation under the control of the CaMV 35S promoter.

The antisense RSW1 binary plasmid vector was transferred to *Agrobacterium tumefaciens* strain AGL1, by triparental mating and selection on rifampicin and kanamycin, as described by Lazo et al. (1991). The presence of the RSW1 insert in transformed *A.tumefaciens* cells was confirmed by Southern hybridization analysis (Southern, 1975). The construct was shown to be free of deletion or rearrangements prior to transformation of plant tissues, by back-transformation into *Escherichia coli* strain JM101 and restriction digestion analysis.

2. Transformation of *Arabidopsis thaliana*

Eight pots, each containing approximately 16 *A. thaliana* ecotype Columbia plants, were grown under standard conditions. Plant tissue was transformed with the antisense RSW1 binary plasmid by vacuum infiltration as described by Bechtold et al (1993). Infiltration media contained 2.5% (w/v) sucrose and plants were infiltrated for 2 min until a vacuum of approximately 400 mm Hg was obtained. The vacuum connection was shut off and plants allowed to sit under vacuum for 5 min.

Approximately 34,000 T1 seed was screened on MS plates containing 50 μg/ml kanamycin, to select for plants containing the antisense RSW1 construct. Of the T1 seed sown, 135 kanamycin-resistant seedlings were identified, of which 91 were transferred into soil and grown at 21° C. under a long-day photoperiod (16 hr light; 8 hr dark).

Of the 91 transgenic lines, 19 lines were chosen for further analysis which had anther filaments in each flower which were too short to deposit pollen upon the stigma and, as a consequence, required hand-pollination to obtain T2 seed therefrom.

T2 seed from 14 of these 19 lines was plated out onto vertical Hoaglands plates containing kanamycin to determine segregation ratios. Between five and ten seed were plated per transgenic line. Control seeds, including *A. thaliana* Columbia containing the binary vector pBIN19 (Bevan, 1984) and segregating 3:1 for kanamycin resistance, and the rsw1 mutant transformed with the NPTII gene, also segregating 3:1 for kanamycin resistance, were grown under the same conditions. Kanamycin-resistant plants were transferred to soil and grown at 21° C. under long days, until flowering. Untransformed *Arabidopsis thaliana* Columbia plants were also grown under similar conditions. in the absence of kanamycin.

3. Morphology of Antisense-RSW1 Plants

A comparison of the morphology of antisense RSW1 plants grown at 21° C., to mutant rsw1 plants grown at the non-permissive temperature (i.e. 31° C.) has identified a number of common phenotypes. For example, the antisense plants exhibit reduced fertility, inflorescence shortening and have short anthers, compared to wild-type plants, when grown at 21° C. These phenotypes are also observed in mutant rsw1 plants grown at 31° C. These results suggest that the antisense construct in the transgenic plants may be targeting the expression of the wild-type RSW1 gene at 21° C.

FIG. 7 shows the reduced inflorescence (bolt) height in antisense 35S-RSW1 plants compared to wild-type *A. thaliana* Columbia plants grown under identical conditions.

4. Cell Wall Carbohydrate Analysis of Antisense Plants

T3 plants which are homozygous for the 35S-RSW1 antisense construct are generated and the content of cellulose therein is determined as described in Example 1. Plants expressing the antisense construct are shown to have significantly less cellulose in their cell walls, compared to wild-type plants. Additionally, the levels of non-crystalline β-1,4-glucan and starch are elevated in the cells of antisense plants, compared to otherwise isogenic plant lines which have not been transformed with the antisense genetic construct.

5. Antisense 35S-RSW1 mRNA Expression Levels in Transgenic Plants

Total RNA was extracted from 0.2 g of leaf tissue derived from 33 kanamycin-resistant T1 plants containing the antisense 35S-RSW1 genetic construct, essentially according to Longemann et al. (1986). Total RNA (25 μg) was separated on a 2.2M formaldehyde/agarose gel, blotted onto nylon filters and hybridized to a riboprobe comprising the sense strand sequence of the cDNA clone T20782. To produce the riboprobe, T7 RNA polymerase was used to transcribe sense RNA from a linearised plasmid template containing T20782, in the presence of [α-$^{32}$P]UTP. Hybridizations and subsequent washes were performed as described by Dolferus et al. (1994). Hybridized membranes were exposed to Phosphor screens (Molecular Dynamics, USA).

The levels of expression of the RSW1 antisense transcript were determined and compared to the level of fertility observed for the plant lines. As shown in Table 9, the level of antisense gene expression is correlated with the reduced fertility phenotype of the antisense plants. In 13 lines, a very high or high level of expression of the 35S-RSW1 antisense gene was observed and, in 11 of these lines fertility was reduced. Only lines 2W and 3E which expressed high to very high levels of antisense mRNA, appeared to be fully fertile. In 12 lines which expressed medium levels of antisense mRNA, approximately one-half were fertile and one-half appeared to exhibit reduced fertility. In contrast, in 8 plant lines in which only a low or very low level of expression of the antisense 35S-RSW1 genetic construct was observed, a wild-type (i.e. fertile) phenotype was observed for all but one transgenic line, line 2R.

Data presented in Table 9 and FIG. 7 indicate that the phenotype of the cellulose-deficient mutant rsw1 may be reproduced by expressing antisense RSW1 genetic constructs in transgenic plants.

To confirm reduced cellulose synthesis and/or deposition in transgenic plants expressing the antisense RSW1 gene, the level of cellulose is measured by the $^{14}$C incorporation assay or as acetic/nitric acid insoluble material as described in Example 1 and compared to cellulose production in otherwise isogenic wild-type plants. Cellulose production in the transgenic plants is shown to be significantly reduced compared to wild-type plants. The severity of phenotype of the transgenic plants thus produced varies considerably, depending to some extent upon the level of inhibition of cellulose biosynthesis.

TABLE 9

LEVELS OF ANTISENSE GENE EXPRESSION AND FERTILITY IN T1 LINES OF ANTISENSE 35S-RSW1 PLANTS

| T1 PLANT LINE | ANTISENSE 35S-RSW1 EXPRESSION | FERTILITY |
| --- | --- | --- |
| B | very high | sterile* |
| 2B | very high | sterile* |
| 3E | very high | fertile |
| 2E | high | sterile* |
| 2K | high | sterile* |
| 2M | high | sterile* |
| 2O | high | sterile* |
| 2P | high | sterile* |
| 2W | high | fertile |
| 2Z | high | sterile* |
| 3G | high | sterile* |
| 3Q | high | sterile* |
| 7Q | high | sterile* |
| 7N | medium | sterile* |
| 7G | medium | fertile |
| 1C | medium | sterile* |
| 2X | medium | sterile* |
| 2H | medium | fertile |
| C | medium | sterile* |
| F | medium | sterile* |
| 2Q | medium | fertile |
| 3P | medium | sterile* |
| 3T | medium | fertile |
| 5D | medium | sterile* |
| 6A | medium | fertile |
| 8E | low | fertile |
| 2R | low | sterile* |
| 7A | low | fertile |
| 7S | low | fertile |
| 7O | low | fertile |
| 7R | low | fertile |
| 1B | very low | fertile |
| 2U | very low | fertile |

*sterile phenotype not indicative of complete sterility, but that hand pollination at least, is required to obtain seed from such plants.

EXAMPLE 10

RSW1 Related Sequences in Rice Plants

To identify RSW1 related nucleotide sequences in rice, a genetic sequence database was searched for nucleotide sequences which were closely-related to one or more of the *Arabidopsis thaliana* RSW1 nucleotide sequences described in the preceding Examples. Rice EST S0542 (MAFF DNA bank, Japan) was identified, for which only a partial nucleotide sequences was available. Additionally, before the instant invention, there was no probable function attached to the rice EST S0542 sequence.

The present inventors have obtained the complete nucleotide sequence of clone S0542 and derived the amino acid sequence encoded therefor. The S0542 cDNA is only 1741 bp in length and appears to be a partial cDNA clone because, although it comprises 100 bp of 5'-untranslated sequence and contains the ATG start codon, it is truncated at 3'-end and, as a consequence encodes only the first 547 amino acid residues of the rice RSW1 or RSW1-like polypeptide. Based upon the length of the corresponding *Arabidopsis thaliana* RSW1 polypeptide (1081 amino acids), the rice RSW1 sequence set forth in SEQ ID NO:14 appears to contain approximately one-half of the complete amino acid sequence.

The N-terminal half of the rice RSW1 amino acid sequence is approximately 70% identical to the *Arabidopsis thaliana* RSW1 polypeptide set forth in SEQ ID NO:6, with higher homology (approximately 90%) occurring between amino acid residues 271–547 of the rice sequence. These data strongly suggest that S0542 is the rice homologue of the *A. thaliana* RSW1 gene. Alignments of rice, *A. thaliana* and cotton RSW1 amino acid sequences are presented in FIGS. 9 and 10.

To isolate full-length cDNA clones and genomic clone equivalents of S0542 (this study and MAFF DNA bank, Japan) or D48636 (Pear et al., 1996), cDNA and genomic clone libraries are produced using rice mRNA and genomic DNA respectively, and screened by hybridisation using the S0542 or D48636 cDNAs as a probe, essentially as described herein. Positive-hybridising plaques are identified and plaque-purified. during further rounds of screening by hybridisation, to single plaques.

The rice clones are sequenced as described in the preceding Examples to determine the complete nucleotide sequences of the rice RSW1 genes and derived amino acid sequences therefor. Those skilled in the art will be aware that such gene sequences are useful for the production of transgenic plants, in particular transgenic cereal plants having altered cellulose content and/or quality, using standard techniques. The present invention extends to all such genetic sequences and applications therefor.

EXAMPLE 11

RSW1 Related Sequences in Cotton Plants

A $^{32}$P-labelled RSW1 PCR fragment was used to screen approximately 200,000 cDNA clones in a cotton fibre cDNA library. The RSW1 PCR probe was initially amplified from *Arabidopsis thaliana* wild type cDNA using the primers 2280-F and csp1-R described in the preceding Examples. and then re-amplified using the primer combination 2370-F/csp1-R, also described in the preceding Examples.

Hybridisations were carried out under low stringency conditions at 55° C. Six putative positive-hybridising plaques were identified in the first screening round. Using two further rounds of screening by hybridisation, four of these plaques were purified to single plaques. Three plaques hybridise very strongly to the RSW1 probe while the fourth plaque hybridises less intensely.

We conclude that the positive-hybridising plaques which have been purified are strong candidates for comprising cotton RSW1 gene sequences or RSW1-like gene sequences. Furthermore, the cotton cDNAs may encode the catalytic subunit of cellulose synthase, because the subunit protein architecture of cellulose synthase appears to be highly conserved among plants as highlighted in the preceding Example.

Furthermore, a Southern blot of cotton genomic DNA digested with BglII was hybridised with the 5' end of the RSW1 cDNA, under low stringency hybridisation conditions at 55° C. Results are presented in FIG. 11. These data demonstrate that RSW1-related sequences exist in the cotton genome.

The cotton cDNA clones described herein are sequenced as described in the preceding Examples and used to produce transgenic cotton plants having altered fibre characteristics. The cDNAs are also used to genetically alter the cellulose content and/or quality of other plants, using standard techniques.

EXAMPLE 12

RSW1 Related Sequences in Eucalyptus ssp.

Putative Eucalyptus ssp. cellulose synthase catalytic subunit gene fragments were obtained by amplification using PCR. DNA primers were designed to conserved amino acid residues found in the *Arabidopsis thaliana* RSW1 and 12C4 amino acid sequences. Three primers were used for PCR. The primers are listed below:

pcsF-I 5'-AA/GAAGATIGAC/TTAC/TC/TTIAAA/ GGACTAA-3' (SEQ ID NO:34)

pcsR-II 5'-ATIGTIGGIGTICG/TA/GTTC/TTGA/T/G/ CCT/GA/T/C/GCC-3' (SEQ ID NO:35)

pcsF-II 5'-GCIATGAAA/GA/CGIGAITAC/TGAA/ GGA-3' (SEQ ID NO:36)

Using standard PCR conditions (50° C. annealing temperature) and solutions, the primer sets pcsF-I/pcsR-II and pcsF-II/pcsR-II were used to amplify genetic sequences from pooled Eucalyptus ssp. cDNA. In the first reaction primers pcsF-I and pcsR-II were used to generate a fragment approximately 700 bp in length. In the second PCR reaction, which used primers pcsF-II and pcsR-II, a fragment estimated to 700 bp was obtained. The sizes of the PCR fragments are within the size range estimated for the corresponding *Arabidopsis thaliana* sequences.

We conclude that the amplified Eucalyptus ssp. PCR fragments are likely to be related to the *Arabidopsis thaliana* RSW1 gene and may encode at least a part of the Eucalyptus ssp. cellulose synthase catalytic subunit.

The Eucalyptus ssp. PCR clones described herein are sequenced as described in the preceding Examples and used to isolate the corresponding full-length Eucalyptus ssp cDNAs and genomic gene equivalents. Those skilled in the art will be aware that such gene sequences are useful for the production of transgenic plants, in particular transgenic Eucalyptus ssp plants having altered cellulose content and/or quality, using standard techniques. The present invention extends to all such genetic sequences and applications therefor.

EXAMPLE 13

Non-Crystalline B-1,4-Glucan as a Modifier of Cell Wall Properties

The properties of plant cell walls depend on the carbohydrates, proteins and other polymers of which they are composed and the complex ways in which they interact. Increasing the quantities of non-crystalline β-1,4-glucan in cell walls affects those wall properties which influence mechanical, nutritional and many other qualities as well as having secondary consequences resulting from the diversion of carbon into non-crystalline glucan at the expense of other uses. To illustrate one of these effects, we investigated the ability of the non-crystalline glucan to hydrogen bond to other wall components particularly cellulose in the way that has been shown to be important for wall mechanics.

Hemicelluloses such as xyloglucans cross-link cellulose microfibrils by hydrogen bonding to the microfibril surface (Levy et al., 1991). Since the β-1,4-glucan backbone of xyloglucan is thought to be responsible for hydrogen bonding (with the xylose, galactose and fucose substitutions limiting the capacity to form further hydrogen bonds) we can expect the non-crystalline β-1,4-glucan also to have a capacity to hydrogen bond and cross link cellulose. The effectiveness of strong alkalis in extracting xyloglucans is thought to relate to their disruption of the hydrogen bonds with cellulose (Hayashi and MacLachlan, 1984).

To demonstrate that the non-crystalline β-1,4-glucan forms similar associations with the cellulose microfibrils, we examined whether the 4 M KOH fraction, extracted from shoots of the rsw1 mutant and from wild type RSW1 plants, contained non-crystalline glucan in addition to xyloglucan. The non-crystalline glucan was separated from xyloglucan in the 4 M KOH extract by dialysing the neutralised extract against distilled water and centrifuging at 14000 g for 1 hour. The pellet was shown to be a pure β-1,4-glucan by using the methods for monosaccharide analysis, methylation analysis and enzyme digestion used to characterise the glucan in the ammonium oxalate fraction (see Example 1).

Table 10 shows the presence of substantial quantities of glucan recovered in pure form in the pellet from 4 M KOH fractions extracted from the overproducing rsw1 mutant of *Arabidopsis thaliana*. These data also demonstrate the presence of smaller quantities of non-crystalline β-1,4-glucan in the 4 M KOH fraction from wild type plants, compared to rsw1, particularly when grown at 31° C.

TABLE 10

Glucose contents* of 4M KOH fractions from shoots of wild-type and rsw1 mutant *Arabidopsis thaliana* plants

|  | wild-type | | rsw1 mutant | |
| --- | --- | --- | --- | --- |
| Glucose fraction | 21° C. | 31° C. | 21° C. | 31° C. |
| xyloglucan and non-crystalline glucan in whole extract | 36.4 | 56.9 | 27.1 | 93.1 |
| non-crystalline glucan in pellet | 7.8 | 20.5 | 7.6 | 56.0 |

*nmol glucose/mg plant dry weight after TFA hydrolysis

The monosaccharide composition of the supernatant remaining after centrifugation was determined after TFA hydrolysis. These data, and data from methylation analysis, are consistent with the supernatant being a relatively pure xyloglucan. The supernatant was free of glucan, because no glucose could be released by the endocellulase/β-glucosidase mixture that released glucose from β-1,4-glucan.

The presence of both non-crystalline β-1,4-glucan and xyloglucan in the 4 M KOH fraction, when taken together with the implications from structural predictions (Levy et al, 1991), is consistent with some of the non-crystalline β-1,4-glucan in the wall hydrogen bonding to cellulose microfibrils in similar fashion to the β-1,4-glucan backbone of xyloglucan.

The cross linking provided when xyloglucans and other hemicelluloses bind to two or more microfibrils is an important determinant of the mechanical properties of cellulosic walls (Hayashi, 1989). The effects of increasing the amounts of non-crystalline β-1,4-glucan in walls are likely to be greatest in walls which otherwise possess relatively low levels of cross linking as a result of high ratios of cellulose:hemicelluloses. Such conditions are common in secondary walls including those of various fibres, and the cellulose-:hemicellulose ratio is particularly high in cotton fibres.

The effects on wall mechanical properties of overproducing non-crystalline glucan are shown by transforming plants with the mutant allele of rsw1 (SEQ ID NO:11) operably under the control of either the RSW1 promoter derived from SEQ ID NO:3 or SEQ ID NO:4 or alternatively, an appropriate constitutive promoter such as the CaMV 35S promoter. Production of non-crystalline glucan is quantified by fractionating the cell walls using the methods described above to show in particular that non-crystalline glucan is recovered in the 4 M KOH fraction. Mechanical properties of the cell walls are measured using standard methods for fibre analysis to study parameters such as stress-strain curves, and breaking strain, amongst other properties.

EXAMPLE 14

Over-Expression of Cellulose Synthase in Transgenic Plants

Three strategies are employed to over-express cellulose synthase in *Arabidopsis thaliana* plants.

In the first strategy, the CaMV 35S promoter sequence is operably connected to the full-length cellulose synthase cDNA which is obtainable by primer extension of SEQ ID NO:1. This is achievable by cloning the full-length cDNA encoding cellulose synthase, in the sense orientation, between the CaMV 35S promoter or other suitable promoter operable in plants and the nopaline synthase terminator sequences of the binary plasmid pBI121.

In the second strategy, the coding part of the genomic gene is cloned, in the sense orientation, between the CaMV 35S promoter and the nopaline synthase terminator sequences of the binary plasmid pBI121.

In the third strategy, the 23H12 binary cosmid clone or the derivative pRSW1, containing the cellulose synthase gene sequence operably under the control of the cellulose synthase gene promoter and terminator sequences is prepared in a form suitable for transformation of plant tissue.

For Agrobacterium-mediated tissue transformation, binary plasmid constructs discussed supra are transformed into *Agrobacterium tumefaciens* strain AGL1 or other suitable strain. The recombinant DNA constructs are then introduced into wild type *Arabidopsis thaliana* plants (Columbia ecotype), as described in the preceding Examples.

Alternatively, plant tissue is directly transformed using the vacuum infiltration method described by Beshtold et al. (1993).

The transgenic plants thus produced exhibit a range of phenotypes, partly because of position effects and variable levels of expression of the cellulose synthase transgene.

Cellulose content in the transgenic plants and isogenic untransformed control plants is determined by the $^{14}C$ incorporation assay or as acetic/nitric acid insoluble material as described in Example 1. In general, the level of cellulose deposition and rates of cellulose biosynthesis in the transgenic plants are significantly greater than for untransformed control plants.

Furthermore, in some cases, co-supression leads to mimicry of the rsw1 mutant phenotype.

EXAMPLE 15

Site-Directed Mutagenesis of the RSW1 Gene

The nucleotide sequence of the RSW1 gene contained in 23H12 is mutated using site-directed mutagenesis, at several positions to alter its catalytic activity or substrate affinity or glucan properties. In one example, the RSW1 gene is mutated to comprise one or more mutations present in the mutant rsw1 allele.

The mutated genetic sequences are cloned into binary plasmid described in the preceding Examples, in place of the wild-type sequences. Plant tissue obtained from both wild-type *Arabidopsis thaliana* (Columbia) plants and *A. thaliana* rsw1 plants is transformed as described herein and whole plants are regenerated.

Control transformations are performed using the wild-type cellulose synthase gene sequence.

EXAMPLE 16

Phenotypes of Plants Expressing Mutated RSW1 Genes

Plants transformed with genetic constructs described in Example 15 (and elsewhere) are categorised initially on the basis of number of transgene copies, to eliminate variability arising therefrom. Plants expressing single copies of different transgenes are analysed further for cell wall components, including cellulose, non-crystalline β-1,4-glucan polymer, starch and carbohydrate content.

1. Cellulose Content

Cellulose content in the transgenic plants is determined by the $^{14}$C incorporation assay as described in Example 1. Cell walls are prepared fractionated and the monosaccharide composition of individual fractions determined as in Example 1.

2. Non-crystalline β-1,4-glucan Content

Transgenic plants expressing the rsw1 mutant allele exhibit a higher level of non-crystalline, and therefore extractable, β-1,4-glucan in cell walls compared to plants expressing an additional copy of the wild-type RSW1 allele. Thus, it is possible to change the crystallinity of the β-1,4-glucan chains present in the cell wall by mutation of the wild-type RSW1 allele.

3. Starch Content

Transgenic plants are also analysed to determine the effect of mutagenesis of the RSW1 gene on the level of starch deposited in their roots. The quantity of starch present in material prepared from the crude wall fraction is determined using the anthrone/$H_2SO_4$ method described in Example 1. The data show that mutating the RSW1 gene to the mutant rsw1 allele increases starch deposition. This demonstrates that the gene can be used to alter the partitioning of carbon into carbohydrates other than cellulose.

4. Cell Wall Composition

The cell wall composition of transgenic plant material is also analysed. Wild type and rsw1 and transgenic seedlings are grown for 2 d at 21° C. and then kept for a further 5 d at either 21° C. or 31° C. With transfer to 31° C. when the seed has scarcely germinated, the wall composition at final harvest largely reflects the operation of the mutated rsw1 gene product at its restrictive temperature. Cell wall fractionation is carried out in similar fashion to that described for the $^{14}$C-experiment (Example 1) and the monosaccharide composition of each fraction is quantified by GC/MS after hydrolysis with trifluoroacetic acid or, in the case of crystalline cellulose. $H_2SO_4$.

In some transgenic plants in which the RSW1 gene is mutated, the monosaccharide composition is comparable to that observed for homozygous rsw1 plants, at least in some cases, confirming that there is a major reduction in the quantity of crystalline cellulose in the final, acid insoluble fraction. Thus, mutation of the RSW1 gene can be performed to produce changes in the composition of plant cell walls.

EXAMPLE 17

Chemical Modification of the RSW1 Gene to Manipulate Cellulose Production and Plant Cell Wall Content As demonstrated in the preceding Examples, the RSW1 gene is involved in cellulose production and the manipulation of cell wall content.

In the present Example, to identify novel phenotypes and gene sequences important for the normal functioning of the cellulose synthase gene, the RSW1 gene is modified in planta, using the chemical mutagen EMS. The mutant plants are identified following germination and the modified RSW1 genes are isolated and characterised at the nucleotide sequence level. A sequence comparison between the mutant gene sequences and the wild type sequence reveals nucleotides which encode amino acids important to the normal catalytic activity of the cellulose synthase enzyme, at least in *Arabidopsis thaliana* plants.

This approach thus generates further gene sequences of utility in the modification of cellulose content and properties in plants.

EXAMPLE 18

Discussion

Five pieces of evidence make a compelling case that the RSW1 gene product encodes the catalytic subunit of cellulose synthase:

1. The rsw1 mutation selectively inhibits cellulose synthesis and promotes accumulation of a non-crystalline β-1,4-glucan;
2. The rsw1 mutation removes cellulose synthase complexes from the plasma membrane, providing a plausible mechanism for reduced cellulose accumulation and placing the RSW1 product either in the complexes or interacting with them;
3. The D,D,D,QXXRW (SEQ ID NO:37) signature identifies the RSW1 gene product as a processive glycosyl transferase enzyme (Saxena, 1995);
4. The wild type allele corrects the temperature sensitive phenotype of the rsw1 mutant; and
5. Antisense expression of the RSW1 in transgenic plants grown at 21° C. reproduces some of the phenotype of rsw1 which is observed following growth at 31° C.

Consistent with the plasma membrane location expected for a catalytic subunit, the putative 122 kDa RSW1 product contains 8 predicted membrane-spanning regions. Six of these regions cluster near the C-terminus (FIG. 10), separated from the other two by a domain that is probably cytoplasmic and has the weak sequence similarities to prokaryotic glycosyl transferases (Wong, 1990; Saxena, 1990; Matthyse, 1995; Sofia, 1994; Kutish, 1996).

RSW1 therefore qualifies as a member of the large family of *Arabidopsis thaliana* genes whose members show weak similarities to bacterial cellulose synthase. RSW1 is the first member of that family to be rigorously identified as an authentic cellulose synthase. Among the diverse genes in *A. thaliana*, at least two genes show very strong sequence similarities to the RSW1 gene and are most likely members of a highly conserved sub-family involved in cellulose synthesis. The closely related sequences come from cosmid 12C4, a partial genomic clone cross-hybridising with EST T20782 designated Ath-A. and from a full length cDNA designated Ath-B.

Ath-A resembles RSW1 (SEQ ID NO:5) at its N-terminus whereas Ath-B starts 22 amino acid residues downstream [FIG. 8 and FIGS. 9(i), (ii) and (iii)]. Closely related sequences in other angiosperms are the rice EST S0542 [FIGS. 9(i), (ii) and (iii)], which resembles the polypeptides encoded by RSW1 and Ath-A and the cotton celA1 gene (Pear, 1996) at the N-terminus.

The *Arabidopsis thaliana*, rice and cotton genes have regions of very high sequence similarity interspersed with variable regions (FIGS. 9 and 10). Most of the highest conservation among those gene products occurs in their central cytoplasmic domain where the weak similarities to the bacterial cellulose synthase occur. The N-terminal region that precedes the first membrane spanning region is probably also cytoplasmic but shows many amino acid substitutions as well as sequences in RSW1 that have no counterpart in some of the other genes as already noted for celA. An exception to this is a region comprising 7 cysteine residues with highly conserved spacings (FIG. 10). This is reminiscent of regions suggested to mediate protein-protein and protein-lipid interactions in diverse proteins including transcriptional regulators and may account for the striking sequence similarity between this region of RSW1 and two putative soybean bZIP transcription factors (Genbank SOYSTF1A and 1B).

In conclusion, the chemical and ultrastructural changes seen in the cellulose-deficient mutant combine with gene cloning and complementation of the mutant to provide strong evidence that the RSW1 locus encodes the catalytic subunit of cellulose synthase. Accumulation of non-crystalline β-1,4-glucan in the shoot of the rsw1 mutant suggests that properties affected by the mutation are required for glucan chains to assemble into microfibrils. Whilst not being bound by any theory or mode of action, a key property may be the aggregation of catalytic subunits into plasma membrane rosettes. At the restrictive temperature, mutant synthase complexes disassemble to monomers (or smaller oligomers) that are undetectable by freeze etching. At least in the shoot, the monomers seem to remain biosynthetically active but their β-1,4-glucan products fail to crystallise into microfibrils probably because the chains are growing from dispersed sites. Crystallisation into microfibrils, with all its consequences for wall mechanics and morphogenesis, therefore may depend upon catalytic subunits remaining aggregated as plasma membrane rosettes.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

REFERENCES

1. An et al. (1985) EMBO J. 4:277–284.
2. Ausubel, F. M., Brent, R., Kingston, R. E., Moore, D. D., Seidman, J. G., Smith, J. A. and Struhl, K. (1987) Current Protocols in Molecular Biology, Wiley Interscience (ISBN 047140338).
3. Baskin et al. (1992) Aust. J. Plant Physiol. 19:427–437.
4. Bechtold et al. (1993) Planta 316:1194–1199.
5. Bevan, M. (1984) Nucl. Acids Res. 12, 8711–8721.
6. Chang, C. et al (1988) Proc. Natl. Acad. Sci. (USA) 85, 6856–6860.
7. Cole et al. (1985) In Monoclonal antibodies in cancer therapy, Alan R. Bliss Inc., pp 77–96;
8. Crossway et al. (1986) Mol. Gen. Genet. 202:179–185.
9. Datla, R. S. S., Hammerlindl, J. K., Panchuk, B., Pelcher, L. E. and Keller, W. (1992) Gene, 211, 383–384.
10. Ditta G., et al. (1980) Proc. Natl. Acad. Sci. (USA) 77, 7347–7351.
11. Doares, S. H., Albersheim, P. and Darvill, A. G. (1991) Carb. Res. 210, 311–317.
12. Dolferus, R., Jacobs, M., Peacock, W. J. and Dennis, E. S. (1994) Plant Physiol. 105, 1075–1087.
13. Fromm et al. (1985) Proc. Natl. Acad. Sci. (USA) 82:5824–5828.
14. Haseloff, J., and Gerlach, W. L. (1988) Nature 334:586–594
15. Hayashi (1989) Ann Rev Plant Physiol. Plant Molecular Biol. 40, 139–168.
16. Hayashi and MacLachlan (1984) Plant Physiol. 75, 596–604.
17. Herrera-Estrella et al. (1983a) Nature 303:209–213.
18. Herrera-Estrella et al. (1983b) EMBO J. 2:987–995
19. Herrera-Estrella et al. (1985) In: Plant Genetic Engineering, Cambridge University Press, NY, pp 63–93.
20. Herth, W. (1985) Planta 164, 12–21.
21. Huse et al. (1989) Science 246: 1275–1281.
22. Kohler and Milstein (1975) Nature, 256: 495–499.
23. Konieczny, A. and Ausubel, F. (1993) Plant J. 4, 403–410.
24. Kozbor et al. (1983) Immunol. Today 4: 72.
25. Lazo, G. R., Stein, P. A. and Ludwig, R. A. (1991). Bio/technology 9,963–967.
26. Levy et al. (1991) Plant Journal 1, 195–215.
27. Longemann, J, Schell, J. and Willmitzer, L. (1987). Anal. Biochem. 163, 16–20.
28. Matthyse, A. G., White, S., and Lightfoot, R. (1995) J. Bacteriol. 177, 1069–1075.
29. McPherson et al. (1991) In: PCR:A Practical Approach. IRL Press. Oxford.
30. Nam, H.-G., et al. (1989) Plant Cell 1, 699–705.
31. Needs, P. W. and Selvendran, R. R. (1993) Phytochem. Anal. 4, 210–216.
32. Paszkowski et al. (1984) EMBO J. 3:2717–2722.
33. Pear, J. R.,et al (1996) Proc. Natl. Acad. Sci. (USA) 93, 12637–12642.
34. Saxena et al. (1990) Plant Mol. Biol. 15, 673–683.
35. Saxena et al. (1995) J.Bacteriol. 177: 1419–1424.
36. Sofia, H. J., et al (1994) Nucl. Acids Res. 22, 2576–2586.
37. Southern, E. M. (1975). J. Mol. Biol. 98, 503–517.
38. Updegraph, D. J. (1969) Analyt. Bioch. 32: 429–424.
39. Wong, H. C. et al (1990) Proc. Natl. Acad. Sci. (USA) 87:8130–8134.

What is claimed is:

1. An isolated nucleic acid molecule which encodes a cellulose synthase (CesA) polypeptide of plants or a catalytic subunit thereof having cellulose synthase activity, comprising the protein-encoding region of a sequence selected from the group consisting of SEQ ID NO1, SEQ ID NO:5, SEQ ID NO:7, SEQ ID NO:9, SEQ ID NO:11, and SEQ ID NO:13.

2. A genetic construct which comprises the isolated nucleic acid molecule according to claim 1 operably linked to a promoter sequence that is operable in a plant.

3. The genetic construct according to claim 2, wherein the nucleic acid molecule is operably connected to the promoter sequence in the sense orientation such that a cellulose synthase (CesA) polypeptide or a catalytic subunit thereof or RNA encoding said cellulose synthase or catalytic subunit is produced when said nucleic acid molecule is expressed in a plant cell containing said genetic construct.

4. The genetic construct according to claim 2, wherein the promoter is the CaMV 35S promoter of the *Arabidopsis thaliana* RSW1 gene promoter.

5. A method of increasing the level of cellulose in a plant cell, plant tissue, plant organ or whole plant, said method comprising expressing the isolated nucleic acid molecule according to claim 1 in said plant cell, plant tissue, plant organ or whole plant, in the sense orientation, for a time and under conditions sufficient to produce or increase expression of the cellulose synthase (CesA) polypeptide encoded by said nucleic acid and to increase the level of cellulose in said plant cell, plant tissue, plant organ or whole plant.

6. A method of reducing the level of non-crystalline beta-1,4-glucan in a plant cell, plant tissue, plant organ or whole plant, said method comprising expressing the isolated nucleic acid molecule according to claim 1 in said plant cell, plant tissue, plant organ or whole plant, in the sense orientation, for a time and under conditions sufficient to produce or increase expression of the cellulose synthase (CesA) polypeptide encoded by said nucleic acid and to reduce the level of non-crystalline beta-1,4-glucan in said plant cell, plant tissue, plant organ or whole plant.

7. A method of reducing the level of starch in a plant cell, plant tissue, plant organ or whole plant, said method comprising expressing the isolated nucleic acid molecule according to claim 1 in said plant cell, plant tissue, plant organ or whole plant, in the sense orientation, for a time and under conditions sufficient to produce or increase expression of the cellulose synthase (CesA) polypeptide encoded by said nucleic acid and to reduce the level of starch in said plant cell, plant tissue, plant organ or whole plant.

8. A method of producing a recombinant enzymatically active cellulose synthase (CesA) polypeptide in a plant cell, said method comprising expressing the isolated nucleic acid molecule according to claim 1 in said plant cell for a time and under conditions sufficient for the cellulose synthase (CesA) polypeptide encoded by said nucleic acid to be produced.

9. A transgenic plant transformed with an isolated nucleic acid molecule according to claim 1.

10. A transgenic plant transformed with a genetic construct according to claim 2.

* * * * *

UNITED STATES PATENT AND TRADEMARK OFFICE
CERTIFICATE OF CORRECTION

PATENT NO. : 6,495,740 B1  Page 1 of 1
DATED : December 17, 2002
INVENTOR(S) : Arioli et al.

It is certified that error appears in the above-identified patent and that said Letters Patent is hereby corrected as shown below:

Columns 19 and 20,
Table 2, under the heading of "Code", line 14, from the bottom, replace "Dmty" with -- Dmtyr --; and the last line, replace "[1001b]Dnm-met" with -- Dnmmet --.

Column 20,
Line 2, replace "muttons" with -- muteins --.

Column 30,
Line 44, replace "SnaI" with -- SmaI --.

Column 37,
Line 32, insert -- complimentary to -- before "3335-3359".

Column 45,
Line 9, replace "prepared fractionated" with -- prepared, fractionated --.

Column 133,
Line 6, replace "SEQ ID NO1" with -- SEQ ID NO:1 --.

Column 134,
Line 62, replace "of the *Arabidopsis*" with -- or the *Arabidopsis* --.

Signed and Sealed this

Eleventh Day of March, 2003

JAMES E. ROGAN
*Director of the United States Patent and Trademark Office*